(12) United States Patent
Hamilton et al.

(10) Patent No.: US 7,922,984 B2
(45) Date of Patent: *Apr. 12, 2011

(54) APPARATUS AND METHOD FOR CONTROLLED DELIVERY OF A GAS

(75) Inventors: Richard A. Hamilton, Beverly, MA (US); John J. Warner, Manchester-by-the-Sea, MA (US)

(73) Assignee: Selective Micro Technologies, LLC, Travelers Rest, SC (US)

( * ) Notice: Subject to any disclaimer, the term of this patent is extended or adjusted under 35 U.S.C. 154(b) by 640 days.

This patent is subject to a terminal disclaimer.

(21) Appl. No.: 10/225,769

(22) Filed: Aug. 22, 2002

(65) Prior Publication Data
US 2004/0022676 A1 Feb. 5, 2004

Related U.S. Application Data

(63) Continuation-in-part of application No. 09/785,634, filed on Feb. 16, 2001, now Pat. No. 6,602,466, which is a continuation-in-part of application No. 09/660,117, filed on Sep. 12, 2000, now Pat. No. 6,607,696.

(60) Provisional application No. 60/183,368, filed on Feb. 18, 2000, provisional application No. 60/190,028, filed on Mar. 17, 2000, provisional application No. 60/259,896, filed on Jan. 4, 2001, provisional application No. 60/341,429, filed on Dec. 17, 2001.

(51) Int. Cl.
| | |
|---|---|
| *A61L 9/00* | (2006.01) |
| *A61L 2/00* | (2006.01) |
| *A62B 7/08* | (2006.01) |
| *B65D 33/16* | (2006.01) |
| *B65D 25/08* | (2006.01) |
| *A01J 11/04* | (2006.01) |
| *B65B 3/00* | (2006.01) |
| *B65B 31/00* | (2006.01) |
| *B08B 7/00* | (2006.01) |
| *A61K 7/50* | (2006.01) |
| *B67D 5/00* | (2006.01) |
| *A62D 3/00* | (2007.01) |

(52) U.S. Cl. ............... 422/305; 422/1; 422/5; 422/6; 422/28; 422/29; 422/32; 422/34; 422/36; 422/37; 422/40; 422/123; 422/239; 422/240; 422/261; 422/292; 422/274; 422/275; 422/276; 422/277; 422/294; 422/300; 422/306; 422/902; 99/467; 206/219; 206/220; 206/221; 206/222; 206/213.1; 206/0.6; 206/0.7; 206/568; 53/403; 222/386.5; 222/3; 383/80; 43/124; 134/6; 510/143; 252/90; 252/187.23; 252/186.36

(58) Field of Classification Search ............. 422/1, 5–6, 422/28–29, 32, 34, 36–37, 40, 123, 239–240, 422/261, 292, 274–277, 294, 300, 305–306, 422/902; 99/467; 206/219–222, 213.1, 0.6, 206/0.7, 568; 53/403; 222/386.5, 3; 383/80; 43/124; 134/6; 510/143; 252/90, 187.23, 252/186.36

See application file for complete search history.

(56) References Cited

U.S. PATENT DOCUMENTS

| | | | |
|---|---|---|---|
| 2,022,262 A | 11/1935 | White | ............... 87/5 |
| 2,071,091 A | 2/1937 | Taylor | ............ 167/17 |
| 2,071,094 A | 2/1937 | Vincent | ........... 167/17 |
| 2,323,593 A | 7/1943 | Hampel e al. | ........... 23/152 |
| 2,482,891 A | 9/1949 | Aston | ............ 252/187 |
| 3,183,057 A | 5/1965 | Marks et al. | ............ 21/58 |
| 3,332,548 A | 7/1967 | Piazze et at | ........ 206/525 |
| 3,591,515 A | 7/1971 | Lovely | ............ 252/187 |
| 3,695,839 A | 10/1972 | Callerame | ........... 423/479 |
| 3,754,079 A | 8/1973 | Callerame | ........... 423/479 |
| 3,915,212 A | 10/1975 | Bujan et al. | ............. 150/8 |
| 3,950,158 A | 4/1976 | Gossett | .............. 62/4 |
| 4,055,672 A | 10/1977 | Hirsch et al. | ........... 426/127 |
| 4,094,119 A | 6/1978 | Sullivan | ............. 53/4 |
| 4,200,610 A | 4/1980 | Swaine et al. | |
| 4,528,228 A | 7/1985 | Clevenger | ............ 428/74 |
| 4,547,381 A | 10/1985 | Mason et al. | ........... 426/316 |
| 4,585,482 A | 4/1986 | Tice et al. | ........... 106/15.05 |
| 4,596,713 A | 6/1986 | Burdette | ............ 426/107 |
| 4,597,218 A * | 7/1986 | Friemel et al. | ............ 43/131 |
| 4,605,165 A * | 8/1986 | Van Loveren et al. | ........... 239/6 |

| | | | | |
|---|---|---|---|---|
| 4,613,544 A * | 9/1986 | Burleigh ............... 428/315.5 |
| 4,679,706 A * | 7/1987 | Magid et al. ............ 222/130 |
| 4,683,039 A | 7/1987 | Twardowski et al. ....... 204/95 |
| 4,689,169 A | 8/1987 | Mason et al. ........ 252/186.24 |
| 4,689,215 A | 8/1987 | Ratcliff ................... 424/53 |
| 4,696,811 A | 9/1987 | Ratcliff ................... 424/53 |
| 4,748,904 A * | 6/1988 | Razeto et al. ............ 99/467 |
| 4,758,239 A * | 7/1988 | Yeo et al. ............... 604/366 |
| 4,788,053 A | 11/1988 | Ratcliff ................... 424/53 |
| 4,792,442 A | 12/1988 | Ratcliff ................... 424/53 |
| 4,808,389 A | 2/1989 | Ratcliff ................... 424/53 |
| 4,818,519 A | 4/1989 | Ratcliff ................... 424/53 |
| 4,828,772 A * | 5/1989 | Lopatin et al. .......... 264/45.9 |
| 4,837,009 A | 6/1989 | Ractliff ................... 424/53 |
| 4,851,213 A | 7/1989 | Ratcliff ................... 424/53 |
| 4,886,657 A | 12/1989 | Ratcliff .................. 415/53 |
| 4,889,714 A | 12/1989 | Ratcliff ................... 424/53 |
| 4,923,753 A | 5/1990 | Walles et al. ......... 428/402.24 |
| 4,925,645 A | 5/1990 | Mason ................... 423/477 |
| 4,925,656 A | 5/1990 | Ratcliff ................... 424/53 |
| 4,932,155 A * | 6/1990 | Friemel et al. ............ 43/125 |
| 4,994,056 A | 2/1991 | Ikeda .................... 604/410 |
| 5,009,875 A | 4/1991 | Kelley et al. ........... 423/477 |
| 5,091,107 A | 2/1992 | Hutchings ........... 252/187.21 |
| 5,093,097 A | 3/1992 | Engstrom et al. ........ 423/479 |
| 5,126,070 A * | 6/1992 | Leifheit et al. ....... 252/186.36 |
| 5,165,910 A | 11/1992 | Oikawa et al. .......... 423/477 |
| 5,200,171 A | 4/1993 | Ratcliff ................... 424/52 |
| 5,267,646 A * | 12/1993 | Inoue et al. ............. 206/204 |
| 5,342,601 A | 8/1994 | Cawlfield et al. ....... 423/478 |
| 5,346,061 A | 9/1994 | Newman et al. ........ 206/221 |
| 5,354,932 A * | 10/1994 | Bhattacharyya et al. ..... 585/400 |
| 5,360,609 A | 11/1994 | Wellinghoff ........... 514/772.3 |
| 5,380,517 A | 1/1995 | Sokol .................... 423/477 |
| 5,380,518 A | 1/1995 | Roozdar ................ 423/477 |
| 5,416,141 A * | 5/1995 | Endres et al. ............ 524/109 |
| 5,441,345 A | 8/1995 | Garvey et al. .............. 383/9 |
| 5,458,244 A | 10/1995 | Emori .................... 206/527 |
| 5,486,344 A | 1/1996 | Winters et al. ........... 423/477 |
| 5,489,435 A | 2/1996 | Ratcliff .................. 424/422 |
| 5,523,118 A | 6/1996 | Williams .............. 427/208.8 |
| 5,545,389 A | 8/1996 | Winters et al. ........... 423/478 |
| 5,567,405 A | 10/1996 | Klatte et al. ............ 423/477 |
| 5,573,743 A | 11/1996 | Klatte et al. ............ 423/477 |
| 5,631,300 A | 5/1997 | Wellinghoff ........... 514/772.3 |
| 5,650,446 A | 7/1997 | Wellinghoff et al. .... 514/772.3 |
| 5,690,672 A * | 11/1997 | Cohen .................... 606/203 |
| 5,705,092 A * | 1/1998 | Wellinghoff et al. .... 252/187.21 |
| 5,707,739 A | 1/1998 | Wellinghoff et al. ....... 428/403 |
| 5,711,211 A | 1/1998 | Ide et al. |
| 5,719,100 A | 2/1998 | Zahradnik et al. .......... 502/417 |
| 5,730,948 A | 3/1998 | Klatte et al. ............ 423/477 |
| 5,770,171 A | 6/1998 | Sundblad et al. ........ 423/477 |
| 5,776,374 A | 7/1998 | Newsham et al. ........ 252/582 |
| 5,811,115 A | 9/1998 | Ratcliff .................. 424/422 |
| 5,834,003 A | 11/1998 | Ratcliff .................. 424/422 |
| 5,851,374 A | 12/1998 | Cowley et al. ............ 205/471 |
| 5,853,085 A | 12/1998 | Luttrell .................... 206/5.1 |
| 5,853,689 A | 12/1998 | Klatte .................... 423/478 |
| RE36,064 E | 1/1999 | Davidson et al. ......... 424/665 |
| 5,855,861 A | 1/1999 | Lee ....................... 423/477 |
| 5,856,085 A | 1/1999 | Wang et al. ................ 435/5 |
| 5,858,322 A | 1/1999 | Gray ..................... 423/478 |
| 5,879,378 A | 3/1999 | Usui |
| 5,885,543 A | 3/1999 | Klatte .................... 423/477 |
| 5,891,838 A | 4/1999 | Angell et al. ............ 510/312 |
| 5,895,638 A | 4/1999 | Tenney ................. 423/478 |
| 5,922,776 A | 7/1999 | Wellinghoff et al. .... 514/772.3 |
| 5,965,004 A | 10/1999 | Cowley et al. ............ 205/499 |
| 5,965,264 A | 10/1999 | Barenberg et al. ........... 428/402 |
| 5,968,454 A | 10/1999 | Deacon et al. ............ 422/120 |
| 5,972,238 A | 10/1999 | Rimpler et al. ......... 252/187.21 |
| 5,974,810 A | 11/1999 | Speronello .............. 62/66 |
| 5,980,826 A | 11/1999 | Barenberg et al. ........... 422/37 |
| 6,000,848 A | 12/1999 | Massioui .................. 383/80 |
| 6,033,704 A * | 3/2000 | Talley ................... 426/320 |
| 6,046,243 A | 4/2000 | Wellinghoff et al. ...... 514/772.3 |
| 6,077,495 A | 6/2000 | Speronello et al. ........ 423/477 |
| 6,132,748 A | 10/2000 | Khanna et al. ........... 424/405 |
| 6,174,508 B1 | 1/2001 | Klatte ................ 423/245.1 |
| 6,238,643 B1 | 5/2001 | Thangaraj et al. ......... 423/477 |
| 6,363,734 B1 | 4/2002 | Aoyagi .................. 062/264 |
| 6,376,032 B1 * | 4/2002 | Clarke et al. ........... 428/34.7 |
| 6,602,466 B2 * | 8/2003 | Hamilton et al. .............. 422/37 |
| 6,607,696 B1 * | 8/2003 | Hamilton et al. .............. 422/37 |
| 2001/0012504 A1 | 8/2001 | Thangaraj et al. ......... 423/477 |
| 2003/0180384 A1 | 9/2003 | Koermer et al. |

FOREIGN PATENT DOCUMENTS

| | | |
|---|---|---|
| CA | 959238 | 12/1974 |
| CN | 1104610 | 7/1995 |
| EP | 0 230 737 A1 | 12/1986 |
| EP | 0 423 817 A2 | 10/1990 |
| EP | 0 571 228 A2 | 5/1993 |
| EP | 0 571 228 A2 | 11/1993 |
| EP | 0 581 550 A1 | 2/1994 |
| EP | 0 611 162 B1 | 10/1999 |
| EP | 0 611 163 B1 | 10/1999 |
| FR | 02555552 A1 | 5/1985 |
| JP | 01071804 | 3/1989 |
| JP | 04-075554 | 3/1992 |
| JP | 02055201 | 2/1999 |
| WO | WO-94/25263 A1 | 11/1994 |
| WO | WO 98/38865 | 9/1998 |
| WO | WO 99/19001 | 4/1999 |
| WO | WO 99/24356 | 5/1999 |
| WO | WO 00/10695 A1 | 3/2000 |
| WO | WO 00/21879 | 4/2000 |
| WO | WO 00/32052 | 6/2000 |
| WO | WO 01/33961 | 5/2001 |
| WO | WO 02/00332 | 1/2002 |

OTHER PUBLICATIONS

K.K. Krause, DDS et al., The Effectiveness of Chlorine Dioxide in the Barrier System (visited Feb. 5, 2000) http://www.dentallogic.com/dentist/effects.htm.

G. D. Simpson et al., A Focus on Chlorine Dioxide, An Ideal Biocide (visited Feb. 5, 2000) http://clo2.com/readings/waste/corrosion.html.

European Search Report Application No. 01916105.8, dated Feb. 10, 2008.

European Search Report for Application No. 02805178.7—2113, dated Jun. 5, 2007.

* cited by examiner

*Primary Examiner* — Jill Warden
*Assistant Examiner* — Monzer R Chorbaji
(74) *Attorney, Agent, or Firm* — McCarter & English, LLP

(57) ABSTRACT

Disclosed are apparatus for delivery of a gas, e.g., carbon dioxide and/or chlorine dioxide, and methods of its use and manufacture. The apparatus includes a sachet constructed in part with a hydrophobic material. The sachet contains one or more reactants that generate a gas in the presence of an initiating agent, e.g., water. The apparatus can also include a barrier layer and/or a rigid frame. In another embodiment, the apparatus is combined with a reservoir that can be used to deliver a gas to the reservoir and, optionally, a conduit. In another embodiment, the apparatus is incorporated into a fluid dispersion system that includes a dispersion apparatus, e.g., a humidifier.

15 Claims, 21 Drawing Sheets

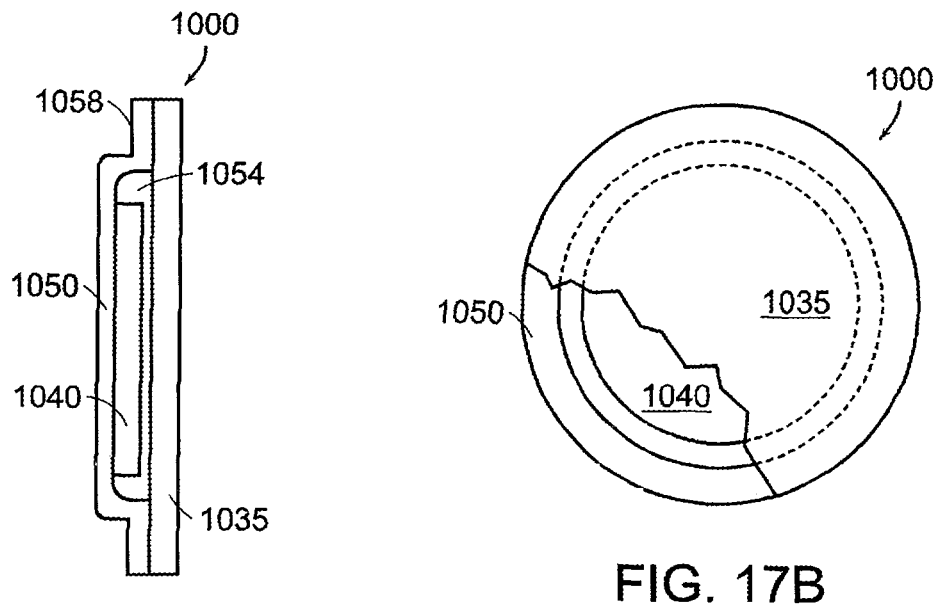
FIG. 17A
FIG. 17B
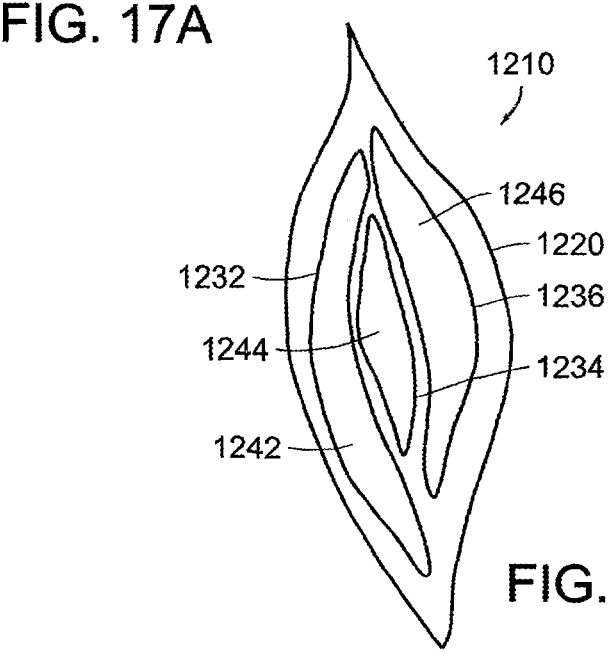
FIG. 19
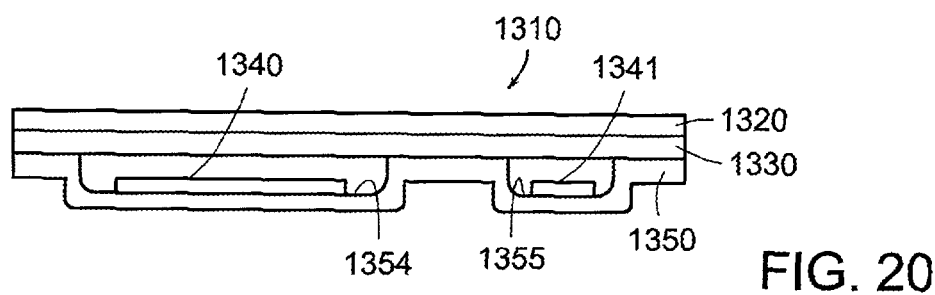
FIG. 20

APPARATUS AND METHOD FOR CONTROLLED DELIVERY OF A GAS

RELATED APPLICATIONS

This application is entitled to the benefit of earlier filed U.S. Provisional Patent Application Ser. No. 60/190,028, filed Mar. 17, 2000, No. 60/183,368, filed Feb. 18, 2000, No. 60/259,896, filed Jan. 4, 2001, and No. 60/341,429, filed Dec. 17, 2001, under 35 U.S.C. §119(e), and copending U.S. patent application Ser. No. 09/660,117, filed Sep. 12, 2000, and Ser. No. 09/785,364, filed Feb. 16, 2001, under 35 U.S.C. §120, the entire disclosure of each of which are hereby incorporated by reference herein.

FIELD OF THE INVENTION

The invention relates generally to apparatus and methods for delivery of a gas and more specifically to apparatus and methods for controlling the amount, rate and duration of gas delivery.

BACKGROUND OF THE INVENTION

The use of gas for retarding, controlling, killing or preventing microbiological contamination (e.g., bacteria, fungi, viruses, mold spores, algae and protozoa); retarding, preventing, or controlling biochemical decomposition; controlling respiration, deodorizing and/or retarding and preventing chemotaxis to name a few, is known. Such gases include, but are not limited to, chlorine dioxide, sulfur dioxide, nitrogen dioxide, nitric oxide, nitrous oxide, carbon dioxide, hydrogen sulfide, hydrocyanic acid, and dichlorine monoxide. For example, the use and efficacy of chlorine dioxide is documented and discussed in various publications such as G. D. Simpson et al., *A Focus on Chlorine Dioxide, An Ideal Biocide* (visited Feb. 5, 2000) http://clo2.com/readings/waste/corrosion.html, and K. K. Krause, DDS et al., *The Effectiveness of Chlorine Dioxide in the Barrier System* (visited Feb. 5, 2000) http://www.dentallogic.com/dentist/effects.htm.

In particular, chlorine dioxide has been found to be useful as a disinfectant, antiseptic and sanitizer. It is used, e.g., to disinfect drinking water and various water supplies. In addition, chlorine dioxide finds use as a bleaching agent for flour, fats and textiles. Chlorine dioxide also has shown great utility as an antiseptic for treating metal and plastic surfaces, as well as other substrates such as countertops, meat processing and packaging equipment, and dental and medical instruments and devices.

One disadvantage of the prior art methods for generating chlorine dioxide gas generally is that unsatisfactory levels of by-products or reactants remain as a residue. For example, in the case of chlorine dioxide gas, the byproduct chlorite leaves residues on food handling equipment and medical and dental surfaces. Human contact with such residues should be avoided or substantially minimized according to FDA and EPA regulations.

Another requirement in the food handling and related industries is the need for raw materials or ingredients that are safe to handle in the preparation of the disinfectant. The requirement is for the inclusion of reagents that are safe to use and, after generating chlorine dioxide, produce side products that are non-toxic and/or biodegradable.

Also, although it has great beneficial characteristics, chlorine dioxide can not be transported commercially as a concentrated gas for its use and instead has been generated at the site where it is used. Thus, an on-site gas generation plant typically is required to generate the gas that is then delivered to the fluid in which it will be used. Such apparatus takes up space and represents a significant added expense. Moreover, even when prior art apparatus do not require a separate gas generation component e.g., those shown in European Patent Publication No. 0 571 228 for sulfur dioxide generation, such apparatus are still undesirable because controlling the amount of gas generated, the efficiency of the generation, and the duration of the gas generation has proven difficult, if not unsuccessful.

There exists a need for the controlled, on-site generation of gases, such as sulfur dioxide and chlorine dioxide, which can be produced safely, efficiently and economically, without the necessity for a separate generation plant or unwanted by-products. The present invention addresses these needs.

SUMMARY OF THE INVENTION

A novel approach to the delivery of gas has now been discovered. The present invention uses a unique delivery system that controls the rate and efficiency of gas-producing reactions. Moreover, by using discreet amounts of reactant contained within a multi-layered apparatus, the skilled practitioner can now fabricate a gas delivery apparatus that is compact, cost-effective and safe. Furthermore, the present invention can be used for a variety of applications, including delivery of gas to air or water, for a variety of purposes including disinfection, deodorization, bleaching and sanitization.

In one aspect, the present invention features an apparatus for delivery of a gas. An exemplary embodiment of this apparatus generally includes an envelope, a sachet disposed within the envelope, and a reactant disposed within the sachet that generates a gas in the presence of an initiating agent, wherein the envelope allows release of the gas from the envelope.

One currently preferred embodiment of the invention features an apparatus for delivery of a gas which includes a first reactant disposed within a first sachet, a second reactant disposed within a second sachet, a third sachet disposed about the first sachet and the second sachet, an envelope disposed about the third sachet, a frangible pouch disposed within the envelope adjacent to the third sachet, and an initiating agent disposed within the frangible pouch. In this embodiment, the first reactant and the second reactant generate a gas in the presence of the initiating agent, and the envelope allows release of the gas from the apparatus.

In a third exemplary embodiment, the apparatus for delivery of a gas includes an envelope, a partition disposed within the envelope defining a first volume and a second volume, a first reactant disposed in the first volume, and a second reactant disposed within the second volume. In this preferred embodiment, the first reactant and the second reactant generate a gas in the presence of an initiating agent, and the envelope allows entry of the initiating agent into the apparatus.

In another embodiment, the apparatus for delivery of a gas includes a sachet and a reactant disposed within the sachet that generates a gas in the presence of an initiating agent. In this embodiment, the sachet allows contact of the initiating agent with the reactant and release of the gas from the apparatus.

In another aspect, the present invention features a method of forming an apparatus for delivery of a gas including the steps of (a) providing a multi-layer structure comprising a reactant layer centrally disposed between two sachet layers, and two envelope layers disposed adjacent to the two sachet layers such that the two sachet layers are centrally disposed between the two envelope layers, and (b) stamping the multi-layer structure such that the two envelope layers form an envelope defined about its perimeter by the stamp, and the two sachet layers form a sachet defined about its perimeter by the stamp.

In yet another aspect, the present invention features a method of delivering gas including the steps of (a) providing an apparatus for delivery of a gas comprising: an envelope, a sachet disposed within the envelope, and a reactant disposed within the sachet that generates a gas in the presence of an initiating agent, wherein the envelope allows release of the gas from the envelope; and (b) disposing the apparatus in an environment that comprises an initiating agent. The environment can be liquid and the initiating agent can be water. Alternatively, the environment can be gaseous and the initiating agent can be water vapor.

In yet another embodiment, the apparatus for delivery of a gas includes a barrier layer, a sachet layer disposed adjacent to the barrier layer, a reactant disposed between the barrier layer and the sachet layer that generates a gas in the presence of an initiating agent, and an envelope layer disposed adjacent to the sachet layer. In this embodiment, the envelope layer allows release of the gas from the apparatus.

In yet another embodiment, the apparatus for delivery of a gas includes a barrier layer, a sachet layer disposed adjacent to the barrier layer, and a reactant disposed between the barrier layer and the sachet layer that generates a gas in the presence of an initiating agent. In this embodiment, the sachet layer allows entry of the initiating agent into the apparatus.

In yet another aspect, the present invention features a method of delivering gas including the steps of (a) providing a multi-layer structure comprising a reactant layer centrally disposed between a sachet layer and a barrier layer, and an envelope layer disposed adjacent to the sachet layer, and (b) sealing the perimeter of the barrier layer, sachet layer and barrier layer such that the reactant is disposed in a volume defined by the sachet layer and the barrier layer.

In yet another aspect, the present invention features a method of delivering gas including the steps of (a) providing a multi-layer structure comprising a reactant layer centrally disposed between a sachet layer and a barrier layer, and (b) sealing the multi-layer structure such that the such that the reactant is disposed in a volume defined by the sachet layer and the barrier layer.

In yet another aspect, the present invention features a method of delivering gas including the steps of (a) providing an apparatus for delivery of a gas comprising an envelope layer, a sachet layer disposed adjacent to the envelope layer, a barrier layer disposed adjacent to the sachet layer, and a reactant disposed in a volume defined by the sachet layer and the barrier layer; and (b) disposing the apparatus in an environment that comprises an initiating agent.

In yet another aspect, the present invention features an apparatus for delivery of a gas including a sachet comprising a water vapor selective material, and reactant disposed within the sachet that generates a gas in the presence of an initiating agent.

In yet another aspect, the present invention features an apparatus that includes a sachet including a water vapor selective material, a partition disposed within the sachet defining a first volume and a second volume, a first reactant disposed in the first volume, and a second reactant disposed within the second volume, wherein the first reactant and the second reactant generate a gas in the presence of an initiating agent.

In yet another aspect, the present invention features an apparatus for delivery of a gas that includes a barrier layer, a sachet layer comprising water vapor selective material disposed adjacent to the barrier layer, and a reactant disposed in a volume defined by the barrier layer and the sachet layer that generates a gas in the presence of an initiating agent.

In yet another aspect, the present invention features an apparatus for delivery of a gas that includes a sachet comprising a rigid frame defining an opening and a sachet layer disposed about the opening, and a reactant disposed in the sachet, wherein the reactant generates a gas in the presence of an initiating agent.

In yet another aspect, the present invention features a fluid dispersion system for dispersing a gas. The system includes a fluid dispersion apparatus. and an apparatus for delivery of a gas disposed within the fluid dispersion apparatus. The apparatus includes a sachet, and a reactant disposed in the sachet that generates gas in the presence of an initiating agent.

In yet another aspect, the present invention features methods for deodorizing and/or inactivating pathogens, that includes the steps of providing the fluid dispersion system, and delivering the gas to one or more odor-causing compounds, wherein the gas inactivates the one or more odor-causing compounds.

In yet another aspect, the present invention features an apparatus for delivery of a gas to a reservoir including a sachet, a reactant disposed within the sachet, and a reservoir in fluid communication with the sachet, wherein the reactant generates a gas in the presence of an initiating agent.

In yet another aspect, the present invention features a method of delivering gas to a conduit. The method includes the step of providing an apparatus for delivery of a gas comprising a sachet, a reactant disposed within the sachet that generates a gas in the presence of an initiating agent, and a reservoir in fluid communication with the sachet. The method also includes the steps of coupling the apparatus to a conduit, and delivering a gas to the conduit by introducing an initiating agent to the reactant.

In short, the invention provides the art with a heretofore unappreciated method and apparatus for the controlled generation of a gas. Moreover, in accordance with the present teachings, the invention can also readily be applied to the generation of a liquid.

The invention will be understood further upon consideration of the following drawings, description and claims.

DESCRIPTION OF THE DRAWINGS

The invention is pointed out with particularity in the appended claims. The drawings are not necessarily to scale, emphasis instead generally being placed upon illustrating the principles of the invention. The advantages of the invention described above, as well as further advantages of the invention, can be better understood by reference to the description taken in conjunction with the accompanying drawings, in which:

FIGS. 17A and 17B are a cross-sectional side view and a perspective view, respectively, of still yet another exemplary embodiment of an apparatus constructed in accordance with the present invention;

FIG. 19 is a cross-sectional side view of still yet another exemplary embodiment of an apparatus constructed in accordance with the present invention;

FIG. 20 is a cross-sectional side view of still yet another exemplary embodiment of an apparatus in accordance with the present invention;

DETAILED DESCRIPTION OF THE INVENTION

Figure 1A:
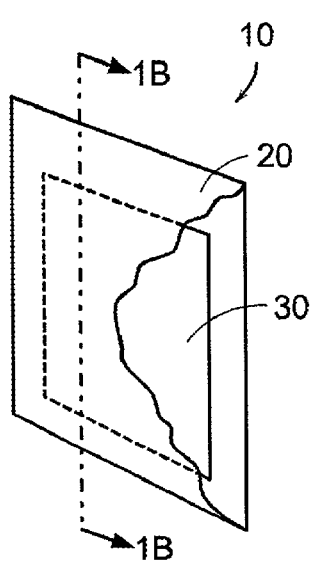
FIGS. 1A and 1B are a perspective view and a cross-sectional side view, respectively, of an embodiment of an apparatus constructed in accordance with the present invention.

A novel approach to the delivery of gas has now been discovered. By using discrete amounts of reactant contained within a multi-layered apparatus, the skilled practitioner can now fabricate a gas delivery apparatus that is compact, cost-effective, and safe. The present invention can be used for a variety of applications, including delivery of gas to air or water, for a variety of purposes including disinfection, deodorization, bleaching and sanitization.

One advantage to this approach is that gas can be generated without the need for mechanical equipment, thus freeing up any space such mechanical equipment would require. Another advantage is that the reactants, which can be dangerous to handle directly, are isolated from contact with the user by the layers, which enclose the reactant.

Another advantage is that the apparatus of the present invention does not allow for the dilution of the reactant. Because the reactant remains concentrated within the sachet, less reactant is necessary to drive the reaction to completion and the reaction is more efficient than it would be if the reactants were diluted. Furthermore, because the reaction is driven to completion, unreacted reactant is minimized or eliminated. The reactant concentration also minimizes unwanted by-products.

Yet another advantage is that the apparatus is small and therefore can be easily and economically shipped and administered. Yet another advantage is that the apparatus can be manipulated to allow for either rapid or slow delivery of gas. Another advantage is that the apparatus can be designed to deliver gas to either a gas, e.g., air, or a liquid, e.g., water. Other advantages will be evident to the practitioner having ordinary skill in the art.

In order to more clearly and concisely describe the subject matter of the claims, the following definitions are intended to provide guidance as to the meaning of specific terms used in the following written description, examples and appended claims.

As used herein the term "sachet" means a closed receptacle for reactant. The sachet is "closed" in the sense that the reactants are substantially retained within the sachet and the sachet volume is substantially sealed around its perimeter. However, the material or materials used to construct the sachet are chosen to allow entry of the initiating agent and exit of the gas generated. The material or materials used to construct sachets are referred to herein as "sachet layers." Sachet layers typically are constructed from a planar material, such as, but not limited to, a polymeric sheet or film. Preferred materials for sachet layers are described in greater detail below. Relying upon the teaching disclosed herein, and the general knowledge in the art, the practitioner of ordinary skill will require only routine experimentation to identify one or more sachet layers and/or construct one or more sachets adapted for the purpose at hand.

The sachets of the present invention also can include further materials, e.g., a sachet can comprise a barrier layer and sachet layer sealed about the perimeters of the layers to define a closed receptacle for reactant. Another example of a sachet is a rigid frame defining one or more openings and one or more layers, including at least one sachet layer, disposed about the one or more openings to define a closed receptacle for reactant. Further examples and embodiments are described in greater detail herein.

As used herein the term "envelope" means a closed receptacle wherein the envelope volume is sealed substantially about its perimeter, which contains at least one sachet and allows release of the gas from the envelope. The material or materials used to construct envelopes are referred to herein as "envelope layers." Envelope layers typically comprise a planar material such as a sheet or film, including, but not limited to perforated films, non-perforated films and membranes. Preferred materials for envelope layers are described in greater detail below. Relying upon the teaching disclosed herein, and the general knowledge in the art, the practitioner of ordinary skill will require only routine experimentation to identify one or more envelope layers and/or construct one or more envelopes adapted for the purpose at hand.

"Permeable layer," as used herein, refers to a layer that permits passage of gas generated by an apparatus of the present invention. Permeable layers typically are constructed from polymeric materials. Sachet layers and envelope layers are permeable layers.

"Impermeable layer," as used herein, refers to a layer that substantially prevents or hinders passage of initiating agent. As contemplated herein, the impermeable layer does not participate in the generation of gas in that it does not facilitate contact between initiating agent and reactant. Impermeable layers can be constructed from various materials, including polymeric material, glass, metal, metallized polymeric material and/or coated papers. Preferred materials for impermeable layers are described in greater detail below. As used herein, barrier layers are impermeable layers.

The skilled artisan will appreciate that what is considered to be an "impermeable layer" and what is considered to be a "permeable layer" is defined relative to the transmission rates of the respective layers used to construct apparatus of the present invention and the desired shelf life of the product. Relying upon the teaching disclosed herein, and the general knowledge in the art, the practitioner of ordinary skill will require only routine experimentation to identify and/or construct one or more impermeable layers and one or more permeable layers adapted for the purpose at hand.

As used herein "reactant" means a reactant or a mixture of reactants that generate gas in the presence of an initiating agent. For purposes of the present invention, initiating agent includes, but is not limited to, gaseous or liquid water. For example, for dry biocidal applications of the present invention, such as for the reduction of molds when shipping fruit, moisture in the atmosphere can be used as an initiating agent. The term "dry application" for the purposes of this application means at least an application where the apparatus of the present invention is not immersed in water or any other liquid. The term "wet application" for the purposes of the present invention means at least an application where the apparatus of the present invention is immersed in water, or other liquid, which can optionally include water. For wet biocidal applications, i.e., when the apparatus of the present invention is immersed in water or any other aqueous medium, such as that used for disinfecting dental or food equipment, the water in which the apparatus is immersed can be used as the initiating agent. Alternatively, the initiating agent can be included within the apparatus, e.g., contained in a frangible pouch disposed within the apparatus.

Generation of a gas, e.g., by acid activation, is well known in the art. For example, chlorine dioxide ($ClO_2$) is generated from sodium chlorite and an acid, such as citric acid, in the presence of moisture as follows.

$$5ClO_2^- + 4H^+ \longleftrightarrow 4ClO_2 + 2H_2O + Cl^- \quad (I)$$

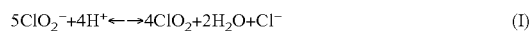

$$ClO_2^- \rightarrow ClO_2 + e^- \quad (II)$$

Specific examples of this reaction include the following.

$$2NaClO_2 + Na_2S_2O_8 \rightarrow 2ClO_2 + 2Na_2SO_4 \quad (III)$$

$$2NaClO_2 + NaOCl + HCl \rightarrow 2ClO_2 + 2NaCl + NaOH \quad (IV)$$

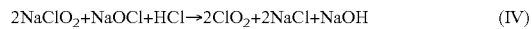

Alternatively, chlorine dioxide can be produced by the reduction of a chlorate, e.g., sodium chlorate or potassium chlorate, in the presence of an acid, e.g., oxalic acid. Generally the reaction occurs as follows.

$$ClO_3^- + 2H^+ + e^- \rightarrow ClO_2 + H_2O \quad (V)$$

For example, reduction of sodium chlorate by acidification in the presence of oxalic acid to produce chlorine dioxide can proceed as follows.

$$2\ NaClO_3 + H_2C_2O_4 \rightarrow 2ClO_2 + 2CO_2 + 2H_2O \quad (VI)$$

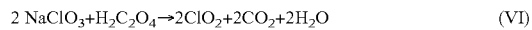

Another example of generation of a gas by acid activation is the activation of a sulfite, e.g., sodium bisulfite or potassium bisulfite, with an acid, e.g., fumaric acid and/or potassium bitartrate, in the presence of moisture to form sulfur dioxide.

$$NaHSO_3 + 4H^+ \longleftrightarrow SO_2 + 2H_2O + Na^+ \quad (VII)$$

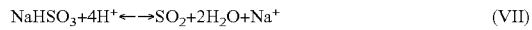

Yet another example is the acid activation of a carbonate, e.g., calcium carbonate with an acid, e.g., citric acid, to form carbon dioxide.

$$CaCO_3 + 2H^+ \longleftrightarrow CO_2 + H_2O + Ca^+ \quad (VIII)$$

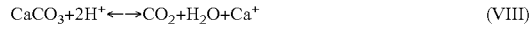

Other applications will be apparent to the skilled practitioner. For example, the generation of nitrogen dioxide by the acid activation of a nitrite, e.g., sodium nitrite or potassium nitrite. Alternative routes for generation of a gas, e.g., reduction of chlorates by sulfur dioxide (Mathieson Process), are well known in the art and can be utilized in accordance with the present invention.

The present invention can be used in a wide variety of applications. For example, chlorine dioxide can be used for the disinfection of water, e.g., municipal water treatment: as a disinfectant for foods, beverages, fruits and vegetables; and for the cleaning and disinfection of medical, dental and food equipment. Chlorine dioxide has been shown to be an effective disinfectant at concentrations as low as 0.2 mg/L. Chlorine dioxide is a desirable replacement for chlorine, the traditional water treatment chemical, because it has been found to inactivate microbes at lower levels and over a wider pH range. For example, chlorine dioxide can be used to reduce or eliminate biofilms because it penetrates the cell wall of naturally occurring, colony-building microorganisms and disrupts the proteins necessary for reproduction. Moreover, chlorine dioxide does not produce chlorinated by-products, e.g., trihalomethanes. Moreover, it has been found to be active against pathogens that are resistant to chlorine. It can be used as a slimicide in paper or pulp machines, for wastewater treatment, and for industrial water treatment, e.g., cooling or recycle streams. It can be used for odor control or as an aerial biocide and virucide. It can be used for the treatment of sulfides in the oil industry, for industrial cleaning, e.g., circuit board cleansing, and for paper or tallow bleaching. Sulfur dioxide also has a variety of uses, such as a mold and fungus inhibitor for use in shipping and storing fruits and vegetables. Based on the teachings disclosed herein the practitioner of ordinary skill will appreciate the numerous other applications for which the present invention can be used and provides a heretofore unmet need.

The present invention relates to apparatus and methods for delivering biocidal-effective amounts of a gas such as chlorine dioxide. The apparatus and methods of the present invention achieve delivery of a desired amount of gas, at a desired rate, over a desired time period. This is accomplished by disposing suitable reactants in a defined and confined volume such that upon initiation, the reactants, initiating agent, products, and by-products are held within a desired concentration range. The amount, rate and duration of delivery can be manipulated by, e.g., choice of sachet layers, sachet volume, reactant amount, reactant ratio, envelope layers, and envelope volume. Such manipulations can be exercised by the artisan using only routine experimentation in view of the teachings disclosed herein together with knowledge in the art.

Generally, the present invention also relates to an apparatus for delivery of a gas that includes reactant disposed in a volume defined by at least one permeable layer and at least one impermeable layer. The one or more permeable layers can include a sachet layer and/or an envelope layer, and allows release of the gas from the envelope. The one or more impermeable layers can include one or more barrier layer.

Figure 1B:
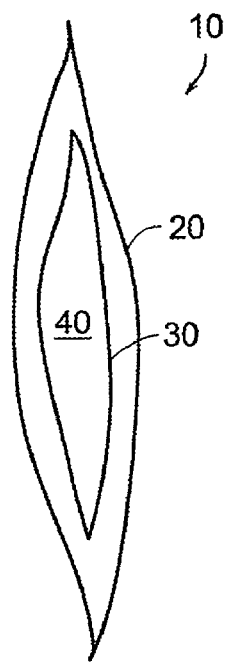

FIGS. 1A and 1B are a perspective view and a cross-sectional side view, respectively, of an embodiment of an apparatus 10 constructed in accordance with the present invention. In general overview, apparatus 10 includes an envelope 20, a sachet 30 disposed within the envelope 10, and reactant 40 disposed within sachet 30 that generates a gas in the presence of an initiating agent, e.g., water. Envelope 20 allows contact of the initiating agent with sachet 30 and release of the gas from envelope 20.

Apparatus 10 is particularly useful for the rapid release of a gas for wet applications e.g., delivery of 5 to 50 mg chlorine dioxide gas per liter of water in 5 to 15 minutes. The function of the envelope is to control the influx of the initiating agent, while limiting the diffusion of the reactants from the sachet to the surrounding fluid, be it gaseous or liquid. The envelope also allows the gas to diffuse to the surrounding fluid, be it gaseous or liquid. By limiting transmission of the initiating agent into the apparatus, and limiting and/or preventing diffusion of the reactants out of the apparatus, the reactant remains concentrated and the pH of the reactive system is localized within the apparatus to optimize the conversion of reactant to gas. Additionally, intermediates and/or by-products of the reaction, e.g., water, also can contribute to the efficiency and/or duration of the reaction by its affect on the equilibrium of the reactions.

The envelope preferably is constructed of a material that is durable and stable. Preferably, it also is capable of fusing to a like material upon the application of heat for construction purposes, e.g., so that two pieces of such material can be fused about its perimeter to form the envelope. The envelope can be constructed of various materials, including polymeric material, such as perforated films, membranes and selective transmission films.

Preferably, an envelope constructed of perforated film is constructed of envelope layers having a water vapor transmission rate (WVTR) between about 50 $g/m^2/24$ hrs and about 1,000 $g/m^2/24$ hrs, more preferably, between about 200 $g/m^2/24$ hrs and about 800 $g/m^2/24$ hrs, and most preferably between about 400 $g/m^2/24$ hrs and about 700 $g/m^2/24$ hrs. The measurement of water vapor transmission rate is routine and well known in the art. Also, the envelope preferably is hydrophobic.

Perforated films suitable for the construction of the envelope in accordance with the present invention include, but are not limited to, polymeric material, e.g., Cryovac® perforated films available from Sealed Air Corporation (Duncan, S.C.). One such film is a hydrophobic polypropylene copolymer film sold under the designation SM700 by Sealed Air Corporation and has 330 holes per square inch having a diameter of 0.4 mm, a 6.4% perforated area, a thickness of about 20 microns, and a water vapor transmission rate of 700 $g/m^2/24$ hrs. Another suitable film is a hydrophobic polypropylene copolymer film sold under the designation SM60 by Sealed Air Corporation and has 8 holes per square inch having a diameter of 0.4 mm, a 0.2% perforated area and a water vapor transmission rate of 65 $g/m^2/24$ hrs. The artisan can readily identify suitable equivalents of any of the foregoing by exercising routine experimentation.

In another preferred embodiment, the envelope or envelopes can be constructed from hydrophobic, liquid water permeable material, such as polyethylene or polypropylene. These materials preferably are between about 1 mil and about 10 mils thick with a water intrusion pressure of about 30 millibars or 30 millibars or less. Hydrophobic materials suitable for use as envelope layers in accordance with the present invention include, but are not limited to, non-woven polyethylene such as the TYVEK® non-woven polyethylenes from DuPont Company (Wilmington, Del.), e.g., the TYVEK® 1025D non-woven polyethylene which has an intrusion pressure of less than 30 millibars.

Envelopes can be constructed, at least in part, from a hydrophilic membrane having a pore size between about 0.01 microns and about 50 microns. More preferably, the pore size is between about 0.05 microns and 40 microns, and most preferably, the pore size is between about 0.1 and about 30 microns. Preferred membranes also include, but are not limited to, the microporous ultra high density polyethylene membrane sold under the trade designation MPLC from Millipore (Bedford, Mass.), and the microporous Nylon 6,6 membrane sold under the designation 045ZY by Cuno Incorporated (Meriden, Conn.).

Selective transmission films are films that are neither perforated nor porous, but instead transfer gases through the polymer structure of the film. Selective transmission films are multilayered or mixed polymer materials, where the layers and the polymers are chosen for controlled transmission of gases such as carbon dioxide and oxygen. Selective transmission films are preferred in dry applications because it allows the gas to diffuse out of the envelope, while retaining the initiating agent once released from a frangible pouch. Moreover, the selective transmission film increases the stability of the apparatus prior to its use because it does not easily allow ambient water to diffuse into the apparatus, which could prematurely initiate the reactants.

Generally, a film that has a high carbon dioxide transmission rate is preferred. While not wishing to be bound to any theory, it is thought that the carbon dioxide transmission rate approximates the chlorine dioxide transmission rate because chlorine dioxide and carbon dioxide are about the same size. Preferably, the selective transmissive film has a selective gas transmission rate of between about 500 cc/m$^2$/24 hrs and about 30,000 cc/m$^2$/24 hrs for $CO_2$ and between about 1,000 cc/m$^2$/24 hrs and about 10,000 cc/m$^2$/24 hrs for $O_2$. More preferably, the envelope is constructed of a material having a selective gas transmission rate of between about 1,000 cc/m$^2$/24 hrs and about 25,000 cc/m$^2$/24 hrs for $CO_2$ and between about 2,000 cc/m$^2$/24 hrs and about 10,000 cc/m$^2$/24 hrs for $O_2$. Most preferably, the envelope is constructed of a material having a selective gas transmission rate of between about 5,000 cc/m$^2$/24 hrs and about 25,000 cc/m$^2$/24 hrs for $CO_2$ and between about 3,000 cc/m$^2$/24 hrs and about 10,000 cc/m$^2$/24 hrs for $O_2$. Measurement of selective gas transmission rate is routine and well known in the art. One suitable selective transmission film is a multilayered polymer film having a carbon dioxide transmission rate of 21,000 cc/m$^2$/24 hrs and an oxygen transmission rate of 7,000 cc/m$^2$/24 hrs sold under the trade designation PD-961 Cryovac® selective transmission film from Sealed Air Corporation (Duncan, S.C.).

Figure 6:
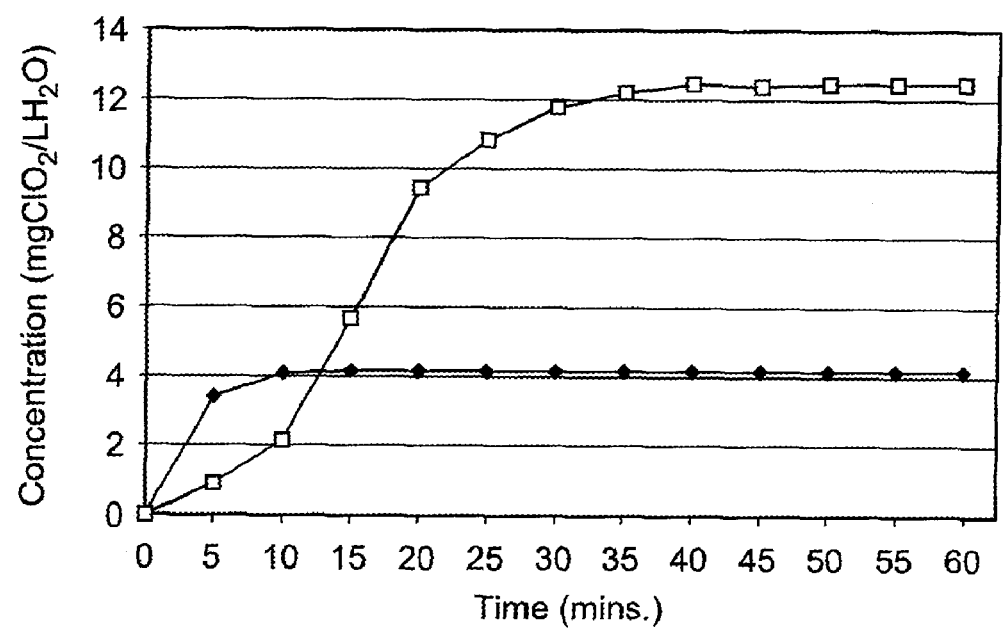
FIG. 6 is a graph depicting gas concentration versus time comparing exemplary apparatus fabricated with and without an envelope.

FIG. 6 is a graph depicting gas concentration versus time comparing various apparatus fabricated with and without an envelope. The square-shaped data points correspond to an apparatus with an envelope constructed with perforated film sold under the trade designation SM60 by Sealed Air Corporation (Duncan, S.C.). As described above, this perforated film has 8 holes per square inch having a diameter of 0.4 mm, a 0.2% perforated area and a water vapor transmission rate of 65 g/m$^2$/24 hrs. The diamond-shaped data points correspond to an apparatus without an envelope. Both apparatus contain 50 mg sodium chlorite and 200 mg citric acid. Both include a sachet constructed from an extruded polypropylene hydrophilic membrane having a 0.65 micron pore size, sold under the trade designation JOTD obtained from Millipore (Bedford, Mass.). For both apparatus, the sachet volume was about 5.5 times the volume of the reactants. Both apparatus were each immersed in 1 liter of water and the chlorine dioxide concentration measured every 5 minutes for an hour., FIG. 6 demonstrates that the inclusion of an envelope increases the reaction efficiency, and consequently, the amount of gas delivered for the same amount and ratio of reactant is greatly increased. In FIG. 6, the apparatus delivers about 12.5 mg of chlorine dioxide gas compared to the approximately 4 mg delivered by the apparatus without an envelope. Thus, the apparatus with the envelope delivered more than 3 times the chlorine dioxide delivered by the apparatus without it, both apparatus having the same amount and ratio of reactant and the same sachet layer. Moreover, FIG. 6 demonstrates the envelope increased the length of time in which gas was generated by about 25 minutes. Of course, there may be instances where having only a sachet, i.e., no envelope, may be advantageous. For example, where the performance of the apparatus without an envelope is sufficient, having only a sachet may be preferred because production is simplified, as the step of constructing the envelope is eliminated, and also because material costs may be decreased by eliminating the need to provide envelope layers to construct the envelope.

Figure 7:
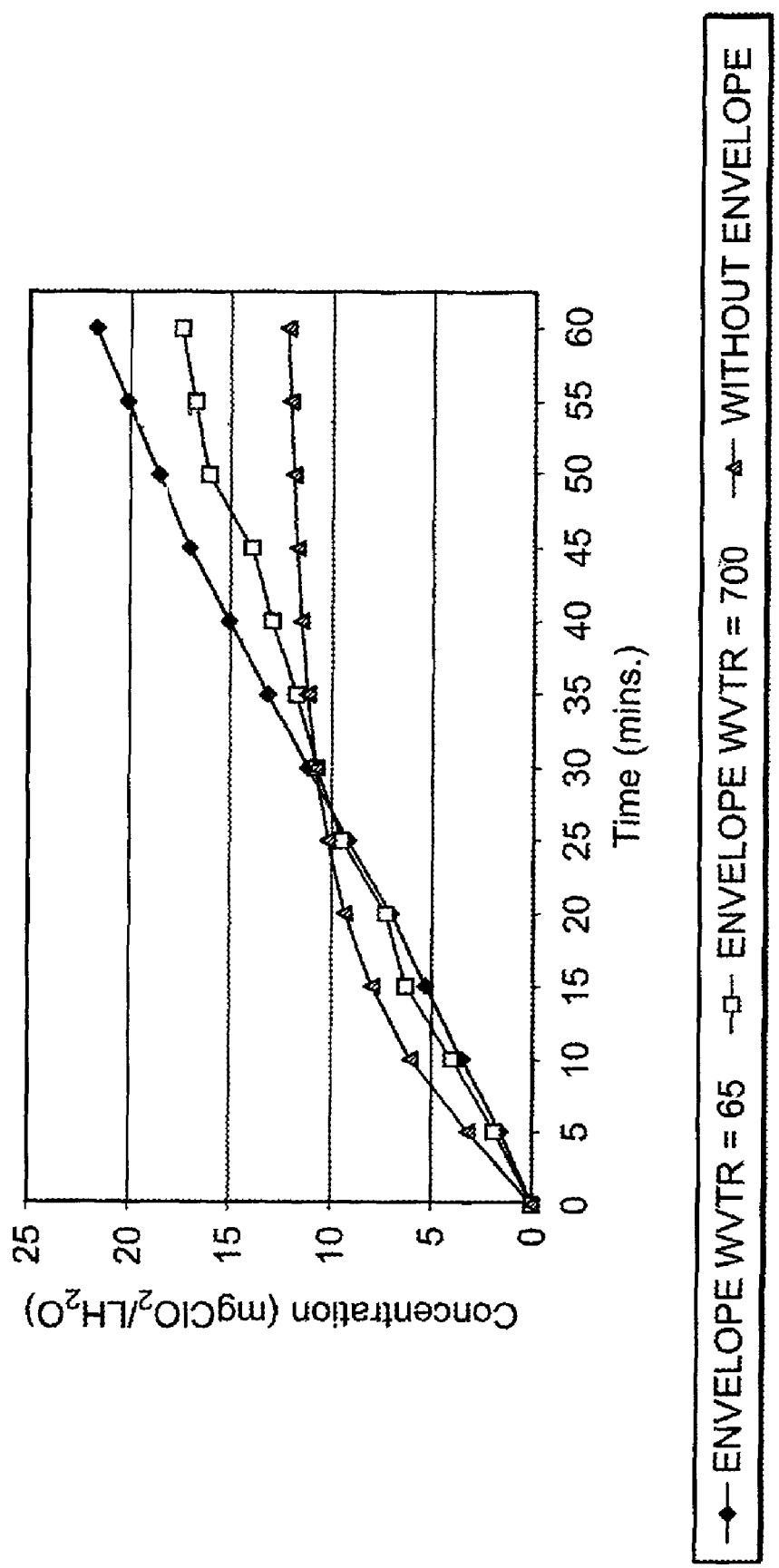
FIG. 7 is a graph depicting gas concentration versus time comparing exemplary apparatus fabricated with envelope materials having different vapor transmission rates.

FIG. 7 is a graph depicting gas concentration versus time comparing exemplary apparatus fabricated with envelope materials having different water vapor transmission rates. The triangular-shaped data points correspond to an apparatus without an envelope. The square-shaped data points correspond to an apparatus with an envelope constructed from perforated film sold under the trade designation SM700 by Sealed Air Corporation (Duncan, S.C.) having 330 holes per square inch having a diameter of 0.4 mm, a 6.4% perforated area and a water vapor transmission rate (WVTR) of 700 g/m$^2$/24 hrs. The diamond-shaped data points correspond to an apparatus with an envelope constructed with perforated film sold under the designation SM60 by Sealed Air Corporation (Duncan, S.C.) having 8 holes per square inch having a diameter of 0.4 mm, a 0.2% perforated area and a water vapor transmission rate of 65 g/m$^2$/24 hrs. All three apparatus contain the same reactant and amount and ratio of reactant as used for the apparatus in FIG. 6. For all three apparatus, the sachet volume was about 5.5 times the volume of the reactants. The reactants were enclosed sachets constructed from 0.65 micron pore size, hydrophobic, non-woven polypropylene material sold under the trade designation ANO6 by Millipore (Bedford, Mass.). These apparatus also were each immersed in 1 liter of water and the chlorine dioxide concentration measured every 5 minutes for an hour.

FIG. 7 demonstrates the effect of the water vapor transmission rate of the envelope on the rate and efficiency of the reaction. In FIG. 7, the apparatus having no envelope has a greater rate of reaction for about the first 15 minutes, but is less efficient than the apparatus with envelopes, delivering only about 12 mg of chlorine dioxide. The apparatus having envelopes exhibit greater efficiency and a longer rate of gas generation, which is proportional to the water vapor transmission rate (WVTR). The envelope with a water vapor transmission rate of 65 g/m$^2$/24 hrs has the greatest efficiency at about 55 minutes, generating about 22 mg of chlorine dioxide at a rate of about 5.5 mg of chlorine dioxide every 15 minutes. The envelope with a transmission rate of 700 g/m$^2$/24 hrs generates about 18 mg of chlorine dioxide in about 55 minutes at a rate of about 4.5 mg of chlorine dioxide every 15 minutes. Thus, for applications where it is desired to increase efficiency and to generate gas over an increased period of time, an envelope with a low vapor transmission rate is preferred. As mentioned above, however, there may be may be applications where having a less efficient apparatus may be advantageous, e.g., decreased material and/or production costs.

By increasing or decreasing the water vapor transmission rate, the practitioner can control the rate and efficiency of the reaction to suit the application. For example, it has been found that an apparatus having a hydrophobic polypropylene envelope with a pore size of 0.1 micron, a 0.65 micron pore size hydrophilic polypropylene sachet, and reactants that include 500 mg sodium chlorite and 2000 mg citric acid, will generate 3.5 mg chlorine dioxide gas per hour for at least 30 hours.

It has been discovered that the use of a sachet can be used to limit the diffusion of the initiating agent into the sachet, and limit the diffusion of reactant and reactant by-products out of the sachet. As a consequence, the reactants are and remain concentrated within the sachet and the pH remains localized increasing the efficiency of the reaction. Various attributes of the sachet, such as pore size, bubble point, and hydrophobic and/or hydrophilic nature of the sachet membrane, can be manipulated to control the affect of the sachet on the reaction as is described below.

The sachet preferably is constructed of a material that is durable and stable. Preferably, it also is capable of fusing to a like material upon the application of heat or ultrasonics for construction purposes, e.g., so that two pieces of such material can be fused about its perimeter to form the sachet.

Envelopes and sachets of the present invention can be sealed about their perimeter by any known method, such as heat sealing, ultrasonic sealing, radio frequency sealing, and sealing with adhesives. A preferred method of forming envelopes and sachets is to use an impulse sealer, which delivers a rapid and discreet thermal pulse to the layers. One impulse sealer suitable for use in accordance with the present invention is the 16" TISH400 Impulse Sealer available from TEW Electric Heating Equipment Corporation (Taiwan).

The sachet layers used to construct the sachet can be chosen to control the diffusion of the reactants out of the sachet, control the rate of gas release from the sachet and control the initiation of the reactants. For example, a hydrophilic sachet will increase the rate at which water and/or water vapor diffuses into the sachet, and the pore size and thickness of the sachet layer also will effect the passage of water, reactants and gas through the sachet layer.

The sachet can be constructed of various materials, including polymeric material or coated papers. It can be constructed from woven material, non-woven membrane, extruded membrane, or any other material with a controlled pore distribution having a mean pore size between about 0.01 μm and about 50 μm.

A woven material is any material woven from cotton, metal, polymer threads, metal threads or the like into a cloth or mesh. Extruded membranes, which include cast membranes, are preferred, and include 0.65 micron pore size, 230 to 260 micron thick, hydrophilic polyethylene membrane sold under the trade designation MPLC from Millipore (Bedford, Mass.), 0.65 micron pore size, extruded hydrophobic polyethylene material sold under the trade designation DOHP by Millipore (Bedford, Mass.). Also preferred is the cast membrane 3 micron pore Nylon 6,6 material sold under the trade designation BIODYNE A by Pall (Port Washington, N.Y.). Non-woven membranes are membranes formed from materials such as cellulose or polymers. Other cast membranes include 0.45 pore, hydrophilic Nylon 6,6 membranes with a polypropylene backbone sold under the designation BA05 by Cuno Incorporated (Meriden, Conn.); 0.45 pore, hydrophilic polypropylene membrane available from 3M (City, State); and 0.45 pore size, 180 to 240 micron thick, hydrophilic Nylon 6,6 membranes sold under the designations 045ZY and 045ZN by Cuno Incorporated (Meriden, Conn.). Also suitable are hydrophobic, liquid water permeable non-woven polyethylenes, such as the TYVEK® 1025D polyethylene material from DuPont Company (Wilmington, Del.).

Also suitable for use in constructing the sachet are composite layers, including, but not limited to, starch/polymer composite layers. One currently preferred composite layer is a hydrophilic, 114 μm thick, non-woven rice starch/polyethylene composite sold under the designation 60MDP-P by Mishima Paper Company, Limited (Japan). This layer is heat sealable and wets easily. Furthermore, this layer does not merely keep the reactants apart until initiation, but functions like other preferred sachet layers of the present invention in that it controls the rate diffusion of reactants out of the sachet, controls the rate of gas release from the sachet, and controls the initiation of the reactant so that the reactant remains concentrated within the sachet and the reaction is driven to completion.

Non-woven membranes can be formed, e.g., by suspending the membrane material, e.g., cellulose fibers, in a liquid over a porous web and then draining the liquid to form a membrane. Non-woven membranes typically have a relatively narrow and consistent pore size distribution as compared to woven materials. Consequently, the non-woven sachet generally allows less initiating agent into the sachet than the woven sachet having the same pore size because, generally the pore size distribution is narrower. A non-woven membrane suitable for use in accordance with the present invention is the 0.65 micron pore size, hydrophobic, non-woven polypropylene material sold under the trade designation ANO6 by Millipore (Bedford, Mass.).

In a preferred embodiment the sachet is constructed from a membrane having a pore size between about 0.01 μm and about 50 μm. More preferably, the pore size is between about 0.05 μm and about 40 μm, and most preferably, the pore size is between about 0.10 μm and 30 μm. The pore size of the sachet is measured by bubble point. Bubble point is a measurement well known in the art which approximates pore size from a measurement of the pressure necessary to drive a bubble of gas through the membrane. Pore size affects the rate at which water and ions can diffuse through the sachet in both directions. A pore size preferably is chosen that allows entry of initiating agent into the sachet and, at the same time, retains the reactants within the sachet at a high concentration so that the reaction rate is increased and a high efficiency maintained. The artisan can readily identify suitable equivalents of any of the foregoing by exercising routine experimentation.

Preferably, the sachet is constructed from a membrane having a thickness between about 50 microns and 500 microns, more preferably between about 100 microns and 400 microns, and most preferably between about 150 microns and 300 microns.

In certain preferred embodiments, the material used to construct the sachet preferably has a bubble point between about 3 psi and about 100 psi, more preferably between about 5 psi and about 80 psi, and most preferably between about 10 psi and about 70 psi. As mentioned previously, the measurement of bubble point is routine and well known in the art and typically is supplied by suppliers of membranes, films, etc., however, the practitioner can readily make measurement.

Additionally, the sachet can be constructed from material that is hydrophobic and/or hydrophilic. It can also comprise a material having one or more hydrophilic zones and one or more hydrophobic zones. These zones can be created, e.g., by printing a functional chemical group or polymer onto a surface of the sachet that is hydrophilic or hydrophobic or charged to create one or more hydrophilic or hydrophobic or charged zones. For example, a sulfonic acid group can be disposed on the surface of the polypropylene membrane, creating zones that are both hydrophilic and negatively charged ($R-SO_2^-$). The membrane can then washed with a dilute acid such that the ion exchange groups ($R-SO_2^-$) bind the $H^+$ ions. These $H^+$ ions can later be released to supply $H^+$ ions to acid activate reactant, e.g., chlorite, as a replacement or supplement to acid reactant.

When the sachet is constructed of hydrophobic material, the hydrophobic material preferably has a flow time between about 10 sec/500 ml and about 3,500 sec/500 ml for 100% IPA at 14.2 psi. More preferably, the material has a flow time between about 60 sec/500 ml and about 2,500 sec/500 ml for 100% IPA at 14.2 psi, and most preferably, the material has a flow time between about 120 sec/500 ml and about 1,500 sec/500 ml for 100% IPA at 14.2 psi.

When the sachet is constructed of hydrophilic material as described above the hydrophilic material preferably has a flow time between about 5 sec/500 ml and about 800 sec/500 ml for 100% IPA at 14.2 psi. More preferably, the material has a flow time between about 20 sec/500 ml and about 400 sec/500 ml for 100% IPA at 14.2 psi, and most preferably, the material has a flow time between about 50 sec/500 ml and about 300 sec/500 ml for 100% IPA at 14.2 psi. Measurement of flow time is routine and well known in the art.

Yet another alternative embodiment uses a material to construct the sachet that has a first surface that is hydrophilic and a second surface that is hydrophobic. For example, a sachet can be constructed from such a material such that the hydrophilic surface is on the outside of the sachet and the hydrophobic surface is on the inside of the sachet. The exterior, hydrophilic surface aids the initiation of the reaction since water will readily wet a hydrophilic surface and enter the sachet. However, once inside the sachet, the hydrophobic, interior surface limits water passage out of the sachet. This keeps the reactants concentrated within the sachet while allowing the gas to escape thus exploiting the advantages of the discoveries disclosed herein. One such material suitable for use in the present invention is a non-woven membrane 0.65 micron pore size diameter formed from a hydrophobic material, such as polypropylene, that has been chemically functionalized with amines and carboxyl groups to produce a charge, hydrophilic surface.

The ratio of sachet volume to reactant volume also can be manipulated to control the concentration of the reactants, intermediates, by-products, etc. within the sachet. As discussed previously, increasing the concentration of reactants generally increases reaction efficiency. Preferably the sachet volume is less than about 20 times the volume of reactant, more preferably less than about 10 times the volume of the reactant. Most preferably, it is less than 6 times the volume of the reactants. Smaller volumes are preferred in certain applications because when the ratio of sachet volume to reactant volume is small, water produced in the reaction increases the pressure inside the sachet reducing the rate at which water can diffuse into the sachet, the water to reactant ratio remains constant and thus the rate of reaction remains constant. Preferably the volume of the envelope is from about 2 to about 6 times the volume of the sachet.

Figure 8:
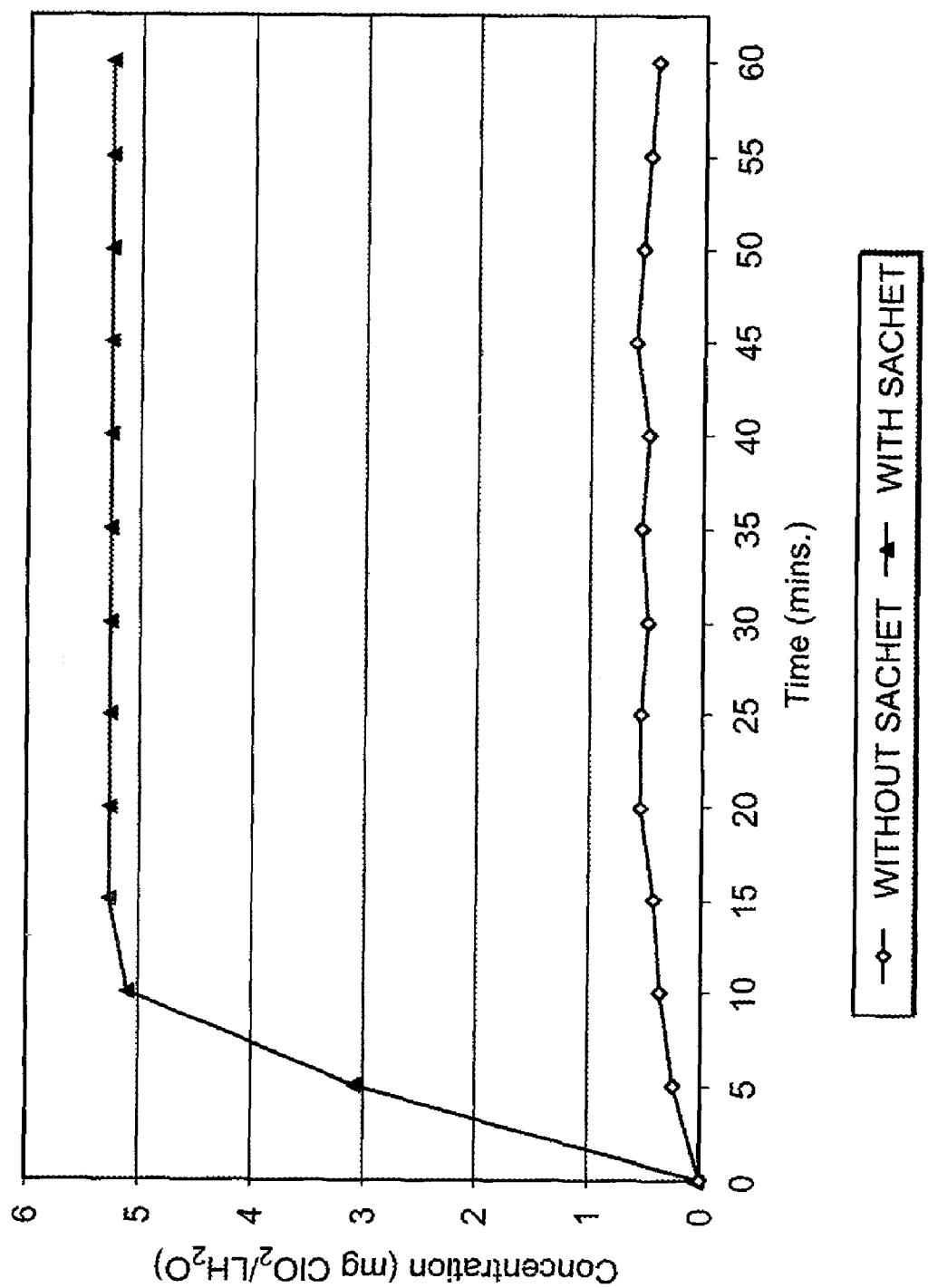
FIG. 8 is a graph depicting gas concentration versus time comparing exemplary apparatus fabricated with and without a sachet.

FIG. 8 is a graph depicting gas concentration versus time comparing exemplary apparatus fabricated with and without a sachet. Specifically, FIG. 8 depicts gas concentration versus time comparing delivery of chlorine dioxide gas from reactant within a sachet versus reactant added directly to water, i.e., with neither sachet nor envelope. The triangular-shaped data points indicate the rate of delivery of chlorine dioxide over time in 1 liter of water from a sachet material constructed from a 0.65 micron pore size, hydrophilic polyethylene membrane sold under the trade designation MPLC by Millipore (Bedford, Mass.). The sachet contained 200 mg citric acid and 50 mg of sodium chlorite. The sachet volume was about 5.5 times the volume of the reactants. The sachet was enclosed in an envelope constructed from perforated film sold under the trade designation SM700 by Sealed Air Corporation having 330 holes per square inch having a diameter of 0.4 mm, a 6.4% perforated area and a water vapor transmission rate of 700 g/m$^2$/24 hrs. The diamond-shaped data points indicate the rate of delivery of chlorine dioxide over time when the same reactants in the same amounts were added to 1 liter of water directly, i.e., with neither sachet nor envelope. The apparatus with the sachet delivered more than 10 times the chlorine dioxide than when the reactants were added directly to the water. As can be seen from FIG. 8, the sachet increases the efficiency of the reaction.

Figure 9:
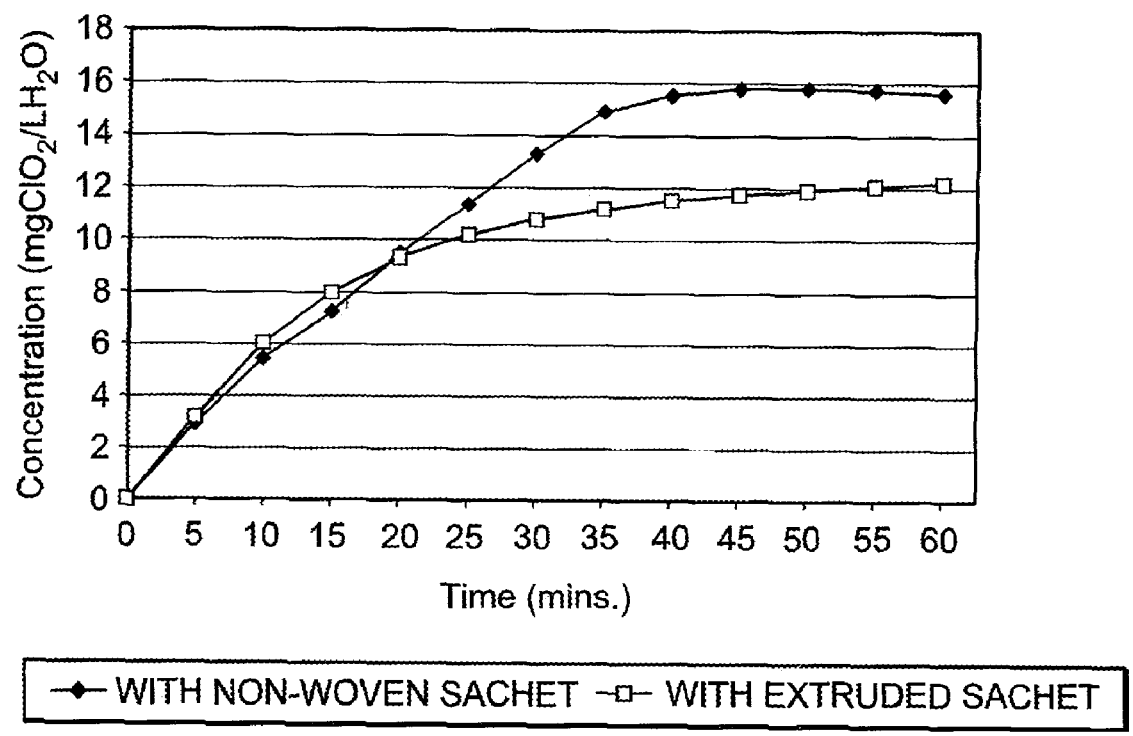
FIG. 9 is a graph depicting gas concentration versus time comparing exemplary apparatus fabricated with extruded and woven sachets.

FIG. 9 is a graph depicting gas concentration versus time comparing an exemplary apparatus fabricated with extruded and non-woven sachets. The diamond-shaped data points indicate delivery of chorine dioxide over time for the apparatus with a sachet constructed from 0.65 micron pore size, hydrophobic, non-woven polypropylene material sold under the trade designation ANO6 by Millipore (Bedford, Mass.). The square-shaped data points indicate delivery of chorine dioxide over time for the apparatus with a sachet constructed from 0.65 micron pore size, extruded hydrophobic polypropylene material sold under the trade designation DOHP by Millipore (Bedford, Mass.). Both sachets contained 200 mg citric acid and 50 mg of sodium chlorite and the sachet volume was about 5.5 times the volume of the reactants. Neither apparatus included an envelope. The apparatus were each immersed in 1 liter of water and the chlorine dioxide gas concentration measured every five minutes for an hour.

As shown in FIG. 9, both apparatus deliver chlorine dioxide at approximately the same rate for about the first 20 minutes. However, as the reactants become increasingly dilute in the extruded sachet relative to the non-woven sachet, the rate of the chlorine dioxide release diminishes. The efficiency of the reaction in the apparatus with the non-woven sachet is greater than that with the extruded sachet. The apparatus with the non-woven sachet also continue to generate chlorine dioxide gas at a rate of about 2 mg every 5 minutes for about 15 minutes longer than the apparatus with the extruded sachet. As mentioned above, non-woven sachets generally have a relatively narrow pore size distribution, and without wishing to be bound to any theory, it is thought that this accounts for the greater efficiency and longer period of gas generation. Thus, FIG. 9 provides a non-limiting illustration of how sachet material choice, and thus reactant concentration, can be exploited to sustain the rate of gas release and increase the efficiency.

Figure 10:
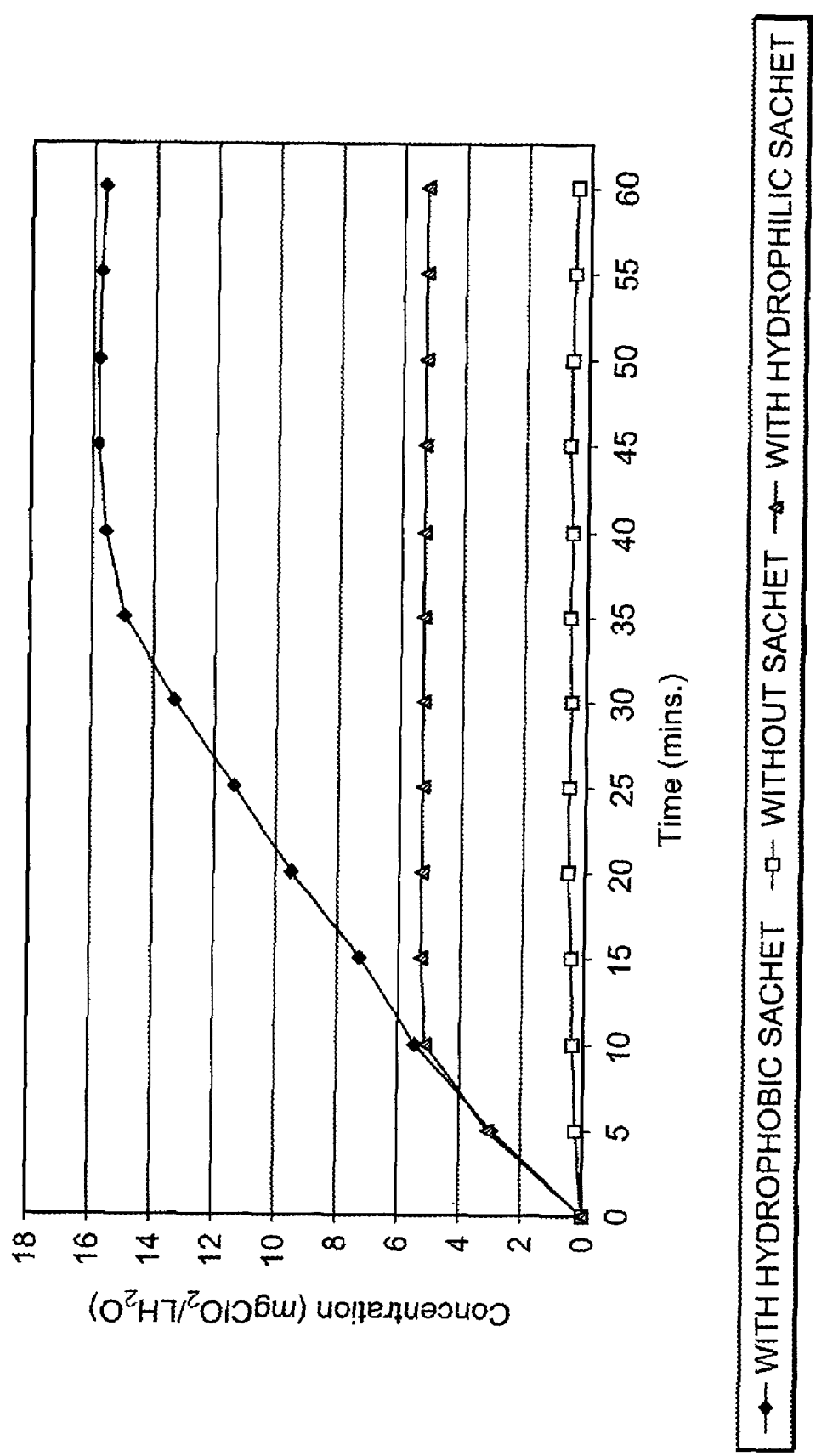
FIG. 10 is a graph depicting gas generation versus time comparing exemplary apparatus fabricated with sachets made of materials having hydrophobic and hydrophilic surfaces.

FIG. 10 is a graph depicting gas generation versus time comparing exemplary apparatus fabricated with sachets made of materials having hydrophobic and hydrophilic surfaces. The triangular-shaped data points correspond to an apparatus with a sachet constructed from 0.65 micron pore size, hydrophilic polyethylene sachet sold under the trade designation MPLC from Millipore (Bedford, Mass.). The diamond-shaped data points correspond to an apparatus with a sachet constructed from 0.65 micron pore size, extruded hydrophobic polypropylene material sold under the trade designation DOHP by Millipore (Bedford, Mass.). The square-shaped data points correspond to adding the reactant directly to the water. The reactant was 200 mg citric acid and 50 mg of sodium chlorite and the sachet volume was about 5.5 times the volume of the reactants. Neither sachet was enclosed in an envelope. The apparatus and the reactant were each immersed in 1 liter of water and the chlorine dioxide gas concentration was measured every 5 minutes for an hour.

FIG. 10 demonstrates that apparatus having a hydrophobic sachet results in a more efficient reaction that generates gas over a longer period of time than a hydrophilic sachet. In FIG. 10, the apparatus with the hydrophobic sachet generated chlorine dioxide for about 30 minutes at about 2 mg every 5 minutes. In contrast, the apparatus with the hydrophilic sachet generated chlorine dioxide only for about 10 minutes at about 2 mg every 5 minutes. As disclosed above in connection with FIG. 6, adding an envelope to either sachet will have the effect of increasing the efficiency of the reaction as well as increasing the length of time in which gas is generated.

The reactant preferably comprises an aqueous soluble acid and a reactant that upon acid activation generates a gas. For example, for the generation of chlorine dioxide, preferably the reactant comprises an aqueous soluble acid and an aqueous soluble chlorite. For the generation of sulfur dioxide, preferably the reactant comprises an aqueous soluble acid and an aqueous soluble sulfite. Other examples of gas generating reactions are disclosed above.

Any acid can be used as a reactant. However, weak acids are preferred, as they typically are safer to handle, produce less undesirable by-products, and are less reactive. Also, multifunctional acids are preferred. Multifunctional acids are acids that have more than one reactive site. For example, the trifunctional acid, citric acid, is preferred. Preferably, the aqueous soluble acid is selected from the group consisting of phosphoric acid, fumaric acid, glycolic acid, acetic acid, ascorbic acid, oxalic acid, maleic acid, lactic acid, tartaric acid, citric acid and mixtures thereof. More preferably, the aqueous soluble acid is selected from the group consisting of ascorbic acid, phosphoric acid, oxalic acid, maleic acid, lactic acid, tartaric acid, citric acid and mixtures thereof. Most preferably, the aqueous soluble acid is ascorbic acid, oxalic acid, citric acid and mixtures thereof.

For applications involving the generation of chlorine dioxide, preferably the aqueous soluble chlorite is selected from a group consisting of sodium chlorite and potassium chlorite and mixtures thereof. Preferably sodium chlorite is used.

Preferably, the weight ratio of the aqueous soluble chlorite to the aqueous soluble acid is between about 1:2 to about 1:6, preferably from about 1:2.5 to about 1:5, most preferably from about 1:3 to about 1:4.5. Preferably, a pH between about 1.5 to 5.5, more preferably a pH of about 2, is maintained by using an excess of acid. Because the reactants are concentrated within the sachet, less acid is needed to drive the reaction to completion and the pH remains low because the acid is concentrated. Furthermore, chlorite is consumed by acid and therefore the presence of chlorite is minimized.

Figure 11:
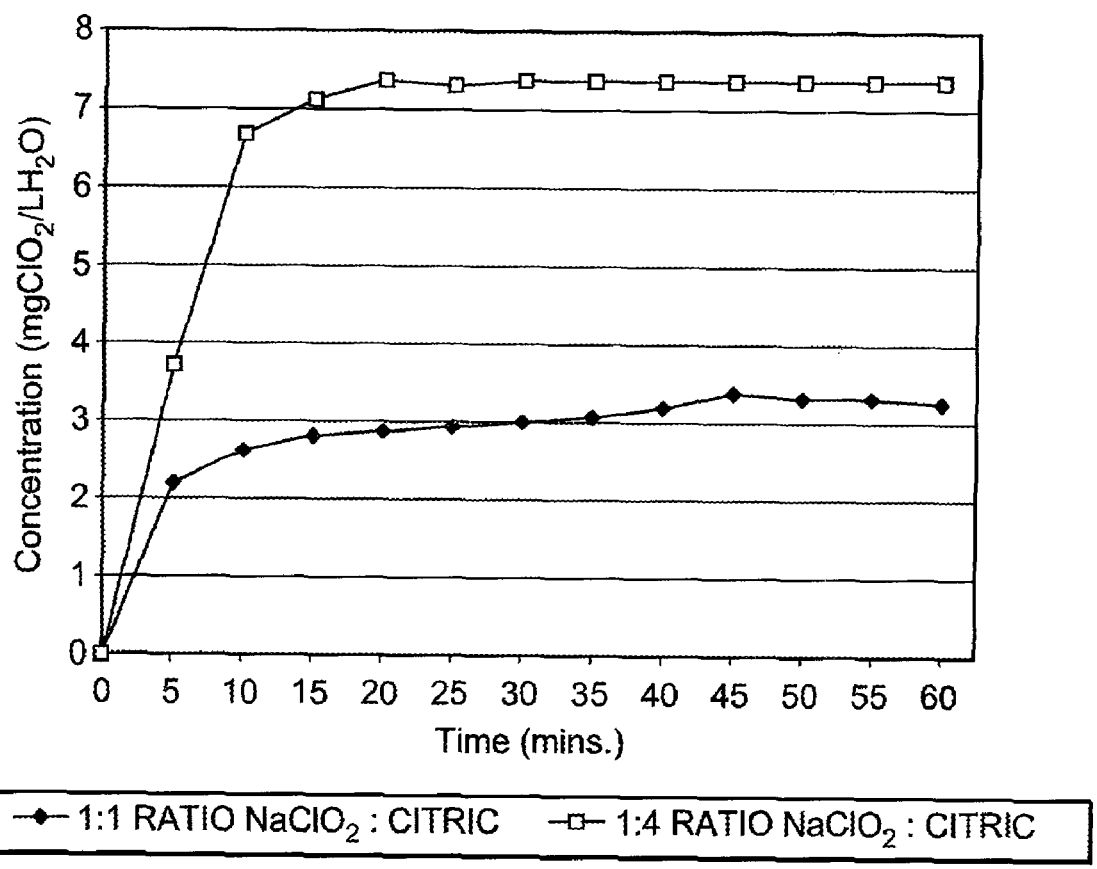
FIG. 11 is a graph depicting gas concentration versus time comparing exemplary apparatus fabricated with different reactant ratios.

FIG. 11 is a graph depicting gas concentration versus time comparing Apparatus fabricated with two different reactant ratios. The square-shaped data points correspond to an apparatus with a 1:4 ratio of citric acid to sodium chlorite (50 mg sodium chlorite and 200 mg of citric acid). The diamond-shaped data points correspond to an apparatus with a 1:1 ratio of citric acid to sodium chlorite (50 mg sodium chlorite and 50 mg citric acid). Both apparatus included a sachet constructed from 0.65 micron pore size, hydrophilic, polyethylene sachet sold under the trade designation MPLC from Millipore (Bedford, Mass.). The sachet volume was about 5.5 times the volume of the reactants. Both sachets were enclosed in an envelope constructed from perforated film sold under the trade designation SM700 by Sealed Air Corporation having 330 holes per square inch having a diameter of 0.4 mm, a 6.4% perforated area and a water vapor transmission rate of 700 g/m$^2$/24 hrs. These apparatus were immersed in 1 liter of water and the chlorine dioxide gas concentration measured every 5 minutes for an hour.

FIG. 11 demonstrates that increasing the amount of citric acid relative to the amount of sodium chlorite increases the efficiency of the reaction, in part because the excess of acid drives the reaction to completion. The relationship of efficiency to reactant ratio is fairly predictable when the ratio of sodium chlorite to citric acid is between about 1:1 and about 1:6. Above about 1:6, there is little change in the efficiency of the reaction.

Ambient temperature also can affect the efficiency of the reaction. Generally, the hotter the temperature of the ambient fluid, e.g., water or air, the more efficient the generation of gas. Generally, however between the ranges of 10° C. and 40° C., the efficiency improves as the temperature increases. The data used to generate FIGS. 6 through 11 and the Examples are from apparatus tested at from about 23° C. to about 25° C. The sachet also can include various other ingredients that will be obvious to one skilled in the art, such as drying agents, stabilizers, and buffers to control the pH.

It also should be understood that the apparatus and methods of the present invention also are readily applicable to the delivery of more than one gas at one time. For example, the reactant can include both a chlorite and at sulfite for the delivery of both chlorine dioxide and sulfur dioxide.

Figure 2A:
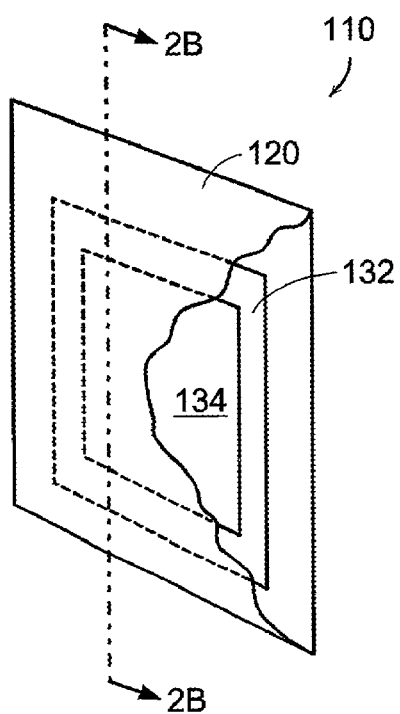
FIGS. 2A and 2B are a perspective view and a cross-sectional side view, respectively, of another embodiment of an apparatus constructed in accordance with the present invention.
Figure 2B:
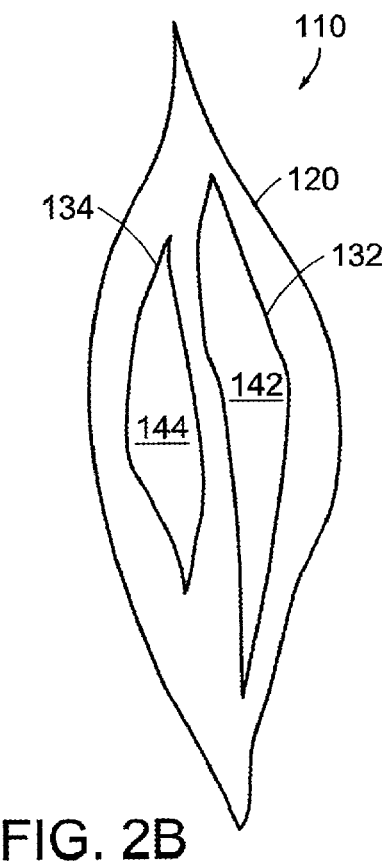

FIGS. 2A and 2B are a perspective view and a cross-sectional side view, respectively, of another embodiment of an apparatus 110 constructed in accordance with the present invention. In general overview, apparatus 110 includes envelope 120 and two sachets 132, 134 disposed within the envelope 120. Sachets 132, 134 contain reactant 142, 144, respectively.

Apparatus 110 is particularly useful for the delivery of gas in wet applications. In such applications, reactant 142, 144 can be, e.g., sodium chlorite and acid respectively, the sachet can be constructed from a material with a pore size large enough to allow diffusion of sodium chlorite and acid reactant out of the sachets, and the envelope can be chosen that does not allow the reactants to diffuse from the apparatus and regulates the release of gas from the apparatus so that the reaction remains efficient.

The envelope and sachet can be constructed from any of the material discussed in references to FIGS. 1A and 1B. Preferably, the envelope is a hydrophobic perforated film, such as the polypropylene copolymer film sold under the designation SM700 by Sealed Air Corporation (Duncan, S.C.) having 330 holes per square inch having a diameter of 0.4 mm, a 6.4% perforated area and a water vapor transmission rate of 700 g/m$^2$/24 hr. The envelope can also be constructed from 0.65 micron pore hydrophobic polypropylene membrane, such as that sold under the trade designation DOHP by Millipore (Bedford, Mass.).

For wet applications, most preferably the envelope is constructed from a cast membrane. Suitable cast membranes can be chosen to regulate the entry of initiating agent into the apparatus based on the thickness of the layer, the pore size and the hydrophobic and/or hydrophilic nature of the membrane. The thickness of the membrane is preferably between about 50 microns and about 500 microns, more preferably between about 100 microns and about 400 microns, and most preferably between about 150 microns to about 350 microns. The pore size preferably is between about 0.05 microns to about 5 microns, more preferably between about 0.2 microns and about 1.2 microns, most preferably between about 0.48 microns and 0.85 microns. A non-woven membrane suitable for use in accordance with the present invention is the 0.60 pore size, hydrophobic, polypropylene membrane having a thickness between about 250 microns and about 300 microns sold under the designation 060P1 by Cuno Incorporated (Meriden, Conn.).

Sachets 132, 134 can be constructed from hydrophobic membrane and/or hydrophilic membrane. Preferred materials for sachets 132, 134 are described in connection with the embodiment of FIGS. 1A and 1B. Preferably, the sachets 132, 134 are constructed from a hydrophilic material, e.g., 0.65 micron pore size hydrophilic polyethylene membrane, such as that sold under the designation MPLC by Millipore (Bedford, Mass.), or extruded polypropylene hydrophilic membrane having a 0.65 micron pore size, sold under the trade designation JOTD obtained from Millipore (Bedford, Mass.), or a 114 μm thick, non-woven rice starch polyethylene composite sold under the designation 60MDP-P by Mishima Paper Company, Limited (Japan). Also preferred are the 1.2 micron and 2 micron pore, hydrophilic Nylon 6,6 membranes sold under the designations 120ZY and 200ZY, respectively, by Cuno Incorporated (Meriden, Conn.), and the 1.2 and 2.0 micron pore size, hydrophilic polyethylene membranes sold under the designation MPLC by Millipore (Bedford, Mass.).

For wet applications, the pore size of the sachet membrane preferably is between about 0.01 microns to about 30 microns, more preferably between about 0.05 microns and about 20 microns, even more preferably between about 0.1 microns and about 10 microns, most preferably between about 1.2 microns and 5 microns. A pore size of between about 1.2 microns and 5 microns is preferred in certain embodiments. Without wishing to be confined to any particular theory, it is believed that sachet layers with pore sized in the most preferred range allow rapid passage of the initiating agent into the reactant and diffusion of the reactant into the envelope. The envelope would then be chosen with a pore size that does not allow significant diffusion of the reactant out of the apparatus. The thickness of the sachet membrane preferably is between about 50 microns and about 500 microns, more preferably between about 100 microns and about 400 microns, and most preferably between about 150 microns to about 350 microns.

Reactant 142, 144 preferably includes an aqueous soluble acid and an aqueous chlorite that upon acid activation generates a gas. Preferably, these components are not mixed, but instead are separately contained in sachets 132, 134. It is preferred to separately contain the chlorite and the acid because this minimizes the likelihood of premature initiation, e.g., during storage and shipment. Reactant 142, 144 can be liquid or solid, but is preferably solid.

Preferably the citric acid has a particle size of between about 15 microns and about 55 microns and is desiccated until about 6-8% of the initial weight is removed as excess moisture prior to incorporation into the apparatus of the present invention. Preferably the sodium chlorite has a particle size of between about 15 microns and about 55 microns and is desiccated to remove excess moisture prior to incorporation into the apparatus of the present invention.

In a preferred embodiment, the envelope 120 is hydrophobic and the sachets 132, 134 are hydrophilic. This preferred embodiment is particularly suitable for the delivery of gas in wet applications and has a slower rate of gas delivery than apparatus 10 of FIGS. 1A and 1B. For example, this embodiment can be used to deliver gas at low rates over long periods of time, e.g., 20 mg of gas per hour over a 24 hour period. This embodiment also is preferred for applications where a high efficiency and concentration of gas is desired and it is possible to allow the apparatus a period of time to complete delivery, e.g., 4 to 8 hours. This application also is preferred when working with relatively large amount of reactants that otherwise might begin reacting during construction and storage of the apparatus, e.g., when constructing an apparatus having more than about 1 gram of sodium chlorite and 4 grams of citric acid. This embodiment is particularly useful for controlling and preventing biofilm contamination and as a disinfectant, antiseptic and sanitizer in applications where water is stored or conducted through conduits, e.g., in swimming pools, water tanks, humidifiers, boat lines, beverage lines and the like.

Optionally, this embodiment could contain a second envelope (not shown) enclosing the first envelope 120. This second envelope might be useful, for example, in further regulating the introduction of the initiating agent through the envelope walls.

Optionally, this embodiment could contain a third sachet as depicted in FIG. 19, which is a cross sectional side view of apparatus 1210 constructed in accordance with the present invention. Apparatus 1210 generally includes envelope 1220, and sachets 1232, 1234 and 1236, disposed within envelope 1220. Sachets 1232, 1234 and 1236 contain reactant 1242, 1244, and 1246, respectively. This embodiment is particularly useful, for example, when it is desired to separate acid and chlorite into separate sachets and the volume of one is significantly greater than the other, e.g., the volume of acid is greater than the volume of chlorite. In this instance, one can separate the acid 1242 and 1246, into two sachets 1232, 1236 that are disposed on each side of the chlorite 1244 disposed within sachet 1234. This embodiment is preferred when using larger amounts of reactant, e.g., one could construct an apparatus similar to that depicted in FIG. 19, with 2 grams of sodium chlorite in one sachet, disposed between two sachets with 4-5 grams of citric acid in each. All other variables being equal, this embodiment is more efficient than embodiments having only two sachets when working with larger amounts of reactant. This embodiment also is easier to manufacture.

In a currently preferred embodiment, the reactant includes citric acid disposed in sachets 1232, 1236 and sodium chlorite is disposed in sachet 1234. The sachets 1232, 1234, 1236 are constructed from 114 µm thick, non-woven rice starch polyethylene composite sold under the designation 60MDP-P by Mishima Paper Company, Limited (Japan), and the envelopes are constructed from 0.60 pore size, hydrophobic polypropylene membrane having a thickness between about 250 microns and about 300 microns sold under the designation 060P1 by Cuno Incorporated (Meriden, Conn.).

This embodiment is particularly useful for controlling and preventing contamination and as a disinfectant, antiseptic and sanitizer in applications where water is stored or conducted through conduits, e.g., in swimming pools, water tanks, humidifiers, boat lines, beverage lines and the like.

Figure 3A:
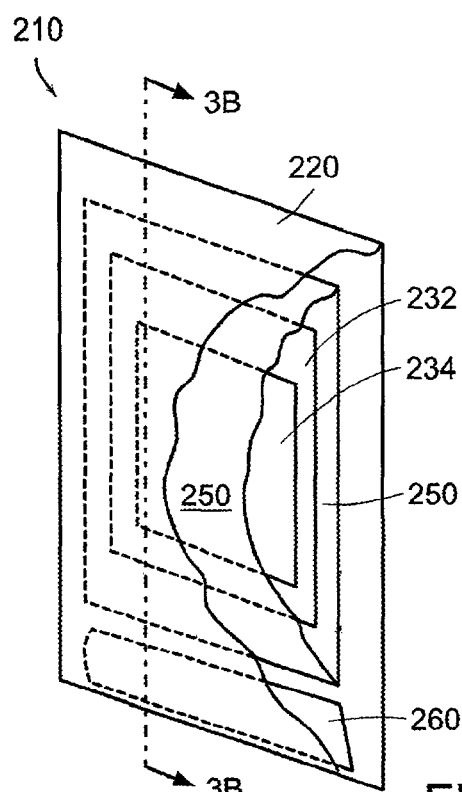
FIGS. 3A and 3B are a perspective view and a cross-sectional side view, respectively, of yet another embodiment of an apparatus constructed in accordance with the present invention.
Figure 3B:
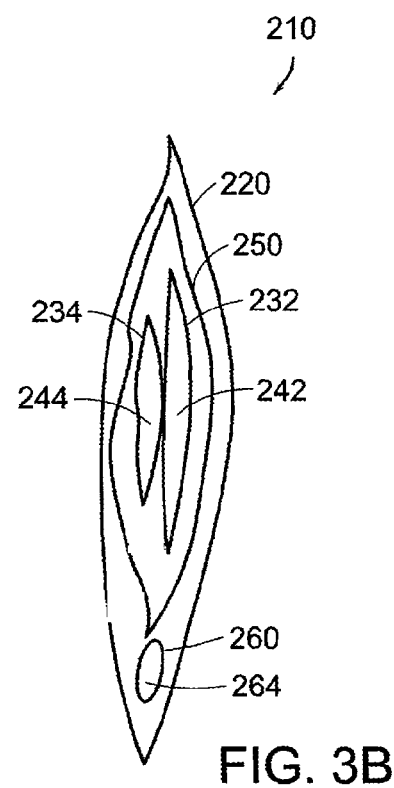

FIGS. 3A and 3B are a perspective view and a cross-sectional side view, respectively, of an apparatus 210 constructed in accordance with the present invention. Apparatus 210 includes first sachet 232, first reactant 242 disposed within first sachet 232, second sachet 234, second reactant 244 disposed within second sachet 234, third sachet 250 disposed about first sachet 232 and second sachet 234, and envelope 220 disposed about third sachet 250. Disposed within the envelope 220 adjacent to the third sachet 250 is frangible pouch 260, and initiating agent 264 disposed within frangible pouch 260.

Apparatus 210 is particularly useful for the delivery of gas in a dry application because initiating agent 264 is contained within the apparatus 210. In this embodiment, first reactant 242 and second reactant 244 generate a gas in the presence of initiating agent 264. For this to occur, frangible pouch 260 is ruptured, e.g., by exerting pressure on frangible pouch 260 so that initiating agent 264 is delivered into first envelope 220. Third sachet 250 allows contact of initiating agent 264 with first sachet 232 and second sachet 242.

First sachet 232, second sachet 234, first reactant 242 and second reactant 244 are described above in reference to the embodiments shown in FIGS. 1A, 1B, 2A and 2B. In a currently preferred embodiment, first sachet 232 and second sachet 234 are constructed from a hydrophilic material having a pore size between about 3 microns and 5 microns. A suitable material is a 3 micron pore Nylon 6,6 material sold under the trade designation BIODYNE A by Pall (Port Washington, N.Y.).

Third sachet 250 preferably is constructed using the materials described above in reference to the sachet material for the embodiments described for FIGS. 2A and 2B. The materials described above in reference to the embodiment described for FIGS. 1A and 1B can also be used. A suitable sachet layers is 0.65 micron pore hydrophobic polypropylene membrane, such as that sold under the trade designation DOHP by Millipore (Bedford, Mass.). The third sachet limits the diffusion of reactant out of the third sachet and thus, it keeps the reactant concentrated within the third sachet and the pH localized. Preferably, the third sachet volume is less than 4 times that of the first reactant and the second reactant combined, and most preferably less than 2 times that of the first reactant and the second reactant combined.

Preferably, envelope 220 is constructed from a selective transmission film. Selective transmission films are described above in connection with FIGS. 1A and 1B. As discussed above, selective transmission films are preferred in dry applications because it allows the gas to diffuse out of the envelope, while retaining the initiating agent once released from the frangible pouch. Moreover, the selective transmission film increases the stability of the apparatus prior to its use because it does not easily allow ambient water to diffuse into the apparatus, which could prematurely initiate the reactants. Furthermore, keeping the reactant, e.g., sodium chlorite and acid, separated into two sachets also can increase the stability of the apparatus because it retards initiation should initiating agent diffuse into the apparatus prior to rupturing the frangible pouch.

One suitable selective transmission film is a multilayered polymer film having a carbon dioxide transmission rate of 21,000 $cc/m^2/24$ hrs and an oxygen transmission rate of 7,000 $cc/m^2/24$ hrs sold under the trade designation PD-961 Cryovac® selective transmission film from Sealed Air Corporation (Duncan, S.C.).

Frangible pouch 260 can be constructed of any material that ruptures when pressure is applied to the envelope thus releasing the initiating agent inside it. Preferably, the frangible pouch is constructed from a multi-layer plastic, e.g., polyolefin, envelope having a weak layer positioned near the sealing surface that will fail under pressure. Initiating agent 264 can be any agent that initiates a gas-generating reaction, e.g., water. Preferably the initiating agent is water or an aqueous solution, but is not limited thereto.

The skilled practitioner will appreciate that the first reactant 242 and the second reactant 244 can be combined and disposed in a single sachet, i.e., first sachet 232 and second sachet 234 can be combined into a single sachet (not shown). Moreover, the initiating agent 264 disposed in frangible pouch 260 can be disposed within the volume defined by the third sachet 250 (also not shown).

Figure 4A:
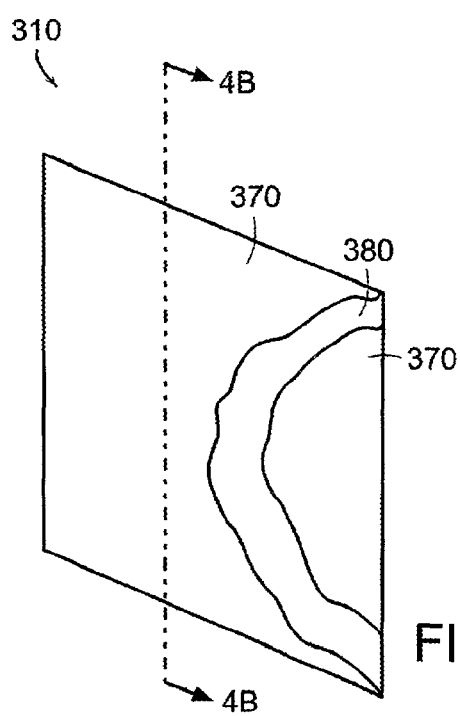
FIGS. 4A and 4B are a perspective view and a cross-sectional side view, respectively, of still yet another embodiment of an apparatus constructed in accordance with the present invention.
Figure 4B:
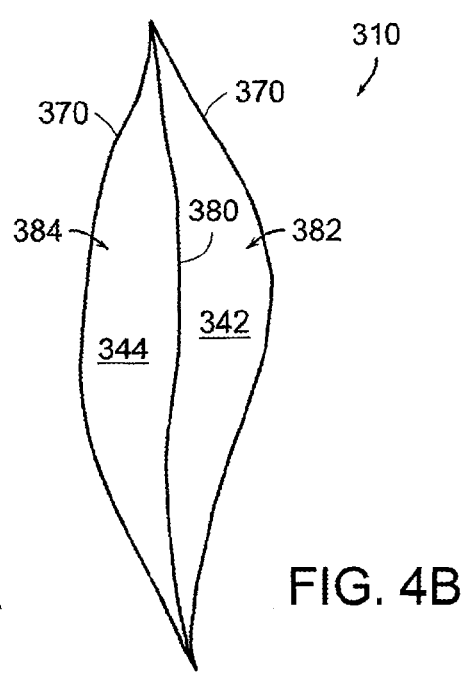

FIGS. 4A and 4B are a perspective view and a cross-sectional side view, respectively, of still yet another embodiment of an apparatus 310 constructed in accordance with the present invention. In general overview, apparatus 310 includes sachet 370 and partition 380 disposed within sachet 370 defining first volume 382 and second volume 384 within sachet 370. Also shown is first reactant 342 disposed within first volume 382 and second reactant 344 disposed within second volume 384. In this embodiment, first reactant 342 and second reactant 344 generate a gas in the presence of an initiating agent, and sachet 370 allows entry of an initiating agent into apparatus 310.

Preferably, sachet 370 is constructed using a hydrophobic membrane to retard entry of the initiating agent into the apparatus. Preferably, partition 380 is constructed using hydrophilic membrane so that the initiating agent, once within the apparatus, will migrate to partition 380. These hydrophobic and hydrophilic membranes are described above for the embodiments depicted in FIGS. 1A, 1B, 2A, and 2B. Similarly first reactant 342 and second reactant 344 are described above for the embodiments depicted in FIGS. 1A, 1B, 2A, and 2B. If, for example, first reactant 342 consists of sodium chlorite and second reactant 344 consists of citric acid, reaction begins when an initiating agent reaches partition 380. In a preferred embodiment, sachet 370 is constructed from 0.65 micron pore hydrophobic polypropylene membrane, such as that sold under the trade designation DOHP by Millipore (Bedford, Mass.), and partition 380 is constructed from 0.65 micron pore hydrophilic polyethylene membrane, such as that sold under the designation MPLC by Millipore (Bedford, Mass.).

Optionally, the apparatus depicted in FIGS. 4A and 4B may further comprise an envelope (not shown) enclosing the sachet. This envelope can be constructed from any of the envelope materials described above for the embodiments depicted in FIGS. 1A, 1B, 2A and 2B. Preferably, the envelope is a hydrophobic perforated film, such as the polypropylene copolymer film sold under the designation SM700 by Sealed Air Corporation (Duncan, S.C.) having 330 holes per square inch having a diameter of 0.4 mm, a 6.4% perforated area and a water vapor transmission rate of 700 $g/m^2/24$ hr. In a currently preferred embodiment, the envelope is constructed from a selective transmission film, such as the PD-961 Cryovac® selective transmission film from Sealed Air Corporation (Duncan, S.C.) disclosed above in connection with FIGS. 3A and 3B. Additionally, the apparatus can further comprise a frangible pouch, and initiating agent disposed within frangible pouch, disposed within the envelope.

Figure 5A:
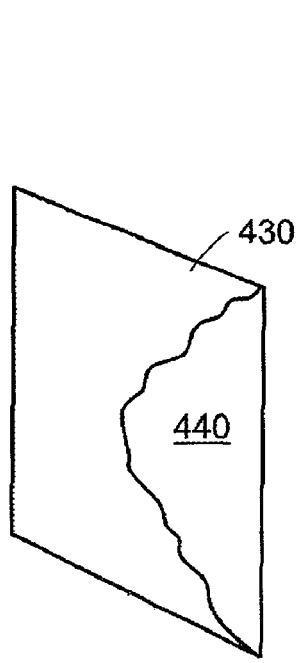
FIGS. 5A and 5B are a perspective view and a cross-sectional side view, respectively, of still yet another embodiment of an apparatus constructed in accordance with the present invention
Figure 5B:
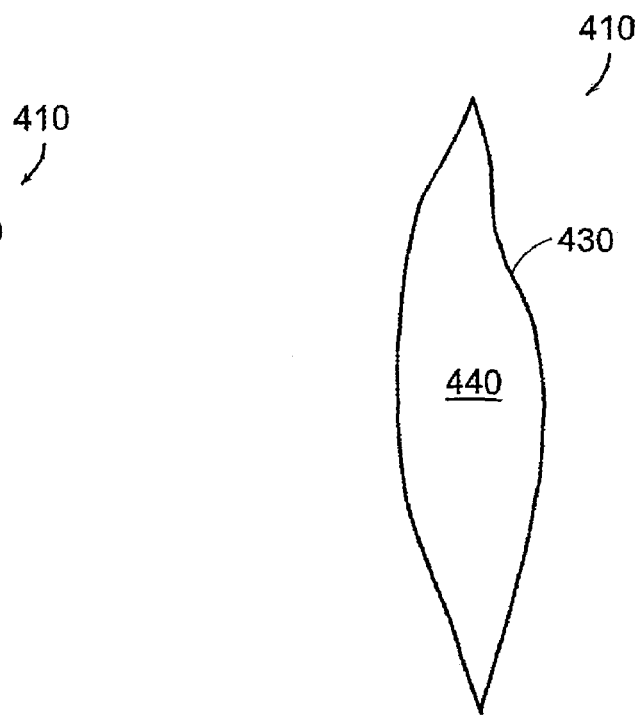

FIGS. 5A and 5B are a perspective view and a cross-sectional side view, respectively, of still yet another embodiment of an apparatus 410 constructed in accordance with the present invention. In general overview, apparatus 410 includes sachet 430 and reactant 440 disposed within sachet 430 that generates a gas in the presence of an initiating agent. Sachet 430 allows contact of the initiating agent with the reactant and release of the gas from the apparatus.

There may be instances where having only a sachet, i.e., no envelope, may be preferred over embodiments that further include envelopes. For example, where the performance of the apparatus without an envelope is sufficient, this embodiment is preferred, because production is simplified as the step of constructing the envelope is eliminated, and also because material costs may be decreased by eliminating the need to provide envelope layers to construct the envelope.

Sachet materials can be constructed from the materials described above for the embodiments depicted in FIGS. 1A, 1B, 2A, and 2B. Preferably, the sachet is constructed using hydrophobic membrane so that the sachet limits the amount of water entering the sachet. Similarly, reactant 440 is described above for the embodiments depicted in FIGS. 1A, 1B, 2A, and 2B.

FIGS. 8, 9, and 10 depict concentration versus time for various apparatus that include a sachet but do not include envelopes. A currently preferred embodiment is an apparatus where the sachet is constructed from a 0.65 micron pore size, hydrophobic polypropylene membrane sold under the trade designation DOHP by Millipore (Bedford, Mass.). The diamond-shaped data points in FIGS. 9 and 10 depict the performance of an apparatus with a sachet and without an envelope constructed from this material.

In view of the collective teachings and guidance set forth herein, the practitioner can design, fabricate, test and use any number of embodiments of the present invention. All that is required is an ordinary level of skill in the art and some routine experimentation. For example, for a disinfection application, a practitioner initially should determine the volume to be disinfected using a gas-generating apparatus of the instant invention. Next, appreciating that the current standard for cold sterilization/disinfection is 5 mg/L chlorine dioxide, the practitioner should determine the quantity of chlorine dioxide that will be required to disinfect the desired volume.

From the volume of chlorine dioxide gas required, the amount and ratio of reactant necessary to generate this amount of chlorine dioxide can be calculated. Of course, if a practitioner wishes to increase or decrease the disinfecting concentration, then one can adjust the reactant quantities placed in a sachet. Representative data generated with varying ratios of reactants are depicted in FIG. 11, for example. Variations in amounts generally are proportional, e.g., doubling the amount of sodium chlorite will double the amount of chlorine dioxide gas generated, if all other elements of the apparatus remain the same. Of course, the amount of gas generated can also be increased by envelope choice as described in connection with FIGS. 6 and 7.

Also, the practitioner should determine the time course of release of the disinfecting gas and choose sachet layers and envelope layers accordingly. For example, if a rapid release is desired, then reactants can be contained within a sachet fabricated from hydrophilic material; if a less rapid release is desired, then reactants can be contained in a hydrophobic material. Representative data generated with hydrophobic and hydrophilic sachet material are depicted in FIG. 10. Representative data generated with reactants housed in various embodiments of sachets and envelopes as taught by the present invention are depicted in FIGS. 6 through 11. The skilled artisan will appreciate that intermediate rates of release can be accomplished by mixing and matching different sachet layers and different envelope layers. Only routine experimentation is required.

Another aspect of the present invention features a method of forming an apparatus for delivery of a gas. This method includes the steps of: (a) providing a multi-layer structure comprising a reactant layer centrally disposed between two sachet layers, and two envelope layers disposed adjacent to the two sachet layers such that the two sachet layers are centrally disposed between the two envelope layers; and (b) stamping the multi-layer structure such that the two envelope layers form an envelope defined about its perimeter by the stamp, and the two sachet layers form a sachet defined about its perimeter by the stamp.

This method has many variations and embodiments. For example, a second reactant layer disposed between an additional two sachet layers can be included between the two envelope layers prior to step (a), so that upon stamping, the apparatus includes two sachets, each with its own reactant layer inside. Another variant adds the following steps to the method described above: (c) providing an initiating agent in a frangible pouch and a second two envelope layers, (d) stamping the second two envelope layers to form a second envelope defined about its perimeter by the stamp, such that the frangible pouch and the envelope formed in step (b) are disposed within the second envelope.

Stamping includes any method of forming an envelope from the envelope layers and a sachet from the sachet layers, e.g., sealing the perimeter with a glue or other sealant, impulse sealing and heat sealing.

This method is advantageous because it allows the apparatus of the present invention to be manufactured quickly and inexpensively relative to assembling and forming each individual sachet and envelope separately.

In another aspect, the above method can be modified to construct an apparatus without an envelope. For example, the method can includes the steps of: (a) providing a multi-layer structure comprising a reactant layer centrally disposed between two sachet layers; and (b) stamping the multi-layer structure such that the two sachet layers form a sachet defined about its perimeter by the stamp.

Yet another aspect of the present invention features a method of delivering gas. This method includes the steps of: (a) providing an apparatus for delivery of a gas comprising an envelope, a sachet disposed within the envelope, and a reactant disposed within the sachet that generates a gas in the presence of an initiating agent, wherein the envelope allows release of the gas from the envelope; and (b) disposing the apparatus in an environment that comprises an initiating agent.

This method has many variations and embodiments. For example, the environment can be liquid and the initiating agent can be water or the environment can be gaseous and the initiating agent can be water vapor. Preferably, the water vapor is that naturally diffused in the gaseous environment, e.g., atmospheric water diffused in air at ambient temperature.

In another aspect, the above method can be modified to includes the steps of: (a) providing an apparatus for delivery of a gas comprising a sachet and a reactant disposed within the sachet that generates a gas in the presence of an initiating agent; and (b) disposing the apparatus in an environment that comprises an initiating agent.

Optionally, to further increase stability of any of the apparatus of the present invention during storage and shipment, any desiccant, such as silica gel or molecular sieves, can be used to scavenge initiating agent prior to use of the apparatus.

Layered Apparatus

Figure 12A:
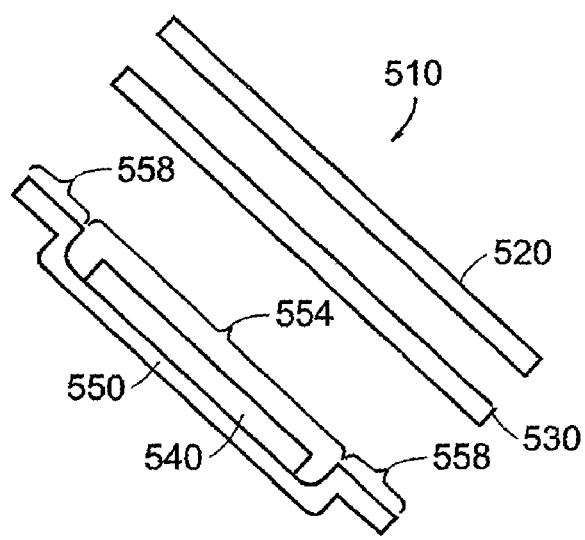
FIGS. 12A, 12B and 12C are an exploded view, a cross-sectional side view, and a perspective view, respectively, of one exemplary embodiment of an apparatus constructed in accordance with the present invention.
Figure 12B:
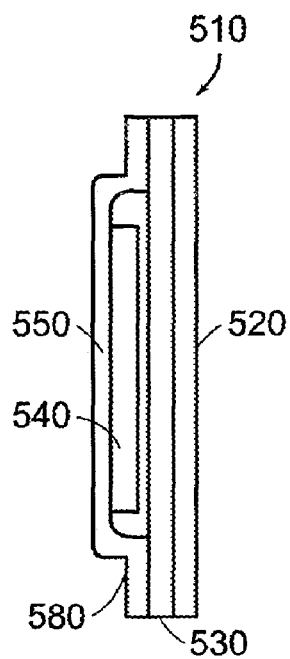
Figure 12C:
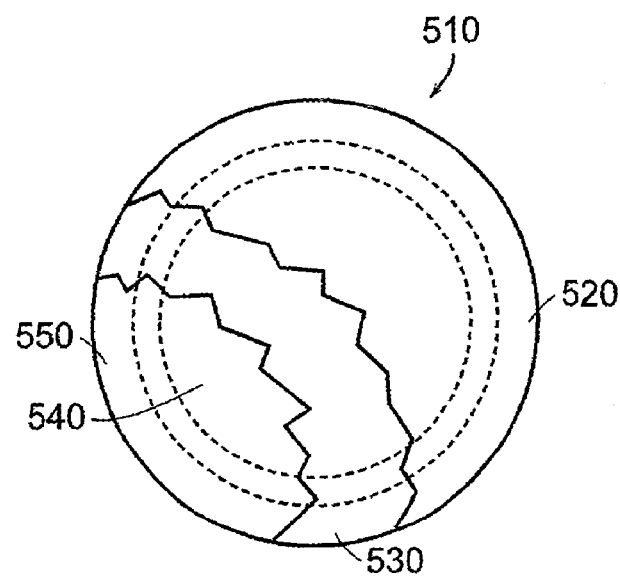

FIGS. 12A, 12B and 12C are an exploded view, a cross-sectional side view, and a perspective view, respectively, of an exemplary embodiment of an apparatus 510 constructed in accordance with the present invention. In general overview, apparatus 510 includes an envelope layer 520, a sachet layer 530 disposed adjacent to the envelope layer 520, a barrier layer 550 disposed adjacent to the sachet layer 530, and reactant 540 disposed in the volume defined by the sachet layer 530 and the barrier layer 550. The reactant 540 can generate a gas in the presence of an initiating agent, e.g., water. Sachet layer 530 and envelope layer 520, are permeable layers that allow passage of the initiating agent to the reactant 540 and release of the gas from the apparatus 510. Barrier layer 550 is formed to define a cavity 554 to receive reactant 540, and an edge 558 about its perimeter. The envelope layer 520 and sachet layer 530 are fused about their perimeter along the edge 558 of barrier layer 550. Apparatus 510 is particularly useful for the rapid release of a gas for wet applications.

Envelope layers are chosen to control the influx of the initiating agent, while limiting the diffusion of the reactants to the surrounding fluid, be it gaseous or liquid. The envelope layer also allows the gas generated by reactant to diffuse to the surrounding fluid, be it gaseous or liquid. By limiting transmission of the initiating agent into the apparatus, and limiting and/or preventing diffusion of the reactants out of the apparatus, the reactant remains concentrated and the pH of the reactive system is localized within the apparatus to optimize the conversion of reactant to gas. Additionally, intermediates and/or by-products of the reaction, e.g., water, also can contribute to the efficiency and/or duration of the reaction by its affect on the equilibrium of the reactions.

Preferred envelope layers are described above for the embodiments depicted in FIGS. 1A, 1B, 2A, 2B, 3A, 3B, 4A, 4B, 5A and 5B. An envelope layer that is currently preferred for this embodiment is a hydrophobic polypropylene copolymer film sold under the designation SM700 by Sealed Air Corporation and has 330 holes per square inch having a diameter of 0.4 mm, a 6.4% perforated area and a water vapor transmission rate of 700 g/m²/24 hrs at 50% relative humidity. Also suitable is a hydrophobic polypropylene copolymer film sold under the trade designation SM570 that has 162 holes per square inch having a diameter of 0.4 mm , a 32% perforated area and a water vapor transmission rate of 570 g/m²/24 hrs at 50% relative humidity and also is available from Sealed Air Corporation. Also suitable for use as an envelope layer is the polypropylene layer sold under the designation 060P1 by Cuno Incorporated (Meriden, Conn.).

The sachet layer can be used to limit the diffusion of the initiating agent into the volume defined by the sachet layer and the barrier layer, and limit the diffusion of reactant and any reaction by-products out of the volume defined by the sachet layer and the barrier layer. As a consequence, the reactant is and remains concentrated within the volume defined by the sachet layer and the barrier layer and the pH remains localized increasing the efficiency of the reaction. Various attributes of the sachet layer, such as pore size, bubble point, and hydrophobic and/or hydrophilic nature of the sachet, can be manipulated to control the affect of the sachet layer on the reaction as is described above.

Preferred sachet layers are described above for the embodiments depicted in FIGS. 1A, 1B, 2A, 2B, 3A, 3B, 4A, 4B, 5A and 5B. Sachet layers that are currently Preferred for this embodiment include an extruded, 0.65 micron pore size, hydrophilic polyethylene membrane sold under the trade designation MPLC from Millipore (Bedford, Mass.). Also suitable for use as sachet layers are the nylon 6,6 membrane layers sold under the designations 045ZN, 045ZY and 045ZL by Cuno Incorporated (Meriden, Conn.). The nylon 6,6 membrane layer sold under the trade designation 045ZY by Cuno Incorporated is currently preferred and has a thickness of between about 180 to about 240 microns, a pore size of about 0.45 microns, and a bubble point of about 24.1 psi.

The barrier layer preferably is constructed of a material that is durable and stable. Preferably, it is capable of being affixed to sachet layers and envelope layers for fabrication purposes, e.g., so that the layers can be fused about their perimeters to form a defined volume. Preferably, the impermeable layer has a water vapor transmission rate (WVTR) of less than about 50 g/m²/24 hrs at 70% relative humidity. More preferably, the impermeable layer has a water vapor transmission rate (WVTR) of less than about 2 g/m²/24 hrs at 70% relative humidity. Most preferably, the impermeable layer has a water vapor transmission rate (WVTR) of less than about 0.5 g/m²/24 hrs at 70% relative humidity.

Barrier layers can be constructed of various materials, including metals, polymeric material and/or coated papers. Other suitable materials for forming barrier layers include, but are not limited to, polymeric layers constructed from, e.g., polyethylene, polypropylene, polyester, styrene, including polystyrene, polyethylene terephthalate, polyethylene terephthalate glycol (PETG), polyvinyl chloride, polyvinylidene chloride, ethylvinyl alcohol, polyvinyl alcohol, including polyvinyl alcohol acetate, acrylobutylstyrene and/or polytetrafluoroethylene, polyacrylate and polyamide, including nylon. Also suitable are metallized layers, e.g., any of the above polymeric layers that have been metallized. Also suitable are metallic foils, such as aluminum foils. Various other impermeable materials can be used to form the barrier film as well, such as glass or ceramics. In addition layers that are composites of the above layers and/or laminates of the above layers, e.g., paper/film/foil composites are also suitable for use as a barrier layer. One currently preferred impermeable layer is a 5 mil thick impermeable layer comprising a polyester exterior, a metallized biaxially oriented core, and a polyethylene interior sealing layer available from Sealed Air Corporation (Duncan, S.C.). This layer has a water vapor transmission rate of 0.01 g/100 in²/24 hrs at 70% relative humidity and 122° F. Another currently preferred impermeable layer is constructed from polyvinyl chloride. Yet another currently preferred impermeable layer is constructed from polyethylene terephthalate glycol (PETG).

The geometry and size of the barrier layer can be adapted to suit various parameters, including the amount and type of reactant, the desired surface area of the sachet layer and/or envelope layer, and attachments for the storage and use of the apparatus. In one currently preferred embodiment, the barrier layer forms a cavity to receive reactant. It is also preferable that the barrier layer is formed such that it includes an edge about its perimeter for forming a seal with the sachet layer and/or envelope layer and/or second barrier layer. It is also preferable that the barrier layer forms a cavity that, with the one or more permeable layers, defines a volume that is the same or only slightly larger than the volume of the reactants. That is, it is preferable to minimize reactant headspace in the apparatus of the present invention.

The barrier layer also can be formed into a shape such that the apparatus is easily inserted into or removed from various containers, such as a bottle or pouch. For example, it can be formed so that it can be inserted into a cap, such as a bottle cap or pouch cap, so that the cap can then be attached, e.g., by a threaded seal, snap fit or pressure fit, to a receptacle for delivery of an initiating agent and/or receiving the generated gas. One such exemplary embodiment is described in greater detail in connection with FIGS. 16A and 16B below. The barrier layer also can be formed into various other geometries so that it can be otherwise affixed to a container, such as to a bottle. Two such exemplary embodiments are described in greater detail in connection with FIGS. 15 and 18 below.

The barrier layer can be formed into various geometries by various manufacturing methods known in the art, including but not limited to, horizontal form film seal, vertical form fill seal, blister pack, skin pack, injection molding, blow molding, thermoforming, cold forming fill seal, or mechanical forming. Of course, the barrier layer also may be flexible and not formed into any particular geometry, but sealed about its perimeter to the sachet about the reactant.

The envelope layer, sachet layer, and barrier layer of the present invention can be sealed about their perimeters by any known method, such as heat sealing, ultrasonic sealing, radio frequency sealing, impulse sealing, and sealing with adhesives. Preferably, the layers are fused with heat, by ultrasonic welding or by impulse sealing.

Reactant in general, preferred reactants, reactant ratios, and the like, are described above for the embodiments depicted in FIGS. 1A, 1B, 2A, 2B, 3A, 3B, 4A, 4B, 5A and 5B. Preferably, the reactant includes a stabilizer, such as activated hydrotalcite.

Optionally, in certain embodiments the reactant can further include a drying agent, or desiccant, to prevent premature initiation of the reactant. For example, desiccant can be added to the reactant to scavenge water vapor introduced during construction of the apparatus and/or shipping and storage of the apparatus, but in amounts small enough such that it would not prevent initiation when desired. Suitable desiccants include, for example, molecular sieves. Alternatively or additionally, desiccant can be separately contained in a permeable layer and located adjacent to or within the apparatus of the present invention to absorb or adsorb water vapor. One such exemplary embodiment is described in greater detail in connection with FIG. 20 below.

The ratio of volume defined by the sachet layer and the barrier layer to reactant volume also can be manipulated to control the concentration of the reactants, intermediates, byproducts, etc. within the volume defined by the sachet layer and the barrier layer. This relationship is described in above.

Figure 13:
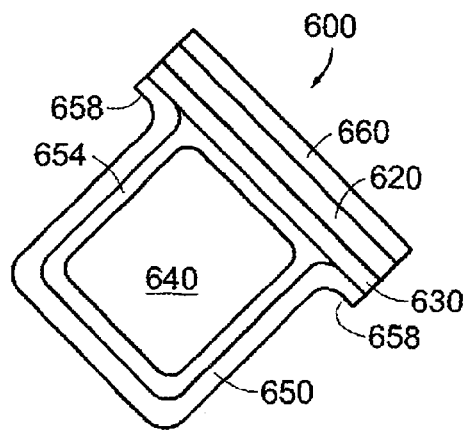
FIG. 13 is a cross-sectional side view of another exemplary embodiment of an apparatus constructed in accordance with the present invention.

FIG. 13 is a cross-sectional side view of another exemplary embodiment of apparatus 600 constructed in accordance with the present invention. In general overview, apparatus 600 includes an envelope layer 620, a sachet layer 630 disposed adjacent to the envelope layer 620, a barrier layer 650 disposed adjacent to the sachet layer 630, reactant 640 disposed in the volume defined by the sachet layer 630 and the barrier layer 650, and a second barrier layer 660 disposed adjacent to the envelope layer 620.

Sachet layer 630 and envelope layer 620, are permeable layers that allow passage of the initiating agent to the reactant 640 and release of the gas from the apparatus 600. Barrier layer 650 is an impermeable layer that defines a cuboid cavity 654 to receive reactant 640, and an edge 658 about its perimeter where the barrier layer 650 is attached to the sachet layer 630 and the envelope layer 620.

The second barrier layer 660 is sealed about its perimeter to the envelope layer 620. Preferably, second barrier layer 660 is sealed to the envelope layer 620 by a peelable seal where the seal strength is such that the barrier layer 660 can be removed from the envelope layer 620 without disrupting either the seal between envelope layer 620 and sachet layer 630, or the seal between sachet layer 630 and barrier layer 650. Until the second barrier layer 660 is removed, it prevents initiation of the reactant 640 because it prevents passage of the initiating agent to the reactant 640. Second barrier film 660 can be used to prevent passage of the initiating agent into the apparatus when it is not in use, e.g., during storage and shipping.

Apparatus 600 is particularly useful for applications where the apparatus 600 is likely to be stored and/or shipped in the presence of initiating agent, e.g., water vapor in the surrounding air. Apparatus 600 also is particularly useful for applications where a relatively large amount of reactant is desired as cavity 654 is formed to accommodate a relatively large amount of reactant. The two barrier layers 650, 660 prevent initiation of the reactant 650 until the second barrier layer 660 is removed.

The envelope layer, sachet layer, and barrier layer can be constructed from any of the materials described above in connection with the embodiments depicted in FIGS. 1A, 1B, 2A, 2B, 3A, 3B, 4A, 4B, 5A, 5B, 12A, 12B and 12C. Reactant in general, preferred reactant, reactant ratios, reactant volume and the like, are described above in connection with the embodiments depicted in 1A, 1B, 2A, 2B, 3A, 3B, 4A, 4B, 5A, 5B, 12A, 12B and 12C.

Optional second barrier layer 660 can be constructed from any of the materials described above in connection with the barrier layer depicted in FIGS. 12A, 12B and 12C. Second barrier layer 660 also can be constructed from the same or different materials used to construct the barrier layer 650. Currently preferred second barrier layers include metal foil, nylon layers, polyvinylidene chloride layers, ethylvinyl alcohol layers and composites or laminate of these layers, such as a metallic foil/polyethylene layer laminate.

The second barrier layer can be sealed to the perimeter of the envelope layer, or sachet layer if no envelope layer is used, using any of the methods described above in connection with sealing the barrier, sachet layer and envelope layer of FIGS. 12A, 12B and 12C. Preferably, the second barrier layer is attached to the envelope layer by impulse sealing or heat sealing. Optionally, the second barrier layer also can include a device, such as a tab along its perimeter that facilitates its removal from the envelope layer without disrupting the other layers.

Figure 14:
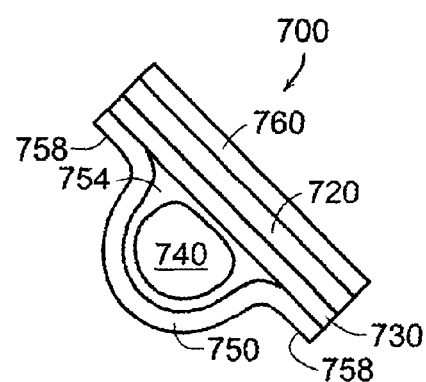
FIG. 14 is a cross-sectional side view of yet another exemplary embodiment of an apparatus constructed in accordance with the present invention.

FIG. 14 is a cross-sectional side view of another exemplary embodiment of apparatus 700 constructed in accordance with the present invention. In general overview, apparatus 700 includes an envelope layer 720, a sachet layer 730 disposed adjacent to the envelope layer 720, a barrier layer 750 disposed adjacent to the sachet layer 730, reactant 740 disposed in the volume defined by the sachet layer 730 and the barrier layer 750, and a second barrier layer 760 disposed adjacent to the envelope layer 720.

Sachet layer 730 and envelope layer 720, are permeable layers that allow passage of the initiating agent to the reactant 740 and release of the gas from the apparatus 700. Barrier layer 750 is an impermeable layer that forms a hemispheroid cavity 754 to receive reactant 740, and an edge 758 about its perimeter where the barrier layer 750 is attached to the sachet layer 730 and the envelope layer 720 by a heat or impulse seal.

The second barrier layer 760 also is sealed about its perimeter to the envelope layer 720 by a heat or impulse seal. Preferably, second barrier layer 760 is sealed to the envelope layer 720 so that it can be removed from the envelope layer 720 without disrupting the attachment of the envelope layer 720 to the sachet layer 730 and the sachet layer 730 to the barrier layer 750. Until the second barrier layer 760 is removed, it prevents initiation of the reactant 740 because it prevents passage of the initiating agent to the reactant 740. Second barrier film 760 can be used to prevent passage of the initiating agent into the apparatus when it is not in use, e.g., during storage and shipping.

Apparatus 700 is particularly useful for applications where the apparatus 700 is likely to be stored and/or shipped in an environment that allows contact of the initiating agent with the apparatus. Apparatus 700 also is particularly useful for applications where it is desirable to utilize relatively small amounts of reactant to deliver gas to limited volumes of liquid. The two barrier layers 750, 760 prevent initiation of the reactant 740 until the second barrier layer 760 is removed.

The envelope layer, sachet layer, and barrier layer can be constructed from any of the materials described above in connection with FIGS. 1A, 1B, 2A, 2B, 3A, 3B, 4A, 4B, 5A, 5B, 12A, 12B, 12C and 13. Reactant in general, preferred reactants, reactant ratios, and the like, are described above in connection with FIGS. 1A, 1B, 2A, 2B, 3A, 3B, 4A, 4B, 5A, 5B, 12A, 12B, 12C and 13.

The second barrier layer can be constructed from any of the materials described above in connection with the barrier layers depicted in FIGS. 12A, 12B, 12C and 13. The second barrier layer can be sealed to the perimeter of the envelope layer, or sachet layer if no envelope layer is used, using any of the methods described above in connection with sealing the barrier, sachet layer and envelope layer of FIGS. 12A, 12B and 12C and 13. Preferably, it is heat or impulse sealed or sealed with an adhesive. Optionally, the second barrier layer also can include a device, such as a tab along its perimeter that facilitates its removal from the envelope layer without disrupting the other layers (not shown).

Figure 15:
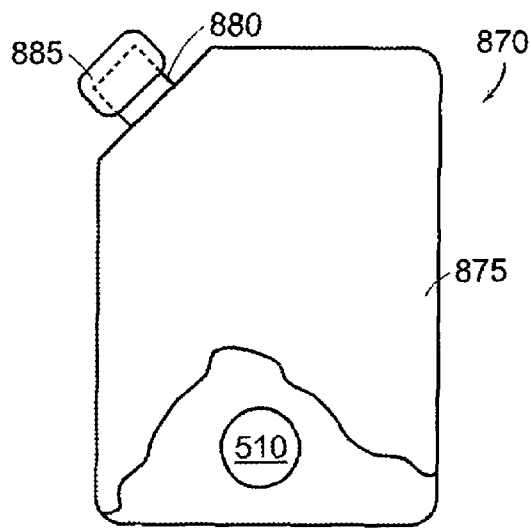
FIG. 15 is a perspective view of still yet another exemplary embodiment of an apparatus constructed in accordance with the present invention.

FIG. 15 is a perspective view of still yet another exemplary embodiment of an apparatus 870 constructed in accordance with the present invention. In general overview, apparatus 870 includes a pouch 875 having a spout 880 and a cap 885, and apparatus 510 as described in connection with FIGS. 12A, 12B and 12C. The apparatus 510 can be affixed to a wall of pouch 875, e.g., by adhesive or thermal bonding. Alternatively, it can be located within pouch 875 without being affixed thereto so that, e.g., it can be removed and replaced after use.

Apparatus 870 is particularly useful for the release of gas into a desired amount of liquid, e.g., water or air, so that a desired concentration of the gas in the liquid can be easily achieved. The amount of liquid can be defined by the volume of the pouch, pre-measured before addition of the pouch, or the pouch can include indicia located on the wall of the pouch to indicate various volumes that can be occupied by the liquid. The final concentration of the gas in the liquid can be controlled by choice of, e.g., of reactant amount, reactant ratio, sachet layer, and envelope layer, as described in connection with FIGS. 1A, 1B, 2A, 2B, 3A, 3B, 4A, 4B, 5A, 5B, 12A, 12B, 12C, 13 and 14.

The pouch and cap can be constructed from any of the impermeable or permeable materials disclosed above in connection with FIGS. 12A, 12B, 12C and 13-14. Preferably, the pouch and cap are constructed from polypropylene, polyethylene, polyethylene terephthalate, metal foil, nylon and/or composites or laminates of these layers such as a foil/polyethylene laminate. The pouch can be constructed from impermeable materials to avoid introduction of initiating agent into the pouch prior to the desired initiation of the reactant, e.g., during shipping and storage. One such pouch material suitable for use in accordance with the present invention is constructed from a 5 mil thick impermeable layer comprising a polyester exterior, a metallized biaxially oriented core, and a polyethylene interior sealing layer. This layer has a water vapor transmission rate of 0.01 g/100 in$^2$/24 hours at 70% relative humidity and 122° F. Alternatively or additionally, the apparatus 510 can further include a second barrier film as described in FIGS. 13 and 14.

The apparatus 870 can be used by filling the pouch 875 with a liquid that includes initiating agent, attaching the cap 885 to the spout 880, and awaiting the generation of the desired quantity of gas by apparatus 510 into the liquid contained within the pouch 875. This embodiment can be useful for preparing solutions for removing biofilm and/or sanitizing plastic waterlines in dental, marine or aerospace applications. This embodiment can also be useful for preparing solutions for surface sanitation, infection control and the like. Alternatively, any other water reservoir, such as a rigid bottle may be used instead of the pouch.

Figure 16A:
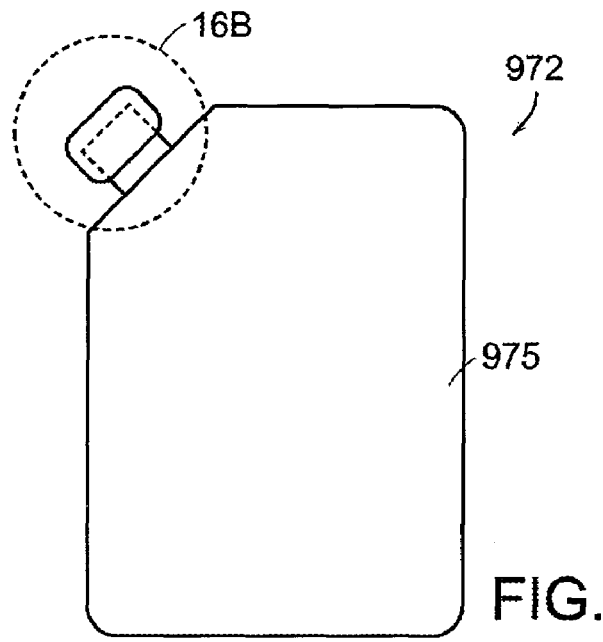
FIGS. 16A and 16B are a perspective view and an enlarged cross-sectional side view of a portion, respectively, of yet another exemplary embodiment of an apparatus constructed in accordance with the present invention.
Figure 16B:
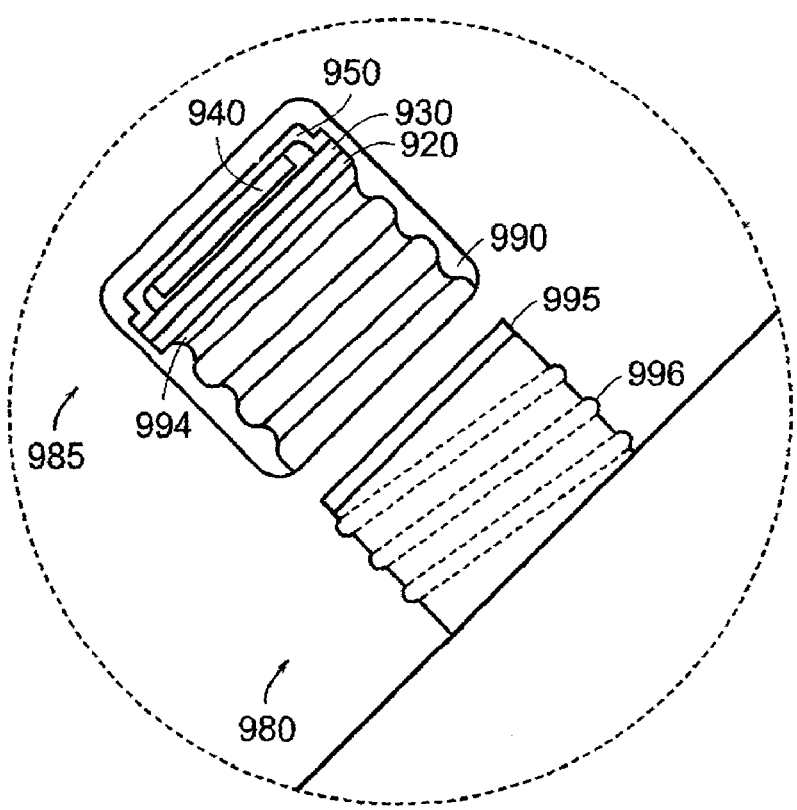

FIGS. 16A and 16B are a perspective view and an enlarged cross-sectional side view of a portion, respectively, of yet another exemplary embodiment of an apparatus 972 constructed in accordance with the present invention. In general overview, the apparatus 972 includes a pouch 975, a spout 980, and a cap 985. The cap 985 includes a barrier layer 950, reactant 940, a sachet layer 930 and an envelope layer 920. The barrier layer 950 is formed to define a cavity to receive reactant 940 and also is formed to fit into cap wall 990. The barrier layer 950 is attached to the cap wall 990 by snap in pressure fit so that it stays in position and can be removed and replaced after generation and release of the gas. Cap wall 990 defines an interior thread 994 that matches exterior thread 996 defined by spout 980. Spout 980 further includes a second barrier film 995 that seals the opening defined by the spout 980.

Apparatus 972 is particularly useful for preparing solutions for removing biofilm and sanitizing plastic waterlines in dental, marine, beverage and aerospace applications. This embodiment also can be useful for preparing solutions for surface sanitation, infection control and the like. One advantage of this embodiment is that the barrier films 950, 995 prevent initiation of the reactant when not in use, e.g., during shipping and storage, by sealing the apparatus by threading the cap to the spout in an environment substantially free from initiating agent and not removing the cap until initiation is desired. When generation of gas is desired, the cap can then be removed from the spout, and the second barrier film removed from the spout. The pouch can then be filled with liquid in part or entirely, the cap replaced and the reaction initiated, such that gas is released and enters the pouch.

Apparatus 972 also is advantageous because the pouch need not be constructed from impermeable materials, because the second barrier film prevents initiation of reaction when not in use, e.g., during storage and shipment.

The envelope layer, sachet layer, barrier layers, pouch and cap can be constructed from any of the materials are described in connection with FIGS. 1A, 1B, 2A, 2B, 3A, 3B, 4A, 4B, 5A, 5B, 12A, 12B, 12C, 13, 14 and 15. Reactant in general, preferred reactants, reactant ratios, and the like, also are described in connection with FIGS. 1A, 1B, 2A, 2B, 3A, 3B, 4A, 4B, 5A, 5B, 12A, 12B, 12C, 13, 14 and 15. The cap can be sealed by other means known in the art, e.g., by a pressure fitting.

Optionally, a barrier film can be placed on the opening defined by the cap wall. Thus, the cap can be stored and shipped separately from the pouch. This can be advantageous, e.g., in applications where the pouches can be reused, and thus material costs, storage space, storage costs, and shipping costs can be reduced. Alternatively, any other water reservoir, such as a rigid bottle may be used instead of the pouch depicted in FIGS. 16A and 16B.

FIGS. 17A and 17B are a cross-sectional side view and a perspective view, respectively, of still yet another exemplary embodiment of apparatus 1000 constructed in accordance with the present invention. In general overview, apparatus 1000 includes a sachet layer 1035, a barrier layer 1050 disposed adjacent to the sachet layer 1035, and reactant 1040 disposed in the volume defined by the sachet layer 1035 and the barrier layer 1050. Sachet layer 1035 is a permeable layer. Barrier layer 1050 is an impermeable layer and defines a cavity 1054 and an edge 1058 about its perimeter.

Apparatus 1000 is particularly useful for applications where the performance of the apparatus without an envelope layer is sufficient because production is simplified as the step of constructing the envelope layer is eliminated. In addition, eliminating the need to provide an envelope layer to construct the apparatus can decrease material costs.

The sachet layer and barrier layer can be constructed from any of the materials described in connection with FIGS. 1A, 1B, 2A, 2B, 3A, 3B, 4A, 4B, 5A, 5B, 12A, 12B, 12C, 13, 14, 15, 16A and 16B. Preferably, the sachet layer is constructed using a hydrophobic membrane so that the sachet layer limits the amount of water entering the apparatus. A currently preferred embodiment is an apparatus where the sachet layer is constructed from a 0.65 micron pore size, hydrophobic polypropylene membrane sold under the trade designation DOHP by Millipore (Bedford, Mass.). Another currently preferred embodiment is an apparatus where the sachet layer is constructed from a polypropylene layer sold under the trade designation 060P1 by Cuno Incorporated (Meriden, Conn.).

Reactant in general, preferred reactants, reactant ratios, and the like, are described in connection with FIGS. 1A, 1B, 2A, 2B, 3A, 3B, 4A, 4B, 5A, 5B, 12A, 12B, 12C, 13, 14, 15, 16A and 16B.

Figure 18:
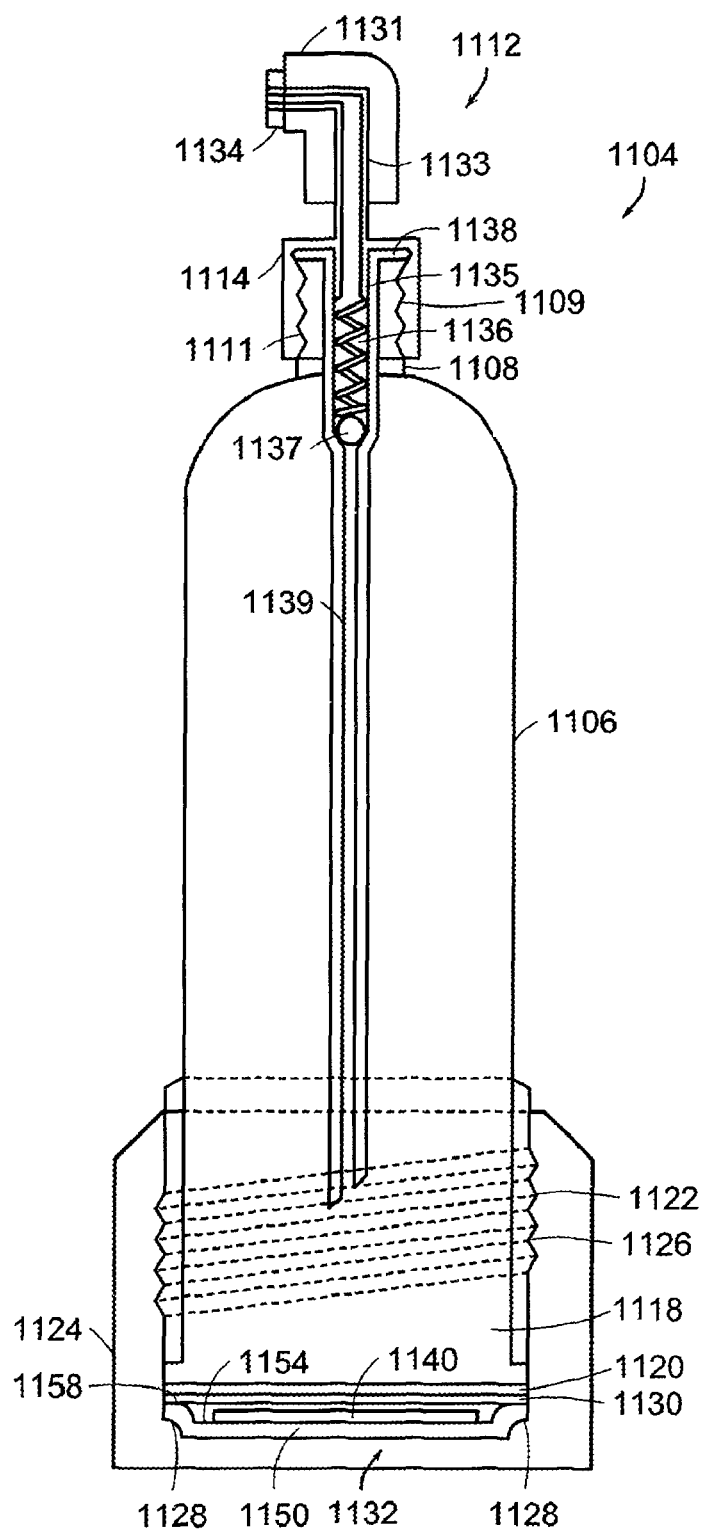
FIG. 18 is a cross-sectional side view of still yet another exemplary embodiment of an apparatus constructed in accordance with the present invention.

FIG. 18 is a cross-sectional side view of still yet another exemplary embodiment of an apparatus 1104 constructed in accordance with the present invention. In general overview, apparatus 1104 includes a tubular bottle 1106, a pump mechanism 1112 in threaded connection with the tubular bottle 1106 on a first end, a detachable portion 1124 in threaded connection with the tubular bottle 1106 on a second end, and insert 1132.

The bottle 1106 forms a spout 1108 that forms an exterior thread 1109 on the first end that attaches to the pump mechanism 1112 fixed in screw cap 1114 that forms a matching interior thread 1111. The bottle 1106 also defines an opening 1118 on the second end and exterior thread 1122 for attachment to the matching, interior thread 1126 defined by detachable portion 1124. Detachable portion 1124 also is formed to define a ridge 1128 about its interior perimeter that receives the insert 1132.

Insert 1132 includes a barrier layer 1150, reactant 1140, a sachet layer 1130, and an envelope layer 1120. The barrier layer 1150 is formed to snap into ridge 1128 and form a pressure fit so that it will remain in place during use and after use can be removed and replaced with another similarly configured insert. The barrier layer 1150 also is formed to define a cavity 1154 to receive reactant 1140 and an edge 1158 about its perimeter for attachment to the sachet layer 1130 and the envelope layer 1120. Optionally, insert 1132 can further include a second barrier layer adjacent to the envelope layer 1120 (not shown) as described in connection with FIGS. 13 and 14.

Pump mechanism 1112 includes tubular plunger 1133 on which pushbutton 1131 is mounted containing a spray nozzle 1134. Also shown are basic components of a typical pump, such as piston 1135, cylindrical chamber 1136, one-way valve 1137, collar 1138, and intake tube 1139. Alternate pump mechanisms are known in the art, such as the mechanisms described in U.S. Pat. No. 4,077,549.

Apparatus 1104 is particularly useful for use in generating a desired concentration of gas in a liquid, e.g., water, that can then be easily delivered to a desired location, e.g., a countertop for disinfection, via a pump mechanism. The pump mechanism can be removed from the spout so that the volume defined by the tubular bottle and detachable portion can be filled, partially or entirely, with a liquid, e.g., water. Detachable portion can be removed to attach or replace the insert 1132, so that bottle 1106, pump mechanism 1112, and detachable portion 1124 can be reused.

The envelope layer, sachet layer, and barrier layer can be constructed from any of the materials are described in connection with FIGS. 1A, 1B, 2A, 2B, 3A, 3B, 4A, 4B, 5A, 5B, 12A, 12B, 12C, 13, 14, 15, 16A, 16B, 17A and 17B. Reactant in general, preferred reactants, reactant ratios, and the like, are described in connection with FIGS. 1A, 1B, 2A, 2B, 3A, 3B, 4A, 4B, 5A, 5B, 12A, 12B, 12C, 13, 14, 15, 16A, 16B, 17A and 17B.

The tubular bottle and the detachable portion can be constructed from any material described in connection with the pouch and cap described in FIGS. 15, 16A and 16B. The tubular bottle can be formed by any method known in the art, e.g., blow molding or injection molding. Pump mechanism 1112 can be any pump mechanism known in the art. A wide variety of pump mechanisms are commercially available.

FIG. 20 is a cross-sectional side view of another exemplary embodiment of apparatus 1310 constructed in accordance with the present invention. In general overview, apparatus 1310 includes an envelope layer 1320, a sachet layer 1330 disposed adjacent to the envelope layer 1320, a barrier layer 1350 disposed adjacent to the sachet layer 1330, reactant 1340 disposed in the volume 1354 defined by the sachet layer 1330 and the barrier layer 1350, and desiccant 1341 disposed in the volume 1355 defined by the sachet layer 1330 and the barrier layer 1350.

Sachet layer 1330 and envelope layer 1320, are permeable layers that allow passage of the initiating agent to the reactant 1340 and release of the gas from the apparatus 1310. Barrier layer 1350 is an impermeable layer that forms cavities 1354, 1355 to receive reactant 1340 and desiccant 1341, respectively. The barrier layer 1350 is attached to the sachet layer 1330 and the envelope layer 1320 by a heat or impulse seal about the perimeter of the cavities 1354, 1355. Optionally a second barrier layer (not shown) can be sealed about its perimeter adjacent to the envelope layer 1320. Desiccant 1341 can be used to attract any ambient water vapor and/or liquid water and thereby prevent or minimize passage of water vapor and/or liquid water to the reactant 1340 disposed in cavity 1354 during storage and shipping.

This embodiment is particularly useful for wet applications and is more resistant to premature initiation than, e.g., the embodiment depicted in FIGS. 12A, 12B and 12C, due to the presence of the desiccant.

The envelope layer, sachet layer, barrier layer, and reactant can be any of those described in connection with the above FIGS. 1A, 1B, 2A, 2B, 3A, 3B, 4A, 4B, 5A, 5B, 12A, 12B, 12C, 13, 14, 15, 16A, 16B, 17A, 17B, 18 and 19. In a currently preferred embodiment, the envelope layer is a hydrophobic polypropylene copolymer film sold under the designation SM700 by Sealed Air Corporation and has 330 holes per square inch having a diameter of 0.4 mm, a 6.4% perforated area, a thickness of about 20 microns, and a water vapor transmission rate of 700 g/m$^2$/24 hrs, the sachet layer is extruded, 0.65 micron pore size, hydrophilic polyethylene membrane sold under the trade designation MPLC from Millipore (Bedford, Mass.) or Nylon 6,6 membrane layer sold under the trade designation 045ZY by Cuno Incorporated having a thickness of between about 180 to about 240 microns, a pore size of about 0.45 microns, and a bubble point of about 24.1 psi, the barrier layer is a polyethylene terephthalate glycol (PETG) or polyvinyl chloride (PVC) layer, the reactant includes sodium chlorite and citric acid, and the desiccant comprises molecular sieves.

Apparatus 1310 can also be incorporated into a pouch like that depicted in FIG. 15 to generate a desired concentration of gas, e.g., chlorine dioxide, in water. This embodiment is particularly useful in wet applications, e.g., for use in removing biofilm from dental equipment. One such apparatus was constructed and used to generate an aqueous solution containing 50 parts per million chlorine dioxide. It was then emptied into a dental equipment reservoir and allowed to run through the equipment, which was contaminated with biolfilm, and stand overnight. In the morning, the dental equipment was flushed with water. This procedure was repeated the following two nights. The equipment was then tested for the presence of biofilm and the biofilm was diminished. Thereafter, rinsing the equipment once daily with a 5 parts per million solution was adequate to retard the growth of biofilm in the equipment.

In view of the collective teachings and guidance set forth herein, the practitioner can design, fabricate, test and use any number of embodiments of the present invention. All that is required is an ordinary level of skill in the art and some routine experimentation.

Another aspect of the present invention features a method of forming an apparatus for delivery of a gas. This method includes the steps of: (a) providing a multi-layer structure comprising a reactant layer centrally disposed between a sachet layer and a barrier layer, and an envelope layer disposed adjacent to the sachet layer; and (b) sealing the perimeter of the barrier layer, sachet layer and barrier layer such that the reactant is disposed in a volume defined by the sachet layer and the barrier layer.

This method has many variations and embodiments. For example, a second barrier layer can be disposed adjacent to the envelope layer opposite the sachet layer prior to step (a). Another example is that in step (b) the seal can be effected by adhesive and/or by stamping the multi-layer structure with a hot die to heat-seal the layers together.

Sealing includes any method of substantially sealing the envelope layer, the sachet layer and the barrier layer about their perimeters, e.g., sealing the perimeter with a glue or other sealant, impulse sealing, ultrasonic sealing and heat sealing.

In a preferred embodiment, the apparatus is manufactured in an array for ease of manufacturing. This method includes: (a) providing a layer of impermeable material that has an array of cavities formed therein; (b) disposing reactant in the array of cavities; (c) disposing one or more permeable layer over the layer of impermeable material; (d) sealing the one or more permeable layers to the layer of impermeable material about the perimeter of each cavity; and (e) cutting the impermeable material and the one or more permeable materials about the perimeter of each cavity.

This method is advantageous because it allows the apparatus of the present invention to be manufactured quickly and inexpensively relative to assembling and forming each individual sachet and envelope separately and/or manually.

The impermeable material provided in step (a) can have an array of cavities formed therein, e.g., by using a thermoforming process to form the array of cavities. Thermoform machines suitable for use in accordance with the present invention include those manufactured by Multivac (Kansas City, Mo.), Tiromat (Avon, Mass.) Robert Reiser & Co. (Canton, Mass.), and Ulma Packaging (Woodstock, Ga.). Other suitable methods for forming the array of cavities include vacuum forming, cold forming, mechanical forming, and blister or skin packing process. The reactant can be disposed in the array of cavities on an assembly line and the one or more permeable layers can be sequentially positioned over the impermeable material, e.g., by unwinding sheets of the one or more permeable layers over the impermeable layer on an assembly line. The one or more permeable layers can then be sealed to the impermeable material about the perimeter of each cavity using methods known in the art, e.g., adhesives, heat sealing methods, ultrasonic sealing methods, radio frequency sealing methods or impulse sealing. The impermeable material and the one or more permeable materials can then be cut about the perimeter of each cavity using methods known in the art, e.g., by using a die, to form an apparatus similar to those depicted in FIGS. 12A, 12B, 12C, 13-15, 16A, 16B, 17A, 17B, 18 and 20.

These apparatus can then be inserted into the spout of a pouch that has been otherwise sealed about its periphery. Alternatively, it can be inserted into a pouch that has not been sealed about its periphery and the periphery then sealed, e.g., by using adhesive, heat sealing methods, ultrasonic sealing methods, radio frequency sealing methods or impulse sealing methods. Optionally, the apparatus can be attached to a wall of the pouch, e.g., by using adhesive, heat sealing methods, ultrasonic sealing methods, radio frequency sealing methods or impulse sealing methods.

In another aspect, the above method can be modified to construct an apparatus without an envelope. For example, the method can include the steps of: (a) providing a multi-layer structure comprising a reactant layer centrally disposed between a sachet layer and a barrier layer; and (b) sealing the multi-layer structure such that the such that the reactant is disposed in a volume defined by the sachet layer and the barrier layer Yet another aspect of the present invention features a method of delivering gas. This method includes the steps of: (a) providing an apparatus for delivery of a gas comprising an envelope layer, a sachet layer disposed adjacent to the envelope layer, a barrier layer disposed adjacent to the sachet layer, and a reactant disposed in a volume defined by the sachet layer and the barrier layer; and (b) disposing the apparatus in an environment that comprises an initiating agent.

This method has many variations and embodiments. For example, the environment can be liquid and the initiating agent can be water or the environment can be gaseous and the initiating agent can be water vapor. The apparatus can further comprise a pouch that can be filled with a desired liquid to receive the gas generated.

Optionally, to further increase stability of any of the apparatus of the present invention during storage and shipment, any desiccant, such as silica gel or molecular sieves, can be incorporated within the apparatus to scavenge initiating agent prior to use of the apparatus.

The present invention is useful for fabrication of a gas delivery apparatus that is compact, cost-effective and safe. Furthermore, the present invention can be used for a variety of applications, including delivery of gas to air or water, for a variety of purposes including removal of biofilm, disinfection, deodorization, bleaching and sanitation.

As a general rule and without wishing to be confined to any theory, it is expected that the amount and rate of gas release exhibited by apparatus of the present invention will be influenced by the total surface area of the permeable layer adjacent to the reactant, but not by the geometry of the apparatus. That is, the various embodiments of the present invention are expected to release the same volume of gas at the same rate provided that the total surface area of the permeable layer adjacent to the reactant is about equal, all other variables being held constant. It has been discovered that hydrotalcite, and the metal hydroxides in the hydrotalcite family, can be used to stabilize one or more reactants of the present invention. For example, hydrotalcite, including activated hydrotalcite, and metal hydroxides in the hydrotalcite family can be used to stabilized the following reactants and combination of these reactants: acids, aqueous acids, citric acid, oxalic acid, fumaric acid, phosphoric acid, potassium bitartate, chlorites, chlorates, sulfites, bisulfites, sulfates, carbonate, nitrites. While not wishing to be bound to any particular theory, it is believed that the basic nature and ability to attract and bind water and water vapor of hydrotalcite and its family members contribute to its ability to stabilize the reactants of the present invention. Basic additives are less likely to react with chlorites and other reactants that react with acid than acidic additives. In addition, the ability of hydrotalcite and its family members to attract, absorb, adsorb and/or otherwise bind water and water vapor mitigates or prevents premature initiation, e.g., during manufacture, shipping, and storage. The ability of hydrotalcite to function as a flow agent also is desirable because it renders the reactants more readily metered and dispensed during manufacture. Activated hydrotalcite, i.e., hydrotalcite that has been heated drive off water, has been found to stabilize reactants in an apparatus such as those described in Examples 12 and 13 for at least six months. The apparatus are expected to have a shelf life of at least a year.

The mineral commonly known as hydrotalcite is the naturally occurring form of hydrotalcite, which has the chemical formula: $Mg_6Al_2(OH)_{16}CO_3 \cdot 4H_2O$. Hydrotalcite, suitable for use in the apparatus of the present invention, is commercially available from DIP Chemical Industries (Mumbai, India). When activated, this hydrotalcite is hygroscopic, in that it absorbs water vapor up to about 36% of its weight when exposed to about 97% relative humidity, and has a surface pH between about 11 and about 12. The hydrotalcite can be activated using known methods, e.g., by exposing it to high temperatures for an extended period of time, e.g., 500° C. for one hour, and thereafter sealing the hydrotalcite in a low humidity environment so that it doesn't deactivate prematurely.

There also are metal hydroxides in the hydrotalcite family that can be used to stabilize reactants in accordance with the present invention. The family can be described with the general formula: $A_w B_x(OH)_y C_z.nH_2O$, wherein A is a divalent metal cation, B is a trivalent metal cation, and C is a monovalent, divalent, trivalent, or tetravalent anion. The values for w, x, y, z, and n have the following relationship: $0 \leq z \leq x \leq 4 \leq w \leq \frac{1}{2}y$, and $12 \geq n \geq \frac{3}{2}x$. Metal cations represented by A include, but are not limited to, $Mg^{2+}$, $Ni^{2+}$, $Fe^{2+}$, and $Zn^{2+}$. Metal cations represented by B include, but are not limited to, $Al^{3+}$, $Fe^{3+}$, and $Cr^{3+}$. Chemical species represented by C include, but are not limited to $CO_3^{2-}$, $SO_4^{2-}$, $OH^-$, $NO_3^-$, and $Cl^-$. One such hydrotalcite is a hydrotalcite having the formula: $Mg_4Al_2(OH)_{12}CO_3.nH_2O$, and is commercially available from Alcoa World Chemicals (Leetsdale, Pa.). Other suitable minerals in the hydrotalcite family include pyroaurite having the formula $Mg_6Fe^{3+}_2(OH)_{16}CO_3.4H_2O$, and takovite having the formula $Ni_6Al_2(OH)_{16}[(CO_3)_{0.75}(OH)_{0.25}].4H_2O$. Preferably, the hydrotalcite is added to the reactant such that the resulting mixture is between about 1% and about 25% hydrotalcite by weight. More preferably, the resulting mixture is between about 5% and about 20% hydrotalcite by weight.

Another aspect of the present invention is an apparatus for delivery of a gas including a sachet that includes a material that is water vapor selective, and a reactant disposed in the sachet that generates a gas in the presence of an initiating agent. The term "water vapor selective" as used herein refers to a material that selectively allows permeation of water vapor and substantially impedes permeation of liquid water. More preferably, the material excludes permeation of liquid water. Typically, the water vapor selective material is hydrophobic. The skilled practitioner typically refers to water vapor selective material as water impermeable, although water vapor can permeate the layer, and refers to materials that allow permeation of liquid water as water permeable. Suitable water vapor selective materials can be made from a variety of materials including, but not limited to, polytetrafluoroethylene (PTFE), polypropylene (PP), polyethylene (PE), and fluorinated ethylene propylene (FEP).

Water vapor selective material also is particularly advantageous because it substantially impedes or excludes the diffusion of water soluble species, such as water soluble reactants, additives, and reaction by-products, out of the apparatus. Membranes that allow liquid water permeation allow soluble species such as soluble reactants to permeate the apparatus and enter the environment. Prior attempts have been made to ameliorate or avoid escape of soluble species by using insoluble reactants or by binding or otherwise disposing the soluble species on insoluble materials such as clays and molecular sieves. This is not advantageous because it introduces additional steps and/or expense to the preparation of the apparatus. Thus, the water vapor selective materials of the present invention are advantageous because they impede or preclude the permeation of the soluble reactants, additives, and by-products, thus removing the need to include or generate insoluble reactants, by-products and/or additives.

Water vapor selective materials also are advantageous because their use eliminates the need to use any further layers, e.g., further sachet and/or envelope layers, to retain soluble species in the apparatus, which also introduces additional steps and expense in the construction of the apparatus.

Preferably, the water vapor selective material has a thickness between about 5 microns and about 400 microns thick, a pore size between about 0.05 microns and about 10 microns, and a water intrusion pressure between about 30 millibars and about 4,000 millibars. Preferably, the water vapor selective material is adhered to or otherwise supported by a support layer that allows liquid water to permeate the support layer, and the overall thickness of both the water vapor selective layer and the support layer is between about 1 mil and 20 mils. More preferred, are water vapor selective materials having a thickness between about 15 microns and about 200 microns thick, a pore size between about 0.25 microns and about 5 microns, and a water intrusion pressure between about 100 millibars and about 1,500 millibars. Preferably this layer has a water permeable support layer such that the total thickness of both layers is between about 2 mils and about 10 mils. Most preferred, are water vapor selective materials having a thickness between about 20 microns and about 100 microns thick, a pore size between about 1 micron and about 3 microns, and a water intrusion pressure between about 200 millibars and about 750 millibars. Preferably this layer has a water permeable support layer such that the total thickness of both layers is between about 3 mils and about 8 mils.

Generally, if rapid generation and release of gas is desired, a thinner layer is preferred because the thinner the layer, the more rapidly water vapor can diffuse into the apparatus and initiate the reaction, and the more rapidly gas can diffuse out of the apparatus. Conversely, if slower generation and release of gas is desired a thicker material is preferred, such as between about 5 mils and about 20 mils. Additionally or alternatively, if slower generation and release of gas is desired, a relatively smaller surface area of the material can be used. For example, a sachet including a rigid frame can be used to construct the sachet as described below and illustrated in Example 15, and one or both sachet layers can be constructed from a water vapor selective material.

Additionally or alternatively, pore size of the water vapor selective layer can be selected to produce the desired release at specific depths of water in which the apparatus will be used. A smaller pore size will correspond to deeper operation by increasing the amount of hydraulic water pressure that the membrane will experience while remaining impermeable to liquid water.

Water vapor selective layers suitable for use in constructing the apparatus of the present invention preferably have water vapor permeability of between about 2,000 $g/m^2/24$ hrs and about 150,000 $g/m^2/24$ hrs, as determined by JIS L 1099-1985 (Method B), "Testing Methods for Water Vapour Permeability of Clothes," from the Japanese Standards Association. Water vapor selective layers preferably have a resistance to liquid water permeation of at least about 30 millibars as determined by ISO 811-1981 "Textile fabrics—Determination of resistance to water penetration—Hydrostatic pressure test" published by the International Organization for Standardization.

Optionally, the water vapor selective layer or layers of the present invention can include a support layer to increase the strength of the layer, and/or to increase its ability to bond to the other materials used to construct the apparatus. The support layer preferably allows diffusion or passage of initiating agent to the surface of the water vapor selective layer. For example, the support layer can be spun, perforated or have large pores that allow passage of liquid water and vapor to the surface of the water vapor selective layer. The support layer can be affixed to the water vapor selective layer by any means, for example, lamination, casting, co-extrusion, and/or adhesive layers. Preferably, the sachet is constructed so that the water vapor selective layer faces the interior of the sachet. The support layer itself can be hydrophilic and/or hydrophobic. If hydrophilic, the material can be used to attract and deliver liquid water and/or vapor to the surface of the water vapor selective material. Suitable support layers include, but are not limited to, polyethylene, polypropylene, nylon, acrylic, fiberglass, and polyester in the form of woven, non-woven, and mesh layers. Preferably, the support layer thickness is between about 1 mil and 20 mils.

Suitable water vapor selective materials previously described herein include the 0.60 pore size, hydrophobic, polypropylene (PP) membrane having a thickness between about 250 microns and about 300 microns sold under the designation 060P1 by Cuno Incorporated (Meriden, Conn.). Also suitable is the 0.65 micron pore size, hydrophobic polyethylene material sold under the trade designation DOHP by Millipore (Bedford, Mass.)

Another water vapor selective material, suitable for use in a rapid release apparatus, includes a 1.75 mil thick, hydrophobic polytetrafluoroethylene (PTFE) layer thermally bonded to a 5 mil thick, hydrophobic polyethylene (PE) support layer sold under the trade designation BHA-TEX® by BHA Technologies (Kansas City, Mo.). Its resistance to liquid water permeation is at least about 500 millibar.

Figure 21:
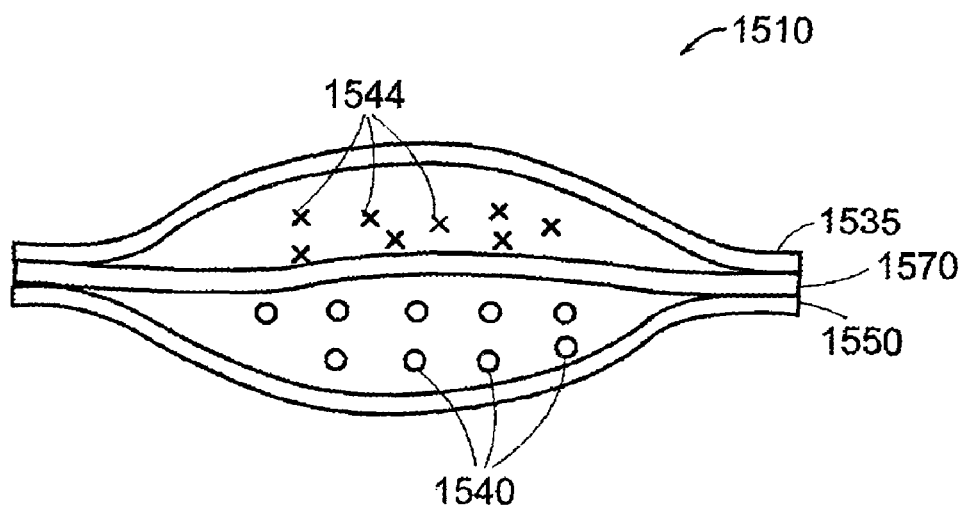
FIG. 21 is a perspective view of yet another exemplary embodiment of an apparatus constructed in accordance with the present invention.

FIG. 21 is a perspective view of yet another exemplary embodiment of an apparatus 1510 constructed in accordance with the present invention. Apparatus 1510 includes a sachet layer 1535, an intermediate layer 1570 disposed adjacent the sachet layer 1535, and a barrier layer 1550 disposed adjacent the intermediate layer 1570. A first reactant 1540 is disposed in the volume defined by the barrier layer 1550 and the intermediate layer 1570, and a second reactant 1544 is disposed in the volume defined by the intermediate layer 1570 and the sachet layer 1535.

The sachet layer can be constructed from any of the layers described above. Preferably, the sachet layer includes a water vapor selective layer and an adjacent support layer. The first reactant and the second reactant can be any of the reactants described above. The reactant or reactants can further include additives, such as activated hydrotalcite. The intermediate layer can be constructed of any of the layers described above. Preferably, the intermediate layer comprises a cellulose layer such as the Japanese paper "Tosa Tengujo" sold by Bookmakers (Hagerstown, Md.). The barrier layer can include any of the barrier layers describe above. In a preferred embodiment the barrier layer is constructed from a composite of a metalized bi-axially oriented polypropylene about 1 mil thick and a linear low density polyethylene about 4 mils thick. This apparatus is advantageous because it can be constructed by placing sheets of the sachet, intermediate, and barrier layers adjacent each other and sealing about the edges and cutting about the seal in one step. Optionally, a portion of the apparatus can be left unsealed until the volumes defined by the layers are filled with reactant and then sealed. Alternatively, the reactant can be layered with the layers and the entire periphery of the layers sealed at once.

Sachets Including a Rigid Frame

In another aspect of the invention, the apparatus includes a sachet that includes a rigid frame defining at least one opening and a sachet layer disposed about the opening such that a volume is defined by the sachet. The rigid frame can be a rigid barrier layer as described above. The rigid frame also can take the form of a tubular member that can have any shape, such as a circular, oval, rectangular, or square-shaped cross section along the tube. If the rigid frame is tubular, at least one end preferably has a sachet layer disposed about it. A second sachet layer may be disposed about a second end of the rigid frame. Additionally or alternatively, any other layer that will define a closed receptacle for reactant, such as a barrier layer, can be disposed about a second end. Yet another option is to have a detachable member on the second end such as a threaded cap that can be removed, e.g., to remove and/or replace reactant and any additional sachets within the sachet. Sachets including rigid frames are advantageous because they can be fit into various devices, e.g., a humidifier, filter or cartridge. They also can be dropped in a reservoir and, depending on the materials used to construct the rigid frame, can sink to the bottom of a solution, e.g., if made with PVC, or float on top, e.g., if constructed with a foamed material. The apparatus can further include weighted materials to increase its tendency to reside at a bottom of a reservoir. The sachet includes one or more reactants that generate a gas in the presence of the initiating agent. The reactants can be mixed or separated by further structures, such as an additional sachet or an intermediate layer within the sachet as described herein.

Figure 22A:
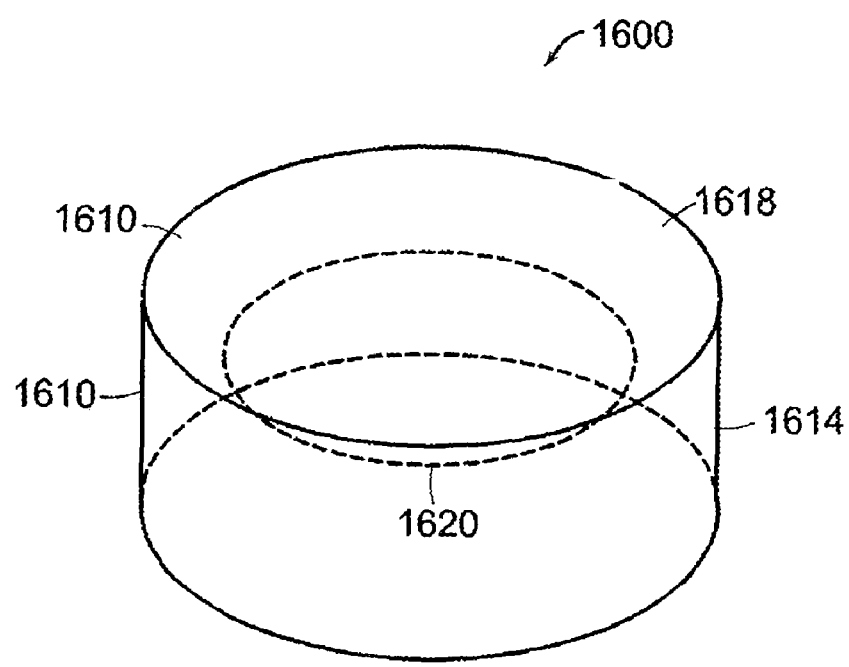
FIGS. 22A and 22B are a perspective and cross-sectional side view, respectively, of an exemplary embodiment of an apparatus including a sachet constructed in part with a rigid frame.
Figure 22B:
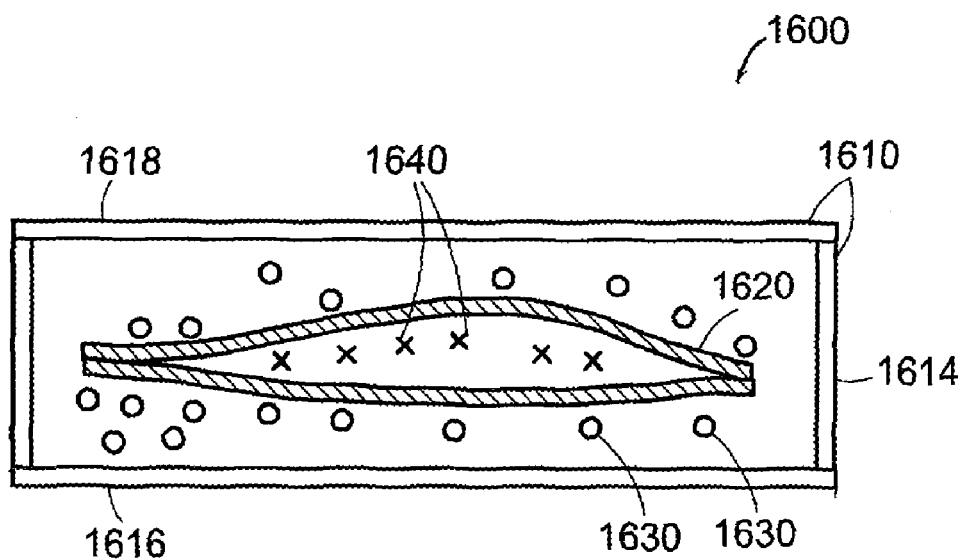

FIGS. 22A and 22B are a perspective and cross-sectional side view, respectively, of an exemplary embodiment of an apparatus 1600 including a sachet constructed in part with a rigid frame. The apparatus 1600, includes a first sachet 1610, a second sachet 1620, a first reactant 1630, and a second reactant 1640. The first sachet is constructed from a rigid frame 1614 that is cylindrical in shape and two sachet layers 1616, 1618 disposed on either side of the rigid frame 1614 such that the rigid frame 1614 and the sachet layers 1616, 1618 define a closed receptacle for reactant. The first reactant 1630 is disposed in the first sachet 1610, but not within the second sachet 1620. The second reactant 1640 is disposed within the second sachet 1620. Thus, the first reactant 1630 is separated from the second reactant 1640 by the second sachet 1620.

The rigid frame can be constructed from any rigid materials such as the barrier materials described above. For example, the rigid materials can include polyvinylchloride, polyethylene, polypropylene, polyester, styrene, polystyrene, polyethylene terephthalate, polyethylene terephthalate glycol, acrylobutylstyrene, polyacrylate, nylon, polyamide, and combinations thereof. The reactants can be any of the reactants described above. The reactants can be mixed or separated in separate volumes, e.g., sodium chlorite can be disposed in the first sachet and citric acid in the second sachet. Optionally the reactants can include additives. Preferably, one or more of the reactants is mixed with activated hydrotalcite.

The sachet layers can be constructed from any of the sachet materials described herein. For example, the sachet layers can be constructed from a water vapor selective material, e.g., a PTFE/PE layer as described above. The sachet layers can also be constructed from a layer that initially allows entry of water but subsequently impedes the passage of water. Without wishing to be bound to any particular theory, it is believed that the layer swells upon introduction of water to the layer and that the layer allows passage of water until the layer swells to such an extent that water can no longer pass through the pores. In a currently preferred embodiment, the first sachet layer is constructed from a water vapor selective material, the second sachet layer is constructed from a layer that initially allows entry of water but subsequently impedes the passage of water, and the rigid layer is injection molded PVC.

The apparatus can further include additional sachet layers and/or envelope layers adjacent the first and second sachet layers (not shown). The additional sachet layers and envelope layers can be constructed of any of the materials described herein. The first and second reactant can be any of the reactants described herein. The apparatus can further include additional sachets, envelopes, and/or reactant additives, such as desiccants, stabilizers and the like as described above. While preferred, the second sachet is optional and the reactants need not be separated in any manner.

Figure 23A:
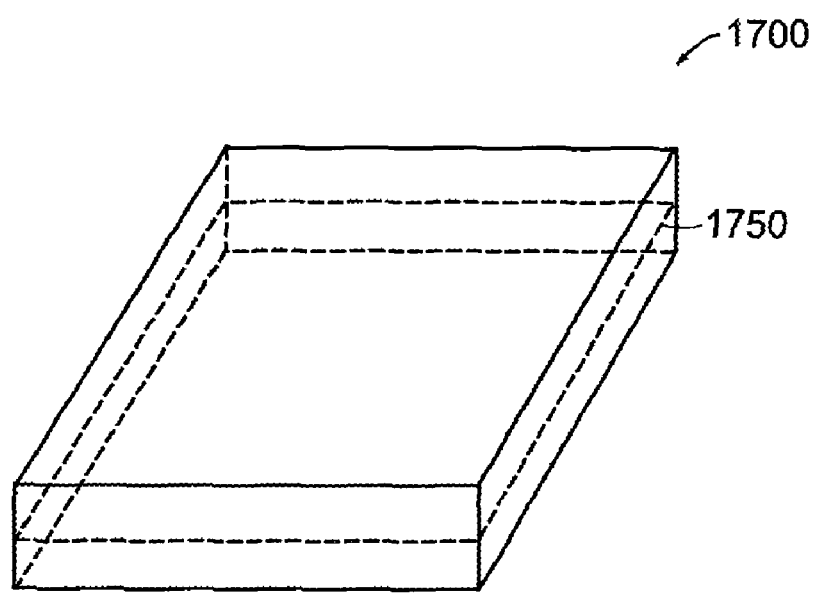
FIGS. 23A and 23B are a perspective and cross-sectional side view, respectively, of another exemplary embodiment of an apparatus including a sachet constructed in part with a rigid frame.
Figure 23B:
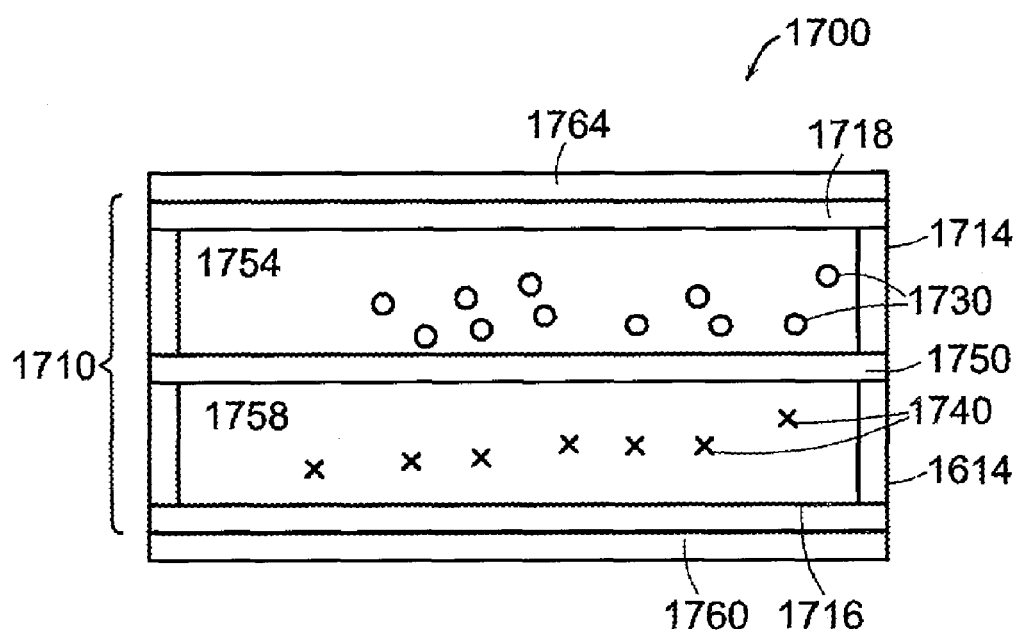

FIGS. 23A and 23B are a perspective and cross-sectional side view, respectively, of another exemplary embodiment of an apparatus 1700 including a sachet constructed in part with a rigid frame. The apparatus 1700, includes a sachet 1710, an intermediate layer 1750, a first reactant 1730, and a second reactant 1740. The sachet 1710 is constructed from a rigid frame 1714 having a square cross-section and two sachet layers 1716, 1718 disposed on either side of the rigid frame 1714 such that the rigid frame 1714 and the sachet layers 1716, 1718 define a closed receptacle for reactant. The rigid frame 1714 is bisected by the intermediate layer 1750, which defines a first volume 1754, and a second volume 1758. The first reactant 1730 is disposed in the first volume 1754, and the second reactant 1740 is disposed in the second volume 1758. Thus, first reactant 1730 is separated from second reactant 1740 by the intermediate layer. The apparatus 1700 further includes a first envelope layer 1760 disposed adjacent the first sachet layer 1716, and a second envelope layer 1764 adjacent the second sachet layer 1718.

The rigid frame, sachet layers, and envelope layers can be constructed from any of the materials described herein. For example, the rigid frame can be constructed from PVC, and the sachet layers can be constructed from a water vapor selective material. Optionally, one or more of the sachet layers can be constructed from a layer that initially allows entry of water but then impedes the passage of water. The apparatus can further include additional sachet layers and/or envelope layers adjacent the first and second sachet layers (not shown). The additional sachet layers and envelope layers can be constructed of any of the materials described herein. The first and second reactant can be any of the reactants described herein. The apparatus can further include additional sachets, envelopes, and/or reactant additives, such as desiccants, stabilizers and the like as described above. While preferred, the second sachet is optional and the reactants need not be separated in any manner.

Sachets including a rigid frame can be constructed by any of the method described herein, e.g., by adhesives and/or heat sealing the sachet layers, and optionally envelope layers, to the rigid frame. Additional sachets and/or enveloped within or about the sachet including the rigid frame can be constructed by any method known in the art including those described herein. The intermediate layer and the rigid frame portions also can be attached by any of the methods described herein. Apparatus including such sachets can be used in any applications described herein, including, but not limited to, use in a conduit, humidifier, and in both wet or dry applications.

Fluid Dispersion System for Dispersing a Gas

Yet another aspect of the present invention is a fluid dispersion system for dispersing a gas. The system includes any of the apparatus for delivery of a gas described herein, and a fluid dispersion apparatus. The fluid dispersion apparatus can disperse liquids and/or gasses. The apparatus for delivery of a gas can be placed at any point of the fluid dispersion apparatus, e.g., in a liquid reservoir or a fluid outlet of the fluid dispersion apparatus, so that gas is generated and dispersed. The fluid dispersion apparatus can be any fluid dispersion apparatus known in the art, including vaporizers, humidifiers, sonicators that disperse fluid, atomizers, and carpet cleaners.

Figure 24:
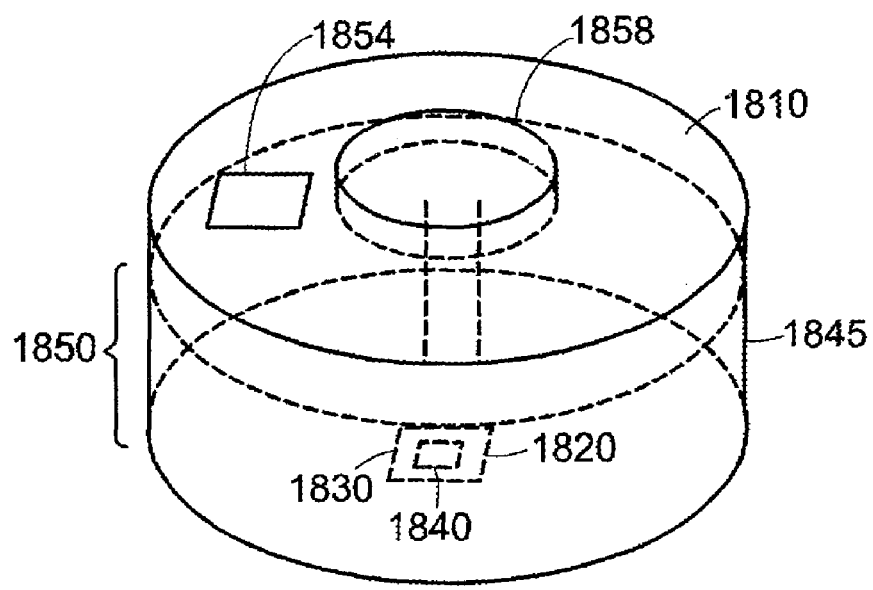
FIG. 24 is a perspective view of an exemplary embodiment of a fluid dispersion system constructed in accordance with the present invention.
Figure 25:
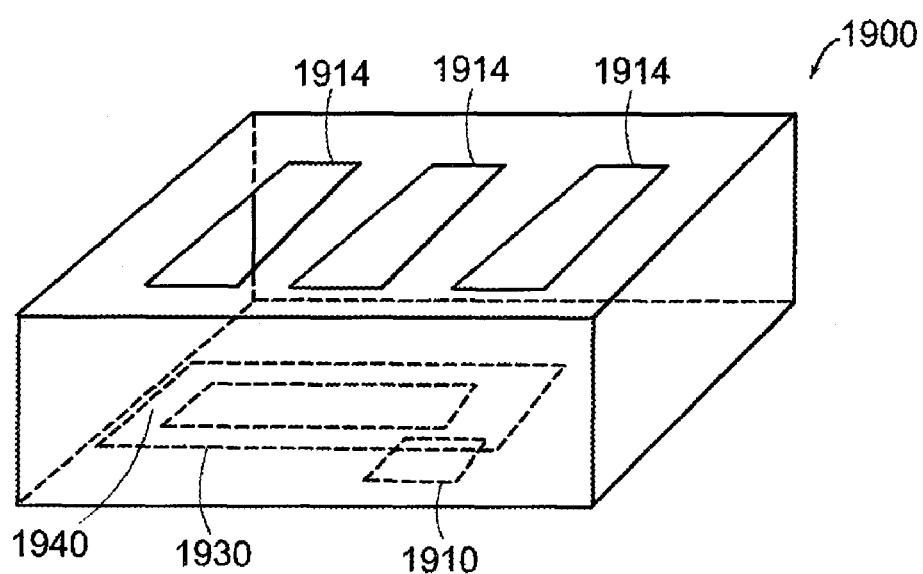
FIG. 25 is a perspective view of a housing for use with a fluid dispersion system in accordance with the present invention.
Figure 26:
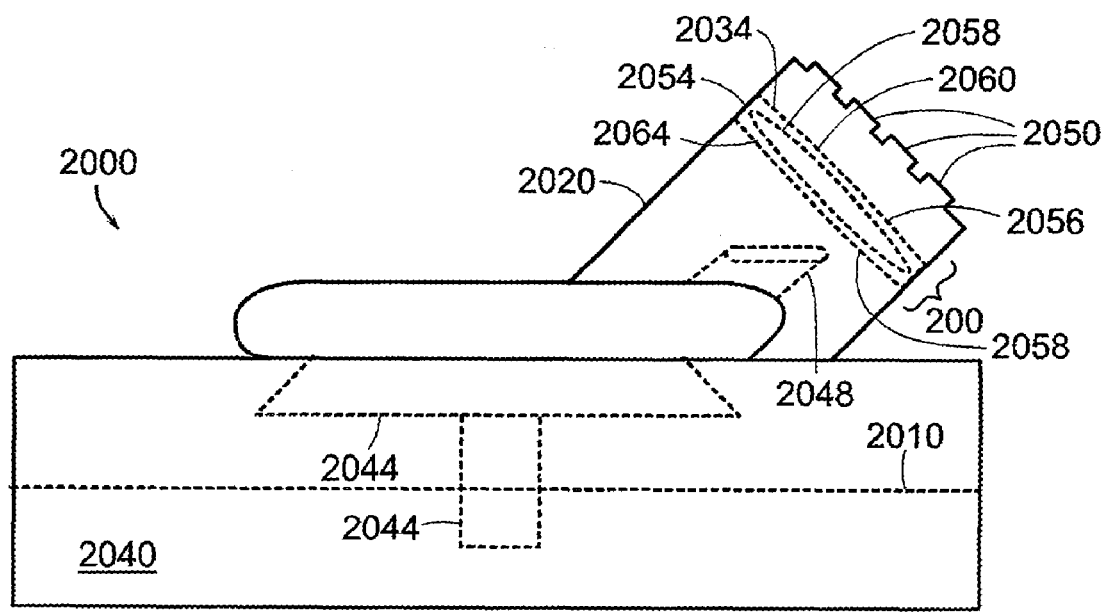
FIG. 26 is a side view of another exemplary embodiment of a fluid dispersion system constructed in accordance with the present invention.

FIG. 24 depicts an exemplary embodiment of a fluid dispersion system 1800 constructed in accordance with the present invention. The fluid dispersion system 1800 includes a fluid dispersion apparatus 1810, and a gas delivery apparatus 1820. The gas delivery apparatus 1820 includes a sachet 1830 and a reactant 1840 disposed in the volume defined by the sachet 1830 that generates gas in the presence of an initiating agent. In this embodiment the fluid dispersion apparatus 1810 is a humidifier and the sachet is disposed in a fluid reservoir 1845. The reservoir contains a fluid 1850 that includes an initiating agent. Alternatively, the sachet can be disposed in a dispersion outlet as shown in FIGS. 25 and 26.

The gas delivery apparatus 1820 can be any of the gas delivery apparatus described herein. For example, the sachet 1830 can comprise two adjacent sachet layers, a barrier layer adjacent a sachet layer, or a rigid frame defining an opening and a sachet layer disposed about the opening. The sachet 1820 can also include further sachets, one or more envelope and/or envelope layers, further reactants, and additives, such as stabilizers and desiccants (not shown). The sachet can be affixed within the fluid dispersion apparatus by mechanical means, can float freely in the fluid reservoir, or it can include a weight or be constructed from material such that the sachet sinks to the bottom of the reservoir as shown in FIG. 24.

The fluid dispersion apparatus 1810 includes a means of atomizing the fluid 1858, and an opening 1854 through which the atomized fluid containing the gas exits the fluid dispersion apparatus 1810. Means for atomizing fluids are well known.

The fluid dispersion 1810 apparatus can be any fluid dispersion apparatus known in the art. The fluid dispersion apparatus can disperse fluid by any means, including mechanical means, sonication, atomization, and/or vaporization. Many such fluid dispersion apparatus suitable for use with the present invention are readily available commercially as well as to consumers, for example, DURACRAFT™ Cool Mist™ humidifiers from Honeywell Consumer Products (Framingham, Mass.), which draws liquid into a rapidly spinning wheel with small openings and disperses atomized fluid into the environment. Also suitable are apparatus that disperse fluid by passing air over a wick that is in contact with a liquid such as the Cool MoistureTM Humidifier made by Honeywell Consumer Products.

In another aspect of the present invention, the fluid dispersion system can include a housing is provided that contains a gas delivery apparatus. The housing can be placed or affixed to a fluid dispersion apparatus outlet so that fluid exiting the fluid dispersion apparatus passes through the gas delivery apparatus so that gas and fluid exit the housing and enter the environment.

FIG. 25 depicts a housing for use with a fluid dispersion system in accordance with the present invention. The housing 1900 can be attached, e.g., to the fluid dispersion apparatus 1810 depicted in FIG. 24. The housing 1900 defines an opening 1910 defined by the housing for fluid dispersed by the fluid dispersion apparatus, and openings 1914, for expelling gas and fluid. Disposed in the housing 1900 is a sachet 1930 and a reactant 1940 disposed in the volume defined by the sachet that generates gas in the presence of an initiating agent. The housing 1900 can be attached to the fluid outlet of any fluid dispersion apparatus and the sachet 1930 can be used instead of or in addition to a sachet in the dispersion apparatus reservoir as depicted in FIG. 24.

FIG. 26 depicts another exemplary embodiment of a fluid dispersion system 2000 constructed in accordance with the present invention. The fluid dispersion system 2000 includes a fluid dispersion apparatus 2010, a housing 2020, and a gas delivery apparatus 2030. The gas delivery apparatus 2030 includes a sachet 2034 and a reactant 2038 disposed in the volume defined by the sachet that generates gas in the presence of an initiating agent. In this embodiment the fluid dispersion apparatus 2000 is a humidifier and the sachet 2034 is disposed in the housing 2020. The reservoir contains a fluid 2040 that includes an initiating agent.

The fluid dispersion apparatus 2010 includes a means of atomizing the fluid 2044, and an opening 2048 through which the atomized fluid containing the gas exits the fluid dispersion apparatus 2010 and enters the housing 2020. The housing 2020 defines openings 2050 that allow exit of the gas and the atomized fluid from the housing 2020.

The gas delivery apparatus 2030 is disposed within the housing and can be attached or affixed to the housing. The sachet includes a rigid frame 2054 defining a first opening 2056 and a second opening 2058. The sachet further includes a first sachet layer 2060 and a second sachet layer 2064 disposed about the first opening 2056 and the second opening 2058, respectively. The sachet can be affixed or removably attached to the housing by any known means (not shown), e.g., a snap fit.

Alternatively, the gas delivery apparatus 2030 can be any of the gas delivery embodiments described herein. For example, the gas delivery apparatus can further include additional sachets, sachet layers, envelope layers, envelopes, additional reactant and/or additives as described herein. The gas dispersion apparatus can be any gas dispersion apparatus including those described above.

The fluid dispersion system described herein can be used to sanitize, deodorize and/or reduce or eliminate bacteria in a fluid reservoir of the fluid dispersion apparatus, e.g., water in a humidifier or vaporizer. Additionally or alternatively, the system can be used to disperse chlorine dioxide and/or other gases into the environment to destroy or mask odor-causing compounds. The systems also could be used to disinfect the surrounding environment and kill or inactivate pathogens, such as anthrax, smallpox, tuberculosis, or legionella.

A preferred method of deodorizing includes the steps of providing a fluid dispersion system as described above, and delivering the gas to one or more odor-causing compounds, wherein the gas inactivates the one or more odor-causing compounds. A preferred method of inactivating pathogens includes the steps of providing the fluid dispersion system described above and delivering the gas to one or more pathogens, wherein the gas inactivates the one or more pathogens, such as anthrax, smallpox, tuberculosis, or legionella.

Apparatus for Delivery of a Gas to a Reservoir and/or Conduit

Figure 27:
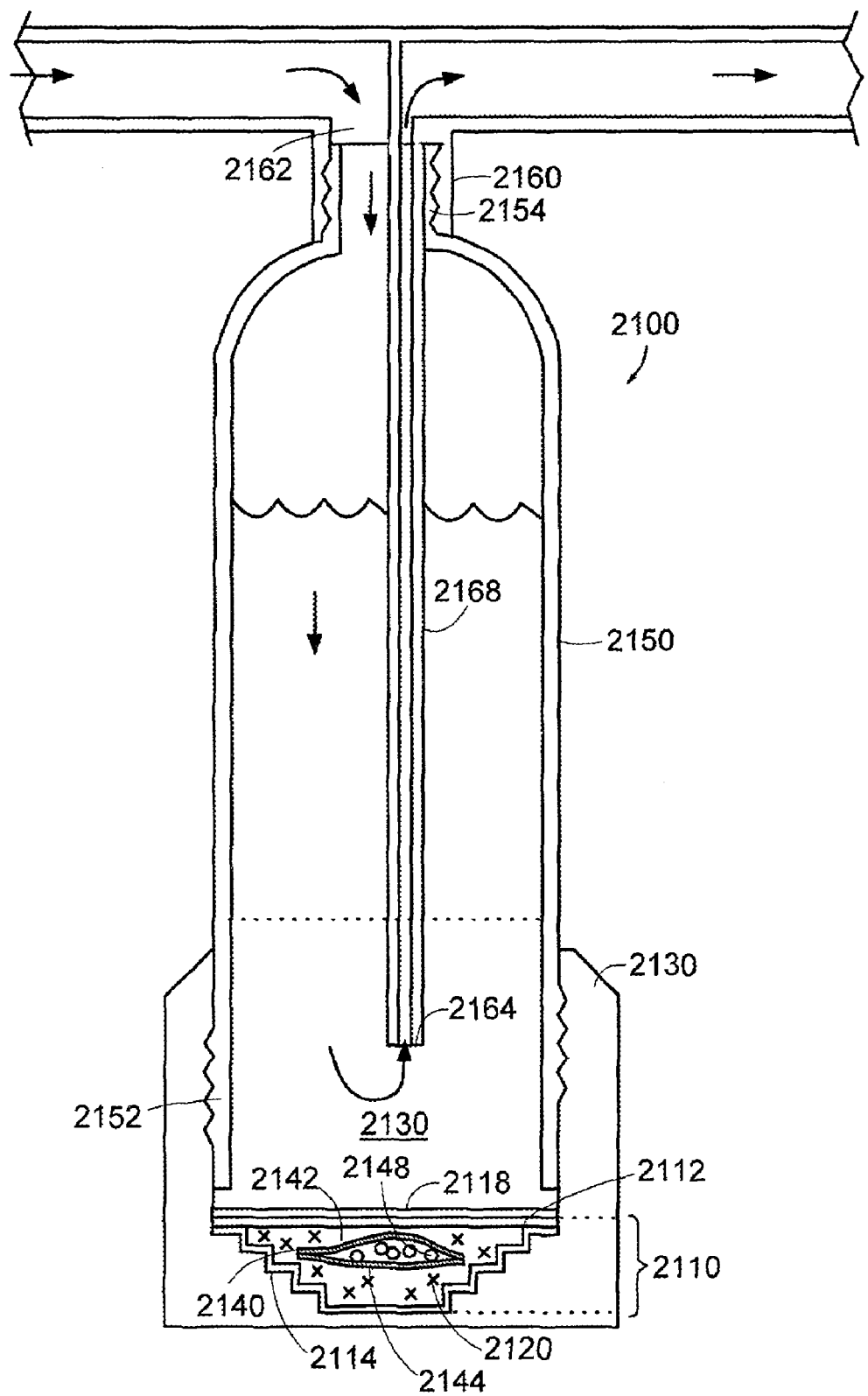
FIG. 27 is a cross-sectional side view of another exemplary embodiment of an apparatus for delivery of a gas to a reservoir.

Yet another aspect of the present invention is a method and apparatus for delivery of a gas to a reservoir. The apparatus generally includes any apparatus for delivery of a gas described herein in fluid connection with a reservoir. One such apparatus is depicted in FIG. 18, wherein the tubular bottle 1106 is the reservoir, and insert 1132, disposed within tubular bottle 1106, is the apparatus for delivery of a gas. The gas can further be delivered from the reservoir to a dispersion apparatus such as the pump mechanism 1112, or a humidifier as shown in FIGS. 24 and 26. Another exemplary apparatus is depicted in FIG. 16B, wherein the cap 985 and spout 880 define the reservoir, and the barrier layer 950 and sachet layer 930 define the sachet. The cap depicted in FIG. 16B can be coupled to a pouch as described or to a conduit (not shown). FIG. 27 depicts another exemplary embodiment of an apparatus 2100 for delivery of a gas to a reservoir. The apparatus 2100 generally includes a sachet 2110, a reactant 2120 disposed within the volume defined by the sachet 2110, and a reservoir 2130. The sachet 2110 includes a sachet layer 2112, a barrier layer 2114. An envelope layer 2118 is disposed adjacent the sachet layer 2112. Disposed in the volume defined by the sachet 2110 is a second sachet 2140 constructed from two sachet layers 2142, 2144, and a second reactant 2148 disposed in the second sachet 2140.

The reservoir 2130 has first end adapted to couple to a second reservoir 2150, so that the reservoir 2130 can be detached from the second reservoir 2150 for removal and replacement of the sachet 2110, the reactant 2120, the second sachet 2140 and second reactant 2148. The second reservoir 2150 comprises a first end 2152 adapted to couple to the reservoir 2130, and a second end 2154 adapted to couple to a conduit 2160. Conduit 2160 is formed to define an inlet 2162 for fluid to enter reservoir 2130, and an outlet 2164 with tubular member 2168 for fluid to exit reservoir 2130.

Figure 28:
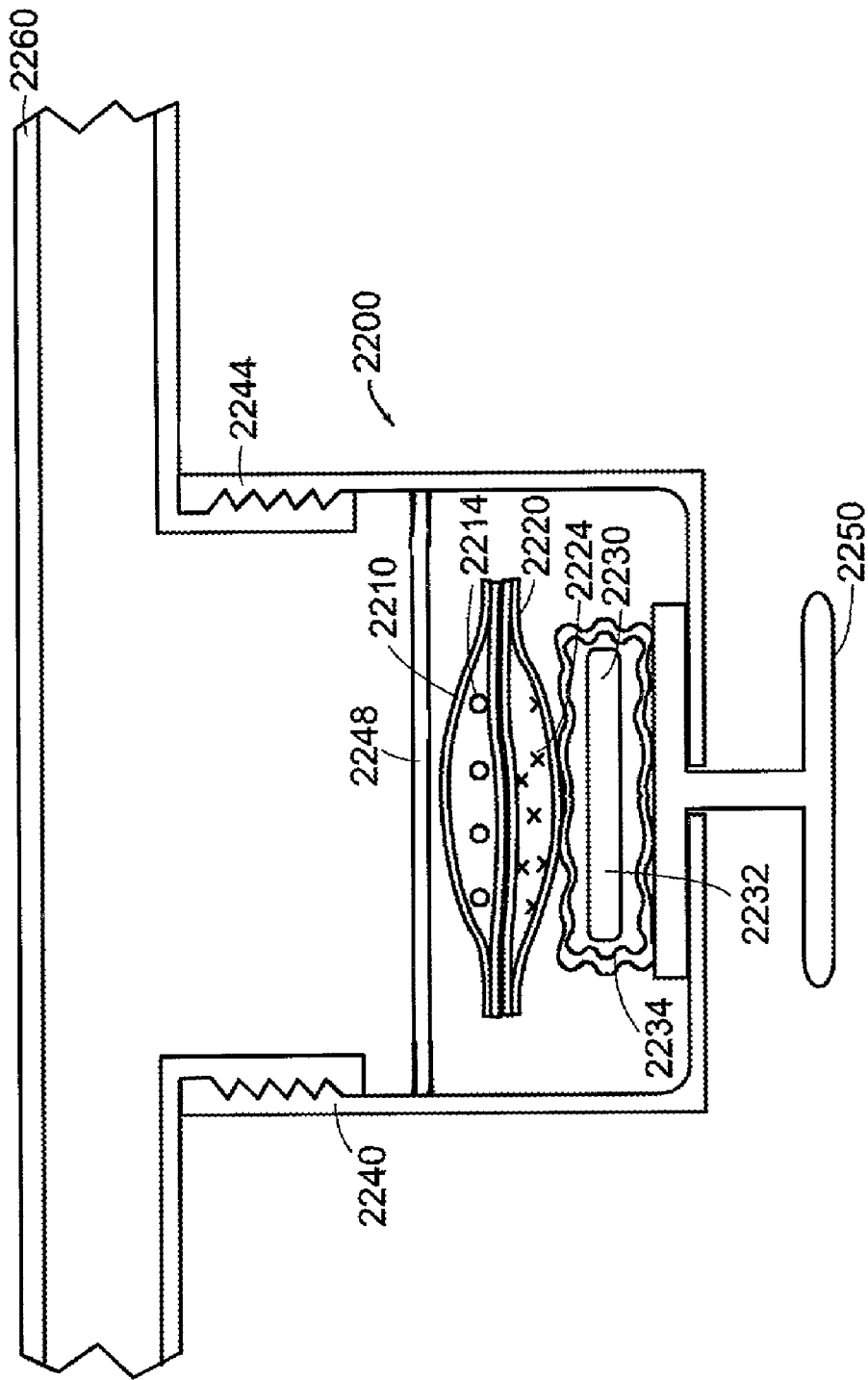
FIG. 28 is a cross-sectional side view of yet another exemplary embodiment of an apparatus for delivery of a gas to a reservoir.

FIG. 28 depicts yet another exemplary embodiment of an apparatus 2200 for delivery of a gas to a reservoir. The apparatus 2200 includes a reservoir 2240, a first sachet 2210, a first reactant 2214 disposed in the volume defined by the first sachet 2210, a second sachet 2220, and a second reactant 2224 disposed in the volume defined by the second sachet 2224. The first sachet 2210 and the second sachet 2220 each are constructed from two adjacent sachet layers sealed about their perimeters to define a closed receptacle for the first reactant 2214 and the second reactant 2224, respectively.

The sachets may be constructed from any of the materials described herein. The reactants can include any of the reactants described herein and can further include additives such as flow agents, desiccants and stabilizers. The apparatus can further include additional envelopes or sachets (not shown).

The apparatus further includes a frangible pouch 2230 disposed within the reservoir 2240, an initiating agent 2232 disposed within the frangible pouch 2230, and a sock 2234 disposed about the frangible pouch 2230. The sock 2234 can be constructed from any material that does not impede the passage of initiating agent out of it and that substantially retains the frangible pouch 2230 after it is disrupted. The sock 2234 is optional, but desirable when the frangible pouch is constructed of brittle materials, e.g., brittle plastic or glass, so that the frangible pouch pieces are substantially retained within the sock. Examples of sock materials suitable for use in accordance with the present invention are meshes made from polymers or natural fibers such as cotton or cellulose, or non-wovens such as TYVEK® non-woven materials made by DuPont Company (Wilmington, Del.) or the non-woven materials sold by Marubeni Corporation (Tokyo, Japan).

The apparatus further includes a piston 2250 mounted to the reservoir 2240 that upon actuation disrupts the frangible pouch 2230. Reservoir 2140 includes a first end 2244 adapted to couple to a conduit 2260, and a retaining layer 2248 that retains the sachets 2210, 2220 and the frangible pouch 2230 in the reservoir 2140. Upon disruption of the frangible pouch 2230, the initiating agent 2232 is released and reaction is initiated. The sock 2234 retains the pieces of the frangible pouch 2230.

Many variations and alternative designs can readily be made without departing from the spirit and scope of the invention. For example, the sachets can be replaced by any of the gas delivery apparatus described herein and/or they can be further contained in additional sachets or envelopes. For example, the sachets, frangible pouch, and sock can be enclosed within a sachet or envelope attached to the reservoir and the retaining layer not included such that the outer sachet or envelope retains the sachets, frangible pouch and sock in the reservoir. Any of the reactants described herein can be used. Reactants can be mixed or separated, e.g., by a sachet or an intermediate layer. Additives can also be included in the apparatus, such as activated hydrotalcite. The conduit can be any conduit, such as a beverage line.

Yet another aspect of the present invention is a method of delivering a gas to a conduit. The method include the steps of providing an apparatus for delivery of a gas including a sachet and a reactant disposed within the volume defined by the sachet that generates a gas in the presence of an initiating agent, and a reservoir in fluid communication with the sachet. The method further includes the steps of coupling the apparatus to a conduit, and delivering a gas to the conduit by introducing an initiating agent to the reactant.

The conduit can be any conduit where introduction of a gas is desired. Introduction of a gas, e.g., chlorine dioxide, is particularly useful when it is desired to sanitize, disinfect, remove biofilms, and/or kill, inhibit or inactivate pathogens in an aqueous fluid, gas or liquid. The apparatus can be used to flush and clean out conduits between regular usage or to introduce chlorine dioxide gas during regular usage. The conduit can be a food or beverage conduit, such as a beverage line in a beverage dispensing machine, a conduit in equipment used to make food or beverages, or a water line in a water dispenser such as a fountain or bubbler. The conduit can be part of a dental apparatus such as a water line. The conduit can be part of a medical apparatus, such as an analyzer. The conduit can be a conduit in a commercial or household appliance such as a dishwasher or coffeemaker.

EXAMPLE 1

An Apparatus in Accordance with the Present Invention

A membrane sachet was constructed by impulse sealing the perimeter of two 3 cm×3 cm sheets of 0.65 micron pore hydrophilic polyethylene membrane sold under the trade designation MPLC obtained from Millipore (Bedford, Mass.). The sheets were impulse sealed a 16" TISH400 Impulse Sealer available from TEW Electric Heating Equipment Corporation (Taiwan). This sachet was filled with 50 mg of sodium chlorite and 200 mg citric acid. The sachet was then placed into an envelope formed by impulse sealing the perimeter of a 4 cm×6 cm perforated film. The perforated film used was a SM700 Cryovac® perforated film from Sealed Air Corporation (Duncan, S.C.). This assembly was then placed in a 1 liter plastic bag filled with water for 15 minutes. The chlorine dioxide concentration in the water was measured using a Beckman DU-520 UV-Vis Spectrophotometer set at a wavelength of 360λ at about 6 mg/L.

COMPARATIVE EXAMPLE 2

Direct Addition of Reactant to Water 50 mg of sodium chlorite and 200 mg citric acid were added to 1 liter of water. The solution was allowed to sit for 15 minutes. The chlorine dioxide concentration in the water was measured using a Beckman DU-520 UV-Vis Spectrophotometer set at a wavelength of 360λ at about 0.5 mg/L. FIGS. 8 and 10 depict gas generation over time for adding the same amount and ratio of reactants to water.

EXAMPLE 3

An Apparatus Without an Envelope

An apparatus was constructed as described in Example 1, except that the envelope was not included. This assembly was then placed in a 1 liter plastic bag filled with water for 15 minutes. The chlorine dioxide concentration in the water was measured using a Beckman DU-520 UV-Vis Spectrophotometer set at a wavelength of 360λ at about 5.5 mg/L. Such an apparatus and exemplary use of the same are depicted in FIG. 10.

EXAMPLE 4

An Apparatus Having Two Sachets

Two sachets were constructed by impulse sealing the perimeter of four 3 cm×3 cm sheets of 0.65 micron pore hydrophilic polyethylene membrane sold under the trade designation MPLC obtained from Millipore (Bedford, Mass.). The first sachet was filled with 400 mg of sodium chlorite and the second sachet was filled with 1200 mg citric acid. Both sachets were then enclosed in an envelope formed by impulse sealing the perimeter of a 4 cm×6 cm SM700 film obtained from Sealed Air Corporation having 330 holes per square inch having a diameter of 0.4 mm, a 6.4% perforated area and a water vapor transmission rate of 700 g/m$^2$/24 hr. This apparatus was then placed in a 1 liter plastic bag filled with water and let stand for 180 minutes. The chlorine dioxide concentration was measured using a Beckman DU-520 UV-Vis Spectrophotometer set at a wavelength of 360λ 100 mg/L.

EXAMPLE 5

An Apparatus Having Three Sachets and a Frangible Pouch Containing an Initiating Agent Two sachets were constructed in accordance with Example 4 except that the sachets were constructed from 3 micron pore nylon 6,6 material sold under the trade designation BIO-DYNE A from Pall (Port Washington, N.Y.). The first sachet was filled with 500 mg of sodium chlorite and the second sachet was filled with 2000 mg citric acid. Both sachets were then enclosed in a third sachet formed by impulse sealing the perimeter of a 5 cm×7 cm 0.65 micron pore, hydrophobic polypropylene membrane sold under the trade designation DOHP by Millipore (Bedford, Mass.). A frangible pouch was constructed and filled with 5 ml of water. The frangible pouch and the third sachet (containing the first and second sachets and reactant) were then enclosed in an envelope formed by impulse sealing the perimeter of a 7 cm×9 cm multilayered polymer film having a carbon dioxide transmission rate of 7,000 cc/m$^2$/24 hrs and an oxygen transmission rate of 21,000 cc/m$^2$/24 hrs sold under the trade designation PD-961 Cryovac® selective transmission film from Sealed Air Corporation (Duncan, S.C.). The frangible pouch was burst using manual pressure and this apparatus was then placed in a 1 liter plastic bag filled with water and let stand for 180 minutes. The chlorine dioxide concentration in the water was measured using a Beckman DU-520 UV-Vis Spectrophotometer set at 360λ at 100 mg/L.

EXAMPLE 6

An Apparatus Having an Envelope and a Bridge

A two-compartment membrane sachet was constructed by impulse sealing the perimeter of a 3 cm×3 cm sheets of 0.65 micron pore hydrophilic polypropylene membrane, sold under the trade designation MPLC obtained from Millipore (Bedford, Mass.), between two 3 cm×3 cm sheets of 0.65 micron pore hydrophobic polyethylene membrane sold under the trade designation DOHP by Millipore (Bedford, Mass.). Thus was formed a two compartment sachet having hydrophilic membrane on its outer walls and a divider of hydrophobic membrane for separating the reactant in each compartment. The first compartment of the sachet was filled with 50 mg of sodium chlorite and the second compartment was filled with 200 mg citric acid. This multi-compartment sachet was then placed into an envelope formed by heat-sealing the perimeter of a 4 cm×6 cm perforated film. The perforated film used was a SM700 Cryovac® perforated film from Sealed Air Corporation (Duncan, S.C.). This assembly was then placed in a 1 liter plastic bag filled with water for 15 minutes. The chlorine dioxide concentration in the water was measured using a Beckman DU-520 UV-Vis Spectrophotometer set at 360λ wavelength at about 8 mg/L.

EXAMPLE 7

An Apparatus for Generating Carbon Dioxide

A sachet was constructed by impulse sealing the perimeter of two 3 cm×3 cm sheets of 0.65 micron pore hydrophilic polyethylene membrane, sold under the trade designation MPLC obtained from Millipore (Bedford, Mass.). This sachet was filled with 50 mg of calcium carbonate and 100 mg citric acid. The sachet was then placed into an envelope formed by impulse sealing the perimeter of a 4 cm×6 cm perforated film. The perforated film used was a SM700 Cryovac® perforated film from Sealed Air Corporation (Duncan, S.C.). This assembly was then placed in a 1 liter plastic bag filled with water for 15 minutes. The carbon dioxide concentration in the water was measured using analyzed by ion chromatography at about 50 mg/L.

EXAMPLE 8

An Apparatus for Long-Term Release

A sachet was constructed by impulse sealing the perimeter of two 4 cm×6 cm sheets of 0.65 micron pore hydrophilic polyethylene membrane, sold under the trade designation MPLC obtained from Millipore (Bedford, Mass.). This sachet was filled with 500 mg of sodium chlorite and 2000 mg citric acid. The sachet was then placed into an envelope formed by impulse sealing the perimeter of a 4 cm×6 cm perforated film. The perforated film used was 0.1 micron pore hydrophobic polypropylene membrane sold under the trade designation DOHP by Millipore (Bedford, Mass.). This apparatus was then placed in a 2 liter plastic bag filled with water. The chlorine dioxide concentration was measured every hour using a Beckman DU-520 UV-Vis Spectrophotometer set at a wavelength of 360λ. The apparatus generated about 3.5 mg per hour for 30 hours.

EXAMPLE 9

An Exemplary Apparatus in Accordance with the Present Invention

An exemplary apparatus was constructed by sealing the perimeter of 6.1 cm diameter sheets of nylon 6,6 membrane layer sold under the trade designation 045ZY by Cuno Incorporated (Meriden, Conn.) and SM700 Cryovac® perforated film from Sealed Air Corporation (Duncan, S.C.) to a barrier layer filled with 240 mg of sodium chlorite, 60 mg of activated hydrotalcite, and 1,200 mg citric acid. The barrier layer was formed from polyvinyl chloride to define a barrier layer similar to barrier layer 50 depicted in FIGS. 12A, 12B and 12C. It had an outside a diameter of 6 cm and a 0.5 cm deep cavity formed therein having a 4.8 cm inside diameter. The layers were sealed about the edge of the barrier layer with an epoxy adhesive between the impermeable layer and the nylon 6,6 membrane layer, and between the nylon 6,6 membrane layer and the perforated film layer. The surface area of the nylon 6,6 layer adjacent to the reactant was about 18 cm$^2$ and the volume defined by the barrier layer and the nylon 6,6 layer was about 9 cm$^3$. This assembly was attached by a snap fit to the interior wall of a polypropylene cap having a threaded fit to the spout of a 1 liter blow molded high density polyethylene plastic bottle. The bottle was filled with 1 liter of water, sealed with the cap, and turned upside down and left to stand. The chlorine dioxide concentration in the water was measured using a Hach DR890 Colorimeter and the standard Hach chlorine dioxide method at about 25 mg/L at 45 minutes and about 42 mg/L at 60 minutes. Hach Colorimeters are available from Hach Company (Loveland, Colo.). A similar apparatus and exemplary use of the same are depicted in FIGS. 16A and 16B.

PROSPECTIVE EXAMPLE 10

An Exemplary Apparatus with a Sachet and Envelope

A membrane sachet will be constructed by impulse sealing the perimeter of two 3 cm×3 cm sheets of nylon 6,6 membrane layer sold under the trade designation 045ZY by Cuno Incorporated (Meriden, Conn.). The sheets are to be impulse sealed with a 16" TISH400 Impulse Sealer available from TEW Electric Heating Equipment Corporation (Taiwan). This sachet will be filled with 240 mg of sodium chlorite, 60 mg of activated hydrotalcite, and 1,200 mg citric acid. The sachet will then be placed into an envelope formed by impulse sealing the perimeter of a 4 cm×6 cm perforated film. The perforated film used will be a SM700 Cryovac® perforated film from Sealed Air Corporation (Duncan, S.C.). This assembly will then be placed in a 1 liter plastic bag filled with water for 15 minutes. The chlorine dioxide concentration in the water will be measured using a Hach DR890 Colorimeter and the standard Hach chlorine dioxide method. It is expected that readings of about 25 mg/L at 45 minutes and about 42 mg/L at 60 minutes will be obtained. Such an apparatus and exemplary use of the same are depicted in FIGS. 1A and 1B.

PROSPECTIVE EXAMPLE 11

An Exemplary Apparatus Including a Pouch and a Sealed Spout

An exemplary apparatus will be constructed as described in Example 9, except that this assembly will be fused to the interior wall of a one liter pouch. The pouch will be constructed from a 5 mil thick impermeable layer comprising a polyester exterior, a metallized biaxially oriented core, and a polyethylene interior sealing layer obtained from Sealed Air Corporation (Duncan, S.C.). This layer has a water vapor transmission rate of 0.01 g/100 in2/24 hours at 70% relative humidity and 122° F. The spout will be constructed of injection molded polypropylene. The pouch will be sealed about its perimeter except for the opening defined by the spout. The one liter pouch will then be filled with water, capped, and allowed to stand. The chlorine dioxide concentration in the water will be measured as described in Example 9 and similar chlorine dioxide concentrations are expected at 45 and 60 minutes. Such an apparatus and exemplary use of the same are depicted in FIG. 15.

EXAMPLE 12

Apparatus Having Reactants Mixed with Hydrotalcite

Hydrotalcite, obtained from Alcoa World Chemicals (Leetsdate, Pa.), was activated by disposing the hydrotalcite on a tray in a layer not more than 1 inch thick, and placing the tray in a furnace at 500° C. for one hour. The hydrotalcite was stored in a closed, airtight container. The hydrotalcite was weighed before and after activation, and demonstrated an approximately 40% weight loss, believed to be attributable to loss of water and carbon dioxide in the furnace. Dry, flaked technical sodium chlorite (80%) obtained from Vulcan Chemical (Birmingham, Ala.), was ground to a mesh particle size range between about 35 mesh and 70 mesh using a mechanical impact milling system (particle size ranged between about 212 microns and 500 microns). The activated hydrotalcite was mixed with the ground sodium chlorite to form a mixture of about 80% sodium chlorite and about 20% activated hydrotalcite by weight. The sodium chlorate/hydrotalcite mixture was then mixed in a dry environment (71° F., 40% relative humidity) with desiccated granular citric acid having a particle size range between about 25 mesh and about 60 mesh. The citric acid was desiccated by exposing it to dry air (less than 40% relative humidity for a period of 24 hours with frequent mixing. The resulting mixture was approximately 80% citric acid and 20% sodium chlorite/hydrotalcite mixture by weight.

Approximately 1.75 grams of this mixture was sealed in a sachet. The sachet and a 1 gram molecular sieve desiccant were sealed in a 1 liter plastic bag measuring approximately 7.5 inches by 9 inches constructed from a composite of a 1 mil thick metallized biaxially oriented polypropylene film and a 5 mils thick linear low density polyethylene film. The bag was sealed with a polypropylene spout and cap. The apparatus was stored at room temperature, which ranged from about 68° F. to about 80° F., and ambient humidity, which ranged from about 50% relative humidity to about 90% relative humidity. The apparatus was stable at 6 months in that no reaction between the sodium chlorite and the citric acid was detected at 6 months.

EXAMPLE 13

Apparatus Having Two Sachets and Sodium Chlorite Mixed with Hydrotalcite

The reactants and hydrotalcite described in Example 12 were obtained. The sodium chlorite was ground, the hydrotalcite activated, and the citric acid desiccated, as described in Example 12. A mixture of approximately 95% sodium chlorite and 5% activated hydrotalcite by weight was made. Approximately 4.3 grams of this mixture was sealed in a first sachet, and approximately 20 grams of desiccated citric acid was sealed in a second sachet. These two sachets were sealed in a 5½ inch by 3½ inch envelope constructed from hydrophobic, polypropylene non-woven membrane sold under the designation 060P1 by Cuno Incorporated (Meriden, Conn.). The sachets and envelope, and 2 grams of molecular sieves desiccant were sealed in a 2-liter plastic bag measuring approximately 7.5 inches by 14 inches constructed from a composite of a 1 mil thick metallized biaxially oriented polypropylene film and a 5 mils thick linear low density polyethylene film. The bag was sealed with a polypropylene spout and cap. The apparatus was stored under the same conditions as described in Example 12. The apparatus was stable at 6 months in that no reaction between the sodium chlorite and the citric acid was detected at 6 months.

EXAMPLE 14

Apparatus Having a Sachet Constructed from Water Vapor Selective Material

Six sets of reactant/hydrotalcite mixtures were each prepared for inclusion in a sachet as follows: 350 grams of a mixture of approximately 80% sodium chlorite obtained from Vulcan Chemical (Birmingham, Ala.) and 20% activated hydrotalcite obtained from Alcoa World Chemicals (Leetsdale, Pa.), was mixed with 1400 milligrams of desiccated citric acid from JT Baker (Phillipsburg, N.J.).

Four of the reactant/hydrotalcite mixtures were each impulse sealed in a sachet constructed from two 1.75 mils thick, 2.5 inch by 2.5 inch hydrophobic polytetrafluoroethylene (PTFE) layers having a 1.5 micron average nominal pore size thermally bonded to a 5 mil thick, BHA-TEX® hydrophobic polyethylene (PE) support layer from BHA Technologies (Kansas City, Mo.). The remaining two reactant/hydrotalcite mixtures were each impulse sealed in a sachet constructed from two 2.5 inch by 2.5 inch, 0.65 micron pore size, extruded hydrophobic polypropylene layer sold under the trade designation DOHP by Millipore (Bedford, Mass.).

Figure 29:
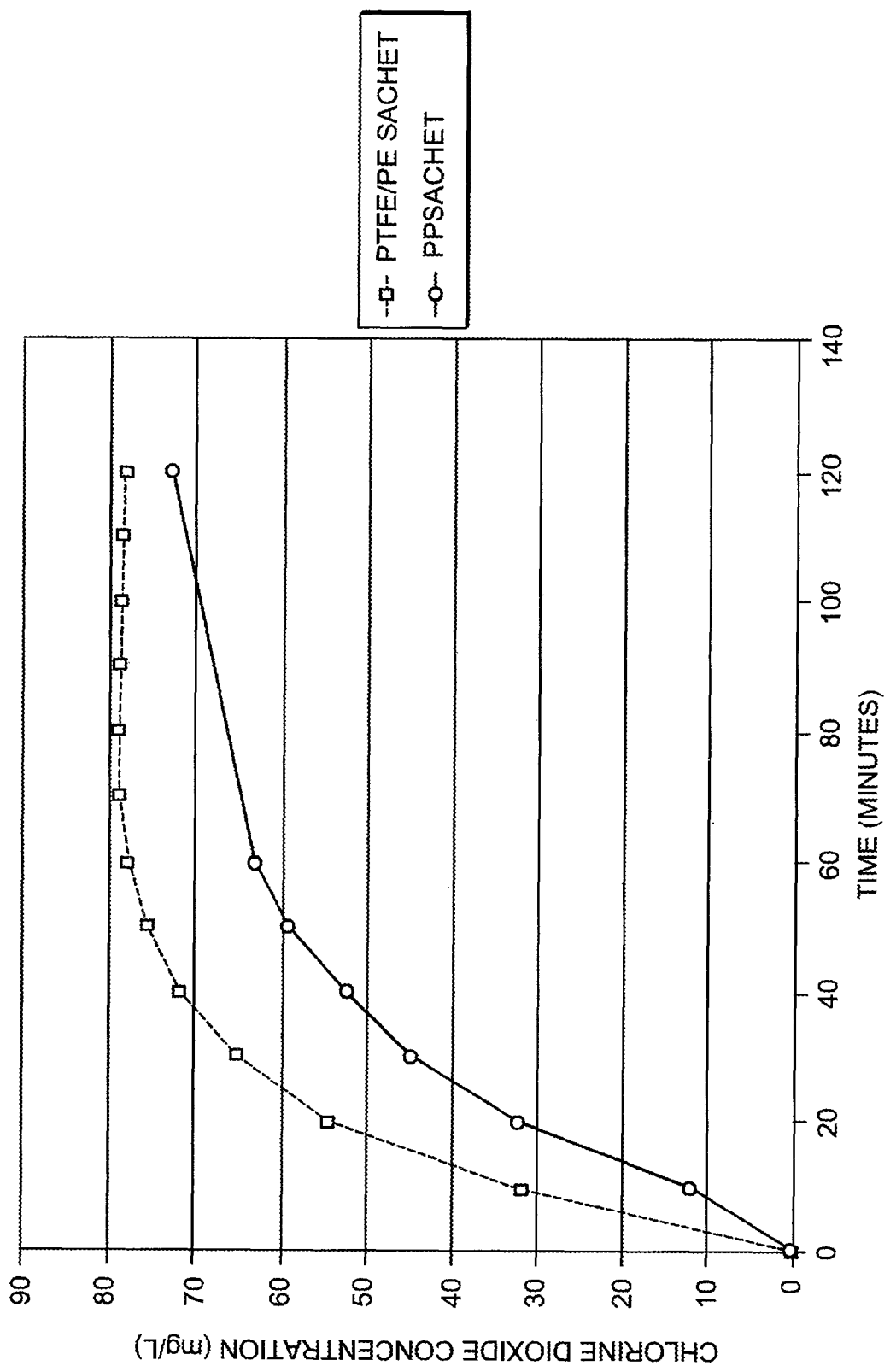
FIG. 29 is a graph depicting chlorine dioxide concentration versus time comparing exemplary apparatus fabricated with different hydrophobic sachet materials.

Each of the six total sachets were sealed in a 1 liter plastic bag filled with water. The chlorine dioxide concentration in the water was measured every 10 minutes using a Hach DR890 Colorimeter and the standard Hach chlorine dioxide method. FIG. 29 is a graph depicting chlorine dioxide concentration versus time comparing the above sachet materials. The square-shaped data points correspond to the averaged values for the apparatus constructed with the PTFE/PE sachet layers. The circle-shaped data points correspond to averaged values for apparatus constructed with the PP sachet layers. As can be seen from FIG. 29, the apparatus having the PTFE/PE sachet generated chlorine dioxide more rapidly than the apparatus with the PP sachet. This due, at least in part, to use of a thinner PTFE water vapor selective material, as compared to the relatively thicker PP water vapor selective material. In addition, the apparatus having the PTFE/PE sachet generated more chlorine dioxide, resulting in a more highly concentrated solution than the solution generated by the apparatus with the PP membrane.

EXAMPLE 15

Apparatus Having a Rigid Frame

A rigid frame of PVC pipe, cylindrical in shape and measuring about 2.54 cm in length, having an inner diameter of about 3.81 cm, and an inner volume of about 29 $cm^3$ was obtained. The first end was sealed with the PTFE/PE layer used in the preceding example. A mixture of approximately 95% sodium chlorite and 5% activated hydrotalcite by weight was made as described in Example 13. About 2.9 grams of the mixture was enclosed in a sachet measuring 1.5 inches square, and made of heat sealable water soluble paper made by Mishima Paper Co. (Tokyo, Japan). The sachet and about 13.6 grams of desiccated citric acid were disposed in the vessel formed from the rigid frame and the PTFE/PE sachet layer, and a second layer of the same PTFE/PE sachet material was sealed on the second end of the rigid frame, thus forming a substantially closed sachet volume of about 29 cm³. The layers were sealed to the rigid frame by using Scotch® 300LSE Hi Strength adhesive made by the 3M Company (Minneapolis, Minn.). The membrane/adhesive/rigid frame bond was allowed to cure for 24 hours prior to use. The resulting apparatus was placed in about 2 liters of water. After 24 hours, the chlorine dioxide concentration was measured using a Hach DR890 Colorimeter and the standard Hach chlorine dioxide method. The chlorine dioxide concentration was about 346.7 ppm.

EXAMPLE 16

Apparatus Having an Envelope Constructed with a Water Vapor Selective Material

Seventy sets of reactant envelopes, each containing two reactant sachets, were prepared in the following manner. 4.3 grams of a mixture of approximately 95% technical grade sodium chlorite obtained from Vulcan Chemicals (Birmingham, Ala.), and 5% activated hydrotalcite obtained from Alcoa World Chemicals (Leetsdale, Pa.), were sealed in a 2.75 inch×2.75 inch sachet made of heat sealable water soluble paper made by Mishima Paper Co. (Tokyo, Japan). 20 grams of desiccated citric acid monohydrate obtained from J. T. Baker (Phillipsburg, N.J.), were sealed inside a second sachet, measuring 3.25 inches×4 inches, also made of rice paper. These two sachets were then sealed inside a hydrophobic envelope having dimensions of 4.75 inches×4 inches.

Sixty-seven sets of reactant sachets impulse sealed in a water vapor selective envelope constructed of a non-woven polypropylene membrane sold under the trade designation S8500240H by Cuno Incorporated (Meridan, Conn.). The remaining three sets of reactant sachets were sealed, using Scotch™ 300LSE Hi Strength Adhesive (3M Corporation, Minneapolis, Minn.), in a water vapor selective envelope constructed of a 1.75 mil thick PTFE layers thermally bonded to a 5 mil thick polyethylene (PE) mesh support material resulting in a final envelope material thickness of approximately 5 mils which is sold under the trade designation BHA-TEX® by BHA Technologies (Kansas City, Mo.). The envelopes were constructed with the PTFE layer on the inside, near the reactant sachets, and the adhesive was allowed to cure for 24 hours prior to testing.

Figure 30:
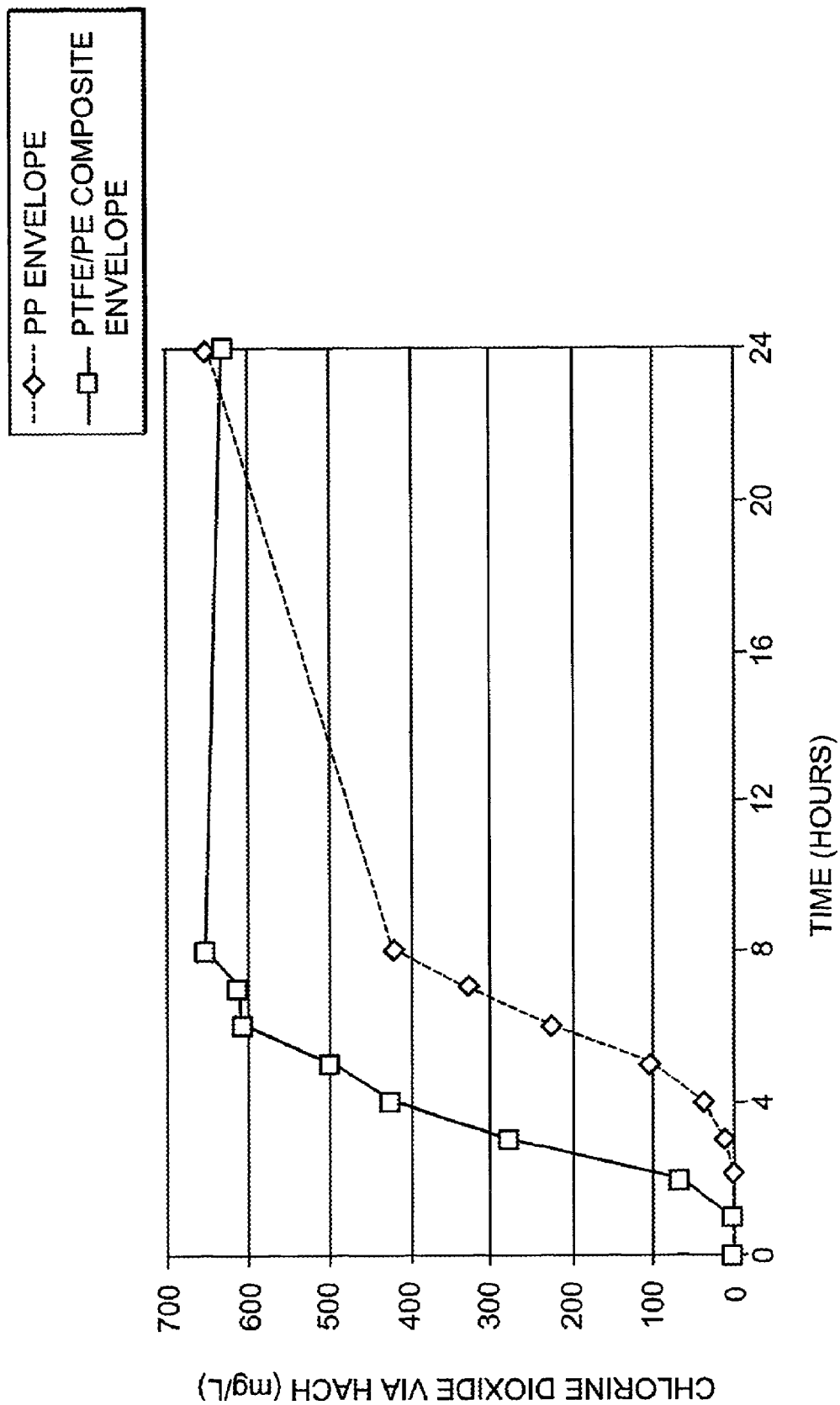
FIG. 30 is a graph depicting chlorine dioxide concentration versus time comparing exemplary apparatus fabricated with different hydrophobic envelope materials.

Each of the seventy envelopes was sealed in a 2-liter plastic bag that was filled with liquid water. The chlorine dioxide concentration in the water was measured periodically, over a 24-hour period, using a Hach DR890 Colorimeter and the standard Hach chlorine dioxide method. FIG. 30 is a graph depicting the chlorine dioxide concentration versus time comparing the above envelope materials. The diamond-shaped data points correspond to the averaged values for the apparatus constructed with the non-woven polypropylene envelope material. The square-shaped data points correspond to the averaged values for the apparatus constructed with the PTFE/PE composite envelope material. As can be seen from FIG. 30, the apparatus having the PTFE/PE envelope generated chlorine dioxide more rapidly than the apparatus with the polypropylene envelope.

Although generally the preferred embodiments of the invention have been shown and described, numerous variations and alternative embodiments will occur to those skilled in the art. Accordingly, it is intended that the invention be limited only in terms of the appended claims as the invention can be embodied in other specific forms.

What is claimed is:

1. An apparatus for delivery of a gas comprising:
    a sachet comprising a hydrophobic water vapor selective membrane; and
    an aqueous soluble reactant disposed within the sachet that generates chlorine dioxide in the presence of an initiating agent, wherein the water vapor selective membrane has a water vapor permeability between 2,000 g/m²/24 hrs and 150,000 g/m²/24 hrs, such that the sachet substantially impedes the permeation of a water soluble species out of the apparatus when immersed in water.

2. The apparatus of claim 1, wherein the water vapor selective membrane has a thickness between about 0.15 mils and 15 mils, and a nominal average pore size between about 0.05 microns and about 10 microns.

3. The apparatus of claim 1, wherein the sachet further comprises a support layer disposed adjacent the water vapor selective membrane.

4. The apparatus of claim 1, wherein the reactant is selected from the group consisting of acids, aqueous acids, citric acid, oxalic acid, fumaric acid, phosphoric acid, potassium bitartrate, chlorites, chlorates, sulfites, bisulfites, sulfates, carbonate, nitrites, and combinations thereof.

5. The apparatus of claim 1, further comprising:
    a second sachet disposed within the sachet; and
    a second reactant disposed within the second sachet.

6. An apparatus for delivery of a gas comprising:
    a sachet comprising a hydrophobic water vapor selective membrane;
    a partition disposed within the sachet defining a first volume and a second volume;
    a first aqueous soluble reactant disposed within the first volume; and
    a second aqueous soluble reactant disposed within the second volume,
    wherein the first reactant and the second reactant generate chlorine dioxide in the presence of an initiating agent, and
    wherein the water vapor selective membrane has a water vapor permeability between 2,000 g/m²/24 hrs and 150,000 g/m²/24 hrs, such that the sachet substantially impedes the permeation of a water soluble species out of the apparatus when immersed in water.

7. The apparatus as in claim 1 or 6, wherein the sachet precludes the permeation of a water soluble species out of the apparatus.

8. The apparatus of claim 7, wherein the water soluble species is a reactant.

9. The apparatus of claim 7, wherein the water soluble species is an additive.

10. The apparatus of claim 7, wherein the water soluble species is a by-product.

11. The apparatus of claim 7, wherein the sachet has a pore size between about 0.01 microns and about 50 microns.

12. The apparatus of claim 7, further comprising a stabilizer disposed within the sachet.

13. The apparatus of claim 12, wherein the stabilizer is an activated hydrotalcite.

14. An apparatus for delivery of a gas comprising:
    a sachet comprising a hydrophobic water vapor selective membrane; and
    an aqueous soluble reactant disposed within the sachet that generates chlorine dioxide in the presence of an initiating agent, wherein the sachet has a water intrusion pressure between 100 millibars and 1500 millibars; and wherein the water vapor selective membrane has a water vapor permeability between 2,000 g/m$^2$/24 hrs and 150,000 g/m$^2$/24 hrs, such that the sachet substantially impedes the permeation of a water soluble species out of the apparatus when immersed in water.

15. The apparatus of claim 14, wherein the sachet has a water intrusion pressure between 200 millibars and 750 millibars.

* * * * *